US011384399B2

(12) United States Patent
LaFleur et al.

(10) Patent No.: US 11,384,399 B2
(45) Date of Patent: Jul. 12, 2022

(54) METHODS FOR SUBTYPING DIFFUSE LARGE B-CELL LYMPHOMA (DLBCL)

(71) Applicant: HTG Molecular Diagnostics, Inc., Tucson, AZ (US)

(72) Inventors: Bonnie LaFleur, Tucson, AZ (US); Qian Liu, Lynn, MA (US); John W. Luecke, Tucson, AZ (US); Patrick C. Roche, Tucson, AZ (US)

(73) Assignee: HTG Molecular Diagnostics, Inc., Tucson, AZ (US)

( * ) Notice: Subject to any disclaimer, the term of this patent is extended or adjusted under 35 U.S.C. 154(b) by 893 days.

(21) Appl. No.: 15/756,641

(22) PCT Filed: Sep. 29, 2016

(86) PCT No.: PCT/US2016/054501
§ 371 (c)(1),
(2) Date: Mar. 1, 2018

(87) PCT Pub. No.: WO2017/059108
PCT Pub. Date: Apr. 6, 2017

(65) Prior Publication Data
US 2018/0340231 A1 Nov. 29, 2018

Related U.S. Application Data

(60) Provisional application No. 62/234,491, filed on Sep. 29, 2015.

(51) Int. Cl.
*C12Q 1/6886* (2018.01)
(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 8,741,564 B2 | 6/2014 | Seligmann et al. |
| 2011/0152115 A1 | 6/2011 | Staudt et al. |
| 2011/0223157 A1 | 9/2011 | Schafer et al. |

FOREIGN PATENT DOCUMENTS

| CN | 102224255 | 10/2011 |
| JP | 2013-522236 A | 6/2013 |
| JP | 2014-512838 A | 5/2014 |

(Continued)

OTHER PUBLICATIONS

Roberts et al. (Laboratory Investigation (2007) vol. 87:979-997).*

(Continued)

*Primary Examiner* — Lori A. Clow
(74) *Attorney, Agent, or Firm* — Klarquist Sparkman, LLP

(57) ABSTRACT

Described herein are innovations for classifying subtypes of DLBCL, as well as using the results of classification for diagnosis, prognosis, and therapy selection. In this way, the classifier can effectively classify subtypes of DLBCL and provide meaningful output for the benefit of medical practices and DLBCL patients. Also described are arrays and kits that can be used to measure expression of DLBCL signatures genes.

33 Claims, 9 Drawing Sheets
Specification includes a Sequence Listing.

(56) References Cited

FOREIGN PATENT DOCUMENTS

| WO | WO2010/019952 | 2/2010 |
|---|---|---|
| WO | WO 2015/069790 | 5/2015 |

OTHER PUBLICATIONS

Rimsza et al. (Blood (2008) vol. 112:3425-3433).*
Rimsza et al. (PLoS One (2011) vol. 6:8 pages).*
Bourzac et al. (Journal of Biotechnology (2011) vol. 154:68-75).*
Affymetrix, "Gene Profiling Array cGMP U133 P2," pp. 1-2, XP007920950, Jan. 1, 2012.
Alizadeh et al., "Distinct types of diffuse large B-cell lymphoma identified by gene expression profiling," *Nature* 403:503-511, 2000.
Friedman et al., "Regularization Paths for Generalized Linear Models via Coordinate Descent," *J Stat Softw.* 33:1-22, 2010.
Reinholz et al., "Next-Generation Sequencing for DLBCL Classification," Poster Abstract 11559, American Society of Clinical Oncology Annual Meeting in Chicago, Illinois, Jun. 3 to Jun. 7, 2016.
Roberts et al., "Quantitative nuclease protection assay in paraffin-embedded tissue replicates prognostic microarray gene expression in diffuse large-B-cell lymphoma," *Lab Invest.* 87:979-997, 2007.
Tibshirani, R., "Regression Shrinkage and Selection via the Lasso," *J R Statist Soc. B* 58:267-288, 1996.

Wright et al., "A gene expression-based method to diagnose clinically distinct subgroups of diffuse large B cell lymphoma," *Proc Natl Acad Sci. USA* 100:9991-9996, 2003.
PCTUS2016054501 Written Opinion and International Search Report dated Dec. 18, 2016 (12 pages).
Jais et al., "The Expression of 16 Genes Related to the Cell of Origin and Immune Response Predicts Survival in Elderly Patients With Diffuse Large B-cell Lymphoma Treated With CHOP and Rituximab," *Leukemia* 22:1917-1924, 2008.
Rimsza et al., "Accurate Classification of Diffuse Large B-cell Lymphoma Into Germinal Center and Activated B-cell Subtypes Using a Nuclease Protection Assay on Formalin-Fixed, Paraffin-Embedded Tissues," *Clin Cancer Res.* 17:3727-3732, 2011.
Visco et al., "Comprehensive Gene Expression Profiling and Immunohistochemical Studies Support Application of Immunophenotypic Algorithm for Molecular Subtype Classification in Diffuse Large B-cell Lymphoma: A Report From the International DLBCL Rituximab-CHOP Consortium Program Study," *Leukemia* 26:2103-2113, 2012.
Mounter & Gisselbrecht, "Relapses, treatments and new drugs," *Best Practice &. Research Clinical Haematology*, vol. 25, No. 1, pp. 49-60, 2012.
Roschewski et al., "Diffuse large B-cell lymphoma-treatment approaches in the molecular era," *Nature Reviews Clinical Oncology*, vol. 11, No. 1, 29 pages, 2014 (Epub 2013).

* cited by examiner

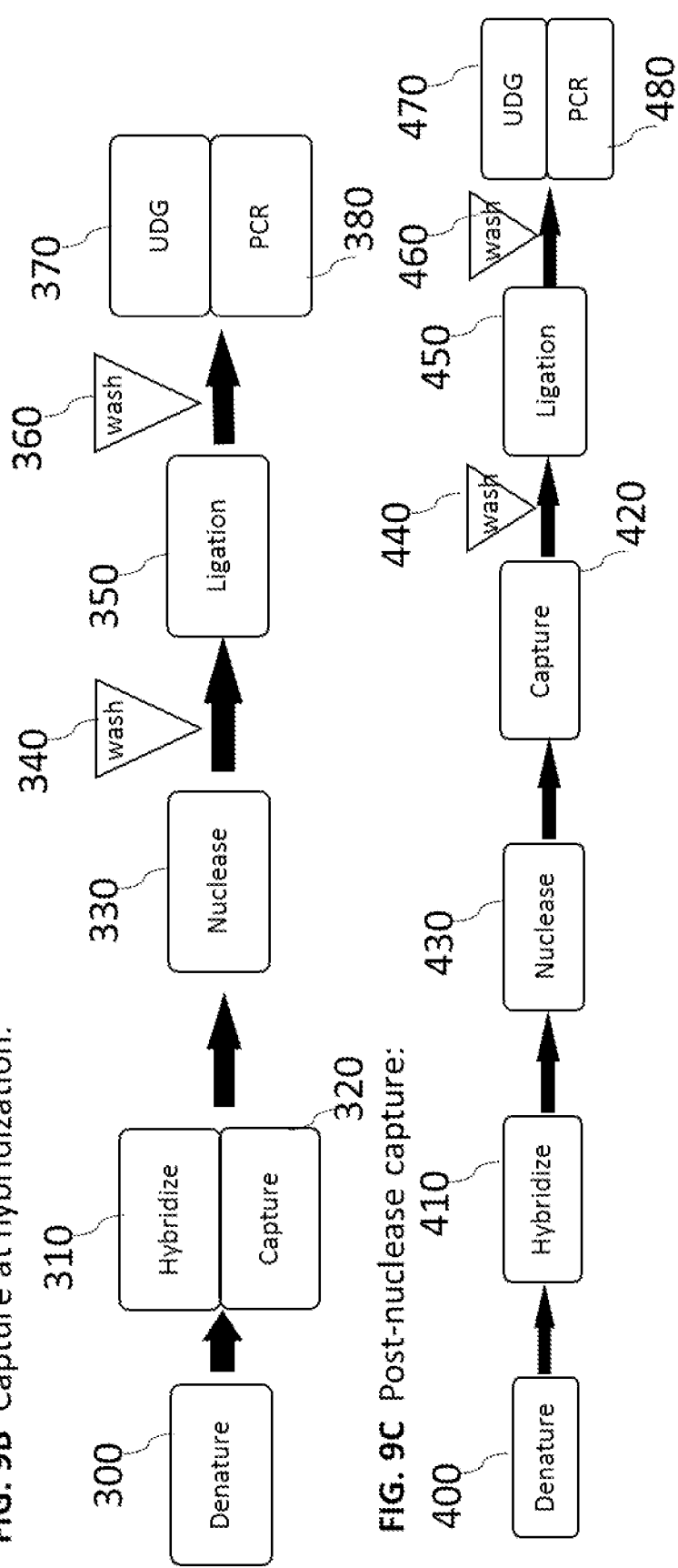
FIG. 9B Capture at hybridization:
FIG. 9C Post-nuclease capture:
FIG. 9D Post-Hybridization capture:

SEQUENCE LISTING

```
<160> NUMBER OF SEQ ID NOS: 16

<210> SEQ ID NO 1
<211> LENGTH: 50
<212> TYPE: DNA
<213> ORGANISM: Artificial Sequence
<220> FEATURE:
<223> OTHER INFORMATION: Capture portion of NPPF used to detect CD47

<400> SEQUENCE: 1
aaactggtta cctagaggcc agaggcccta ggacctgaaa ggcatcattc         50

<210> SEQ ID NO 2
<211> LENGTH: 50
<212> TYPE: DNA
<213> ORGANISM: Artificial Sequence
<220> FEATURE:
<223> OTHER INFORMATION: capture portion of NPPF used to detect CD86

<400> SEQUENCE: 2
gtctcctctt ggcatacgga gcagagctgg agttacaggg aggctattcc         50

<210> SEQ ID NO 3
<211> LENGTH: 50
<212> TYPE: DNA
<213> ORGANISM: Artificial Sequence
<220> FEATURE:
<223> OTHER INFORMATION: cpature portion of NPPF used to detect ENTPD1

<400> SEQUENCE: 3
```

-continued ccatgaggaa gacataggtg gagtgggaga gaggtgtgga caatggttgc    50

<210> SEQ ID NO 4
<211> LENGTH: 50
<212> TYPE: DNA
<213> ORGANISM: Artificial Sequence
<220> FEATURE:
<223> OTHER INFORMATION: Capture portion of NPPF used to detect FOXP1

<400> SEQUENCE: 4
ctcttcccgt attgcgctgg ctaagttgcc cagagtggga tttcccatgg    50

<210> SEQ ID NO 5
<211> LENGTH: 50
<212> TYPE: DNA
<213> ORGANISM: Artificial Sequence
<220> FEATURE:
<223> OTHER INFORMATION: Capture portion of NPPF used to detect FUT8

<400> SEQUENCE: 5
cagtttggct gaaatggttt gaactgagtt tggtcgaact gagtttggtc    50

<210> SEQ ID NO 6
<211> LENGTH: 50
<212> TYPE: DNA
<213> ORGANISM: Artificial Sequence
<220> FEATURE:
<223> OTHER INFORMATION: Capture portion of NPPF used to detect IL16

<400> SEQUENCE: 6
gtccatcagg cagtgccttg atgatgttcc aggcttcaaa ccgtgtgagg    50

<210> SEQ ID NO 7
<211> LENGTH: 50
<212> TYPE: DNA
<213> ORGANISM: Artificial Sequence
<220> FEATURE:
<223> OTHER INFORMATION: Capture portion of NPPF used to detect ITPKB

<400> SEQUENCE: 7
gcgcctcaaa catgcccact ttctggttca cctgcacgtt ctgcaactcg    50

<210> SEQ ID NO 8
<211> LENGTH: 50
<212> TYPE: DNA
<213> ORGANISM: Artificial Sequence
<220> FEATURE:
<223> OTHER INFORMATION: Capture portion of NPPF used to detect LRMP

<400> SEQUENCE: 8
gctatttcta cagcggttaa agtcctgata tgtcaagttg cctctttctg    50

<210> SEQ ID NO 9
<211> LENGTH: 50
<212> TYPE: DNA
<213> ORGANISM: Artificial Sequence
<220> FEATURE:
<223> OTHER INFORMATION: Capture portion of NPPF used to detect MME

<400> SEQUENCE: 9
ggccttgcgg aaagcatttc tggactcctt gtaggttcgg ctgaggctgc    50

<210> SEQ ID NO 10
<211> LENGTH: 50
<212> TYPE: DNA
<213> ORGANISM: Artificial Sequence

```
<220> FEATURE:
<223> OTHER INFORMATION: Capture portion of NPPF used to detect NF2

<400> SEQUENCE: 10
gagagaaatc tctacagggt cgtagttcaa ggcaattgca cataagaggg                50

<210> SEQ ID NO 11
<211> LENGTH: 50
<212> TYPE: DNA
<213> ORGANISM: Artificial Sequence
<220> FEATURE:
<223> OTHER INFORMATION: Capture portion of NPPF used to detect PIM1

<400> SEQUENCE: 11
gctcaccttc ttcagcagga ccacttccat gggcactcga gtgccattag                50

<210> SEQ ID NO 12
<211> LENGTH: 50
<212> TYPE: DNA
<213> ORGANISM: Artificial Sequence
<220> FEATURE:
<223> OTHER INFORMATION: Capture portion of NPPF used to detect PTPRC

<400> SEQUENCE: 12
ggaacaattt cctcctctgt taccctaaga acaaaccact tgctagctgc                50

<210> SEQ ID NO 13
<211> LENGTH: 50
<212> TYPE: DNA
<213> ORGANISM: Artificial Sequence
<220> FEATURE:
<223> OTHER INFORMATION: Capture portion of NPPF used to detect REL

<400> SEQUENCE: 13
cagaggtgcc attgaggcat gatgtgacaa tccacttgag atgggcccag                50

<210> SEQ ID NO 14
<211> LENGTH: 50
<212> TYPE: DNA
<213> ORGANISM: Artificial Sequence
<220> FEATURE:
<223> OTHER INFORMATION: Capture portion of NPPF used to detect STAT3

<400> SEQUENCE: 14
cagcttcagg atgctcctgg ctctctggcc gacaatactt tccgaatgcc                50

<210> SEQ ID NO 15
<211> LENGTH: 50
<212> TYPE: DNA
<213> ORGANISM: Artificial Sequence
<220> FEATURE:
<223> OTHER INFORMATION: Capture portion of NPPF used to detect TNFRSF8

<400> SEQUENCE: 15
ctgggaccaa tgctgttctc ggcagtgccc atcctgccat ctgtttgctg                50

<210> SEQ ID NO 16
<211> LENGTH: 50
<212> TYPE: DNA
<213> ORGANISM: Artificial Sequence
<220> FEATURE:
<223> OTHER INFORMATION: Capture portion of NPPF used to detect TYMS

<400> SEQUENCE: 16
cttcaggccc gtgatgtgcg caatcatgta cgtgagcagg gcgtagctgg                50
```

METHODS FOR SUBTYPING DIFFUSE LARGE B-CELL LYMPHOMA (DLBCL)

CROSS-REFERENCE TO RELATED APPLICATION

This is the § 371 U.S. National Stage of International Application No. PCT/US2016/054501, filed Sep. 29, 2016, which was published in English under PCT Article 21(2), which in turn claims priority to U.S. Provisional Application No. 62/234,491, filed Sep. 29, 2015, herein incorporated by reference.

FIELD

This disclosure relates to classifiers, arrays and kits for distinguishing subtypes of diffuse large B-cell lymphoma (DLBCL), as well as uses of the results of classification for diagnosis, prognosis, and/or therapy selection.

BACKGROUND

Lymphoma is the most common blood cancer. The two main forms of lymphoma are Hodgkin lymphoma and non-Hodgkin lymphoma. Diffuse large B-cell lymphoma (DLBCL) is the most common form of non-Hodgkin lymphoma, accounting for up to 30 percent of newly diagnosed cases. DLBCL may be further characterized on the basis of gene expression markers as germinal center B-cell-like (GCB) subtype or as a non-GCB-like (including activated B-cell-like (ABC)) subtype. GCB and non-GCB (such as ABC) subtyping may be used to (i) predict the prognosis of a lymphoma patient, with GCB-like lymphomas having a better prognosis than non-GCB (or ABC) subtypes, and/or (ii) determine treatments for lymphoma patients, for example, with GBC- or ABC-targeted therapies, or on the basis of disease aggressiveness (ABC generally more aggressive than GBC disease).

There is no single, accepted diagnostic test for distinguishing GCB and non-GCB (for example, ABC) DLBCL subtypes and/or for determining the prognosis of or treatment(s) for DLBCL patients. A few immunohistochemistry (IHC)-based tests are available in clinical practice, including Colomo et al. (*Blood* 101(1):78-84, 2003), Hans et al. (*Blood* 103:275-282, 2004), Muris et al. (*J. Pathol*, 208(5): 714-23, 2006). Choi et al. (*Mod. Pathol*, 21:250A, 2008), and Tally (Meyer et al. *J. Clin. Oncol.* 29(2):200, 2011) tests.

Because DLBCL has a wide variety of clinical outcomes, the molecular bases of the disease are thought to be equally complex, and the discovery of clinically useful biomarkers is ongoing. One goal of such work is "to subdivide this clinically heterogeneous diagnostic category into molecularly distinct diseases with more homogeneous clinical behaviors" (Alizadeh et al., *Nature* 403:503, 2000). In that regard, IHC is an inherently limited technology for at least the reason that only a limited number of protein biomarkers can be co-detected. Similarly, genome (e.g., DNA) analysis is limited for at least the reason that it is unclear whether a genomic event is expressed to have a functional impact on the biological system.

mRNA transcriptome analysis has advantages over both protein and DNA analysis because mRNA expression provides a snapshot of genomic activity and is amenable to multiplexing for the detection of many biomarkers in the same sample. A number of mRNAs differentially expressed in DLBCL samples have been reported (e.g., Alizadeh et al., *Nature*, 403:503, 2000; Rosenwald et al., *NEJM* 346(25): 1937, 2002; Wright et al., *Proc. Natl. Acad. Sci.* 100:9991, 2003; and Roberts et al., *Lab. Invest.* 78:979, 2007). However, significant and important gaps in this area remain to be solved.

SUMMARY

The identification of biomarkers whose expression is characteristic of DLBCL across a variety of detection technologies is an important first step (e.g., Roberts et al., *Lab. Invest.* 78:979, 2007). However, from a practical and clinical perspective, a remaining critical challenge is to synthesize vast amounts of arcane expression data into meaningful output(s) for the benefit of medical practices and DLBCL patients.

This disclosure describes innovations for classifying subtypes of DLBCL, as well as using the results of classification for diagnosis, prognosis and therapy selection. For example, a classifier (which can be computer-implemented) determines a subtype of DLBCL based on gene expression, such as expression levels for two or more signature genes in a sample from a subject with DLBCL. In some examples, expression is measured by a proportional number of sequencing reads for a given gene out of the total number of reads (wherein a read is the number of complementary copies of a specific sequence (e.g., from a probe) that can be read by a sequencer). The classifier can effectively classify subtypes of DLBCL and provide meaningful output for the benefit of medical practices and DLBCL patients.

According to one aspect of the innovations, the methods measure expression levels (e.g., nucleic acid or protein) for a plurality of DLBCL signature genes in a sample. For example, the method can measure expression of at least two of CD47, CD86, IL16, NF2, PIM1, PTPRC, REL, STAT3, TNFRSF8, and TYMS, or at least two of CD47, CD86, ENTPD1, FOXP1, FUT8, IL16, ITPKB, LRMP, MME, NF2, PIM1, PTPRC, REL, STAT3, TNFRSF8, and TYMS (such as measuring expression of all 16 of these genes). The resulting expression value for each gene can be weighted, and the weighted expression values summed. A probability score using the summed weighted expression values can be determined. The method or classifier scores or compares the probability score against corresponding thresholds for the DLBCL classifier. Then, based at least in part on results of the scoring, the method classifies the DLBCL sample as activated B-cell-like (ABC), germinal center B-cell-like (GCB), or unclassified. The classification of subtypes of DLBCL can be implemented as part of a method, as part of a computing system adapted to perform the method, or as part of a tangible computer-readable media storing computer-executable instructions for causing a computing system to perform the method.

The innovations described herein also include using the results of the classification for diagnosis, prognosis, and/or therapy selection for a subject with DLBCL. Also described herein are arrays and kits that can be used to determine expression of DLBCL signature genes.

The foregoing and other features of the disclosure will become more apparent from the following detailed description, which proceeds with reference to the accompanying figures.

SEQUENCE LISTING

Figure 1:
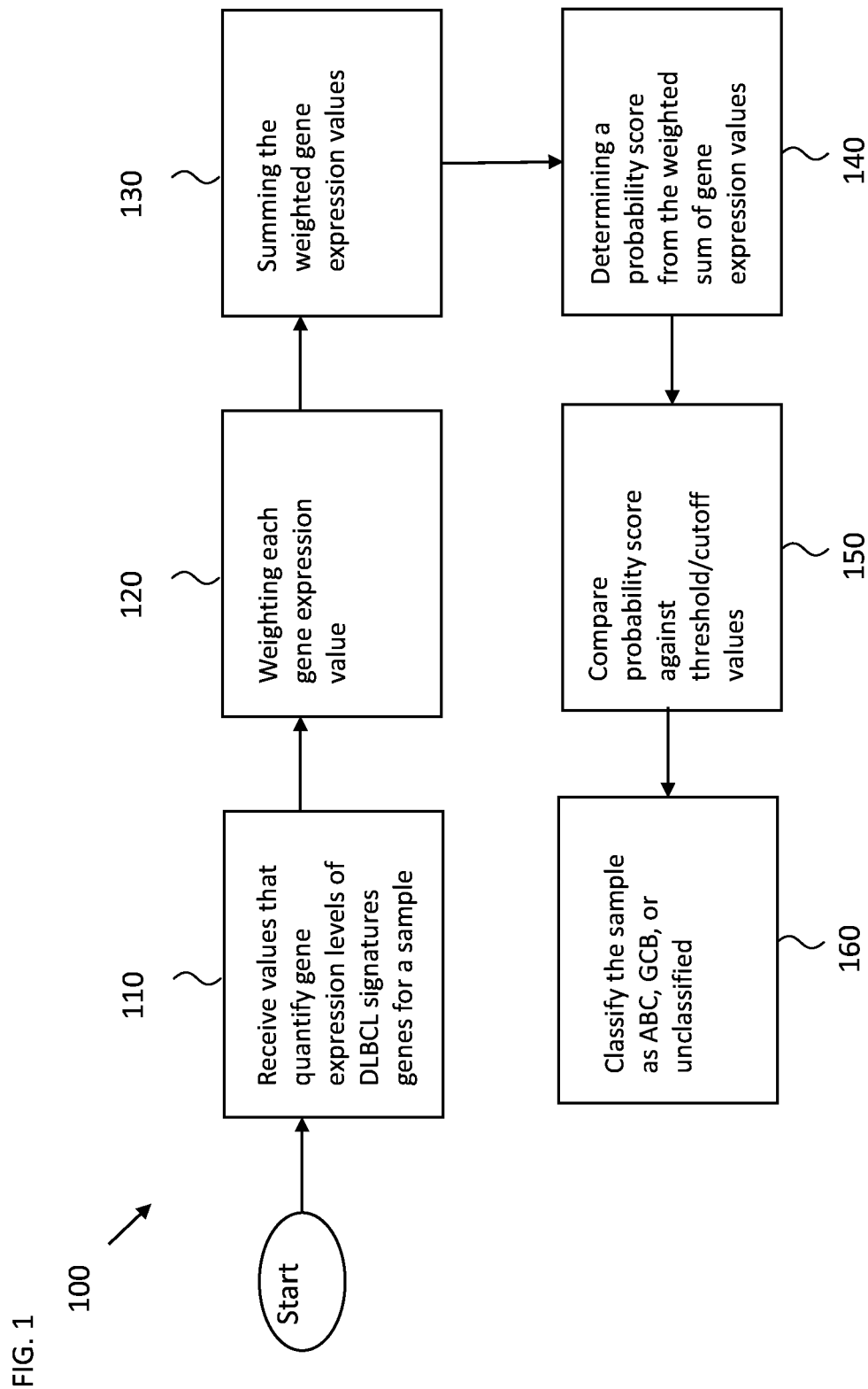
FIG. 1 is a flowchart illustrating a generalized technique for classifying subtype of DLBCL.

The nucleic acid sequences listed herein are shown using standard letter abbreviations for nucleotide bases, as defined in 37 C.F.R. 1.822. Only one strand of each nucleic acid sequence is shown, but the complementary strand is understood as included by any reference to the displayed strand. The sequence listing filed herewith is incorporated by reference (generated on Feb. 28, 2018 8 KB). In the provided sequences:

SEQ ID NOs: 1-16 are exemplary probe nucleic acid sequences.

DETAILED DESCRIPTION

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety, as are the GenBank® Accession numbers (for the sequence present on Sep. 29, 2015). In case of conflict, the present specification, including explanations of terms, will control. In addition, the materials, methods, and examples are illustrative only and not intended to be limiting.

Except as otherwise noted, the methods and techniques of the present disclosure are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999; each of which is specifically incorporated herein by reference in its entirety.

Overview

DLBCL is the most common type of non-Hodgkin lymphoma in adults. There are two main subtypes of DLBCL, germinal center B-cell-like (GCB) and non-GCB (typically, activated B-cell-like (ABC)). GCB generally is associated with favorable prognosis, while ABC or non-GBC is generally associated with poorer prognosis (e.g., is a more aggressive disease). Primary mediastinal B-cell lymphoma (PMBCL) is considered by some practitioners to be another subtype of DLBCL (Lossos, *J. Clin. Oncol.* 23:6351-6357, 2005). PMBCL arises in the thymus and typically presents as a mass in the mediastinum. Non-GCB subtypes of DLBCL include all DLBCL subtypes except the GCB subtype. Similarly, non-ABC subtypes of DLBCL include all DLBCL subtypes except the ABC subtype.

Innovations are described herein for classifying subtypes of DLBCL, as well as using the results of classification for diagnosis, prognosis, and/or therapy selection. Example classifiers determine a subtype of DLBCL based on gene expression levels for two or more signature genes in a sample from a subject with DLBCL. By effectively determining subtype of DLBCL, a classifier provides meaningful output for the benefit of medical practices and DLBCL patients.

Innovations described herein include classification methods (which can be wholly or partially computer-implemented), computer-readable media storing computer-executable instructions for performing such methods, and computing systems adapted to perform such methods. The innovations described herein further include uses of the results of such classification for prognosis, therapy selection and/or other purposes, as well as arrays and kits that provide the values quantifying expression levels of signature genes as input to classification.

Various alternatives to the examples described herein are possible. For example, any of the methods described herein can be altered by changing the ordering of the method acts described, by splitting, repeating, or omitting certain method acts, etc. The various aspects of the disclosed technology can be used in combination or separately. Different embodiments use one or more of the described innovations. Some of the innovations described herein address one or more of the problems noted in the background. Typically, a given technique/tool does not solve all such problems.

Methods of Subtyping DLBCL

Disclosed herein are methods of determining a subtype of DLBCL (e.g., GCB or non-GCB (such as ABC) subtypes) based on gene expression for two or more genes (such as two or more DLBCL signature genes) in a sample from a subject with DLBCL. In general, the expression data for each evaluated signature gene is assigned a value (for example based or represented as a proportional quantity out of total reads for a given sample). The values assigned to the evaluated signature genes are weighted and combined to provide a score (or probability score). A subtype of DLBCL is then determined (e.g., a call of GCB or non-GCB) from the score based on cutoffs, thresholds, or other criteria In one example, the disclosure provides methods for classifying a diffuse large B-cell lymphoma (DLBCL). Such methods can include directly or indirectly detecting or measuring expression (such as nucleic acid expression or protein expression) of a plurality of DLBCL signature genes, such as at least two of, at least three of, at least four of, or all of CD47, CD86, IL16, NF2, PIM1, PTPRC, REL, STAT3, TNFRSF8, and TYMS, or at least two of, at least three of, at least four of or all of CD47, CD86, ENTPD1, FOXP1, FUT8, IL16, ITPKB, LRMP, MME, NF2, PIM1, PTPRC, REL, STAT3, TNFRSF8, and TYMS, in a sample (such as a fixed, e.g., FFPE, sample) obtained from a subject. Thus, an expression value (which can be quantitative) for each DLBCL signature gene, such as an expression value for at least two of (or all of) CD47, CD86, IL16, NF2, PIM1, PTPRC, REL, STAT3, TNFRSF8, or for at least two of (or all of) CD47, CD86, ENTPD1, FOXP1, FUT8, IL16, ITPKB, LRMP, MME, NF2, PIM1, PTPRC, REL, STAT3, TNFRSF8, and TYMS, is obtained. The resulting expression value for each DLBCL signature gene can be weighted (for example by multiplying by a coefficient value, such as those shown in Table 5), thereby generating at least two weighted expression values. The resulting weighted expression values are summed or added, thereby generating a summed weighted expression value. The summed weighted expression value is used (e.g., in a probabilistic model) to calculate a probability score, which is compared to thresholds or cut-off values. In one example, calculating a probability score uses the formula $$Pr(Y=y|x) = \frac{e^{(\beta_0 + x^T\beta)}}{1 + e^{(\beta_0 + x^T\beta)}} \quad \text{(Equation 1)}$$

wherein β0 is a constant, β is the weight for a signature gene (such as one in Table 1), and $x^T$ is the value for such signature gene. In one example, the DLBCL sample is classified as activated B-cell-like (ABC) when the probability score is below the established score for ABC, as germinal center B-cell-like (GCB) when the probability score is above the cutoff established for GCB; or as unclassified when the probability score is a value in a range of scores for unclassified, which, typically, is between and inclusive of the cutoff score for ABC and the cutoff score for GBC.

In some examples, expression of nucleic acid molecules are measured, such as mRNA. In some examples, expression of protein molecules are measured. Expression measurements in some examples are quantitative or semi-quantitative. In some examples, measuring expression utilizes sequencing, and wherein the expression value for each DLBCL signature gene is a count representing a number (relative or absolute) of target nucleic acids (e.g., mRNA)/proteins present in the sample.

In some example, the disclosed methods and DLBCL classifiers classify less than 6% of the samples as unclassified, such as less than 5%, or 4 to 6% as unclassified. In contrast, other DLBCL classifiers (such as those that measure expression of these 12 genes: BCL6, CCND2, ENTPD1, FOXP1, FUT8, IRF4, ITPKB, LMO2, LRMP, MME, MYBL1, and SERPINA9) has a higher rate of unclassified samples, such as at least 10%, at least 11%, or at least 12%, such as 10-12%. Thus, the disclosed DLBCL classifier allows for about 4 to 8% of samples that were unclassifiable by previous methods, to now be classified as ABC or GCB. In some examples, the disclosed methods subtype DLBCL (e.g., as GCB or non-GCB, such as ABC) with an accuracy of at least 90%, such as at least 92%.

In some examples, the methods measure expression using a nuclease based assay. For example, the expression values can be obtained by contacting (e.g., placement in direct physical association) the sample with (1) at least two nuclease protection probes comprising a flanking sequence (NPPF) under conditions sufficient for each NPPF to specifically bind to its target nucleic acid molecule (e.g., DLBCL signature gene), (2) with a nucleic acid molecule including a sequence complementary to the flanking sequence (CFS) under conditions sufficient for the flanking sequence to specifically bind to the CFS, and (3) with a nuclease specific for single-stranded nucleic acid molecules under conditions sufficient to remove unbound nucleic acid molecules. As used herein, conditions sufficient for refers to any environment (e.g., aqueous, including or omitting Na$^+$, Cl$^-$, Mg$^{++}$, Zn$^{++}$, or other specific ion(s), chaotropic agent(s), or surfactant(s), or having a particular concentration of any such ion(s), chaotropic agent(s) or surfactant(s), or having a particular ionic strength, pH, buffer type or concentration, or temperature) that permits the desired activity, for example, that permits specific binding or hybridization between two nucleic acid molecules (such as a probe and a target nucleic acid) or that permits a nuclease to remove (or digest) unbound nucleic acids. This results in a digested sample that includes NPPFs hybridized to the target nucleic acid molecules and to the CFS(s).

Optionally, unbound or single stranded molecules are removed from the sample. The NPPFs hybridized to the target and to the CFSs are amplified with one or more appropriate amplification primers, thereby generating NPPF amplicons. At least a portion of the NPPF amplicons is sequenced (e.g., to determine to which target nucleic acid molecule (e.g., DLBCL signature gene) it was hybridized to). The number of NPPF amplicons can be counted or assigned a value, thereby determining the expression values for each of at least two of (or all of) CD47, CD86, IL16, NF2, PIM1, PTPRC, REL, STAT3, TNFRSF8, or at least two of (or all of) CD47, CD86, ENTPD1, FOXP1, FUT8, IL16, ITPKB, LRMP, MME, NF2, PIM1, PTPRC, REL, STAT3, TNFRSF8, and TYMS in the sample. Thus, the NPPF used in the assay permits the detection, and in some examples quantification, of a target nucleic acid molecule, such as an mRNA.

The disclosed methods can further include administering a therapeutically effective amount of an appropriate therapy, depending on the DLBCL classification. For example, a therapeutically effective amount of (1) a cyclophosphamide, doxorubicin, vincristine, and prednisone or prednisolone (CHOP) chemotherapy, (2) a rituximab plus CHOP (R-CHOP) chemotherapy, or (3) an etoposide plus R-CHOP (R-EPOCH) chemotherapy, can be administered to the subject when the DLBCL is classified as GCB. In another example, a therapeutically effective amount of bendamustine, pixantrone, gemcitabine/oxaliplatin, liposomal vincristine, anti-CD20 mAb, anti-CD22 mAb, anti-CD74 mAb, anti-CD40 mAb, single-chain bispecific anti-CD19 and CD3 mAb construct, I-131 tositumomab (anti-CD20 radioimmunotherapy), Inotuzumab ozogamicin (CMC-544) (CD22 targeted cytotoxic immunoconjugate), 90Y-epratuzumab tetraxetan (radiolabeled humanized anti-CD22 mAb, Brentuximab vedotin (SGN-35) (antitubulin monomethyl auristatin E anti-CD30 mAb conjugate), thalidomide, lenalidomide, Bortezomib (Proteasome inhibitor), NPI-0052 (Proteasome inhibitor), Everolimus (mTOR inhibitor), Temsirolimus (mTOR inhibitor), Vorinostat (Deacetylase inhibitor), Oblimersen sodium (Bcl-2 antisense oligonucleotide), PF-3512676 (TLR9-antagonist), 17-AAG (HSP90 inhibitor), Bevacizumab (Anti-VEGF mAb) Aflibercept (VEGF fusion protein), CAL-101 (PI3K inhibitor), Valproic acid (HDACI), Dinaciclib (CDK1, 2, 5, 9 inhibitor), Fostamatinib (Syk inhibitor), Dasatinib (RTK inhibitor of BCR-ABL, SRC, c-Kit, PDGF and ephrin receptor kinases), Enzastaurin (Protein kinase beta inhibitor), PCI-32765 (Bruton's tyrosine kinase inhibitor), SB1518 (JAK2 inhibitor), Sorafenib (TKI inhibitor of RAF/MEK/ERK/c-kit/Flt3, VEGFRs, PDGFRs, RETR) or any other therapy known in the art (see, e.g., Foon et al., *Adv. Hematology*, Article ID 302570, 2012, doi:10.1155/2012/302570) can be administered to the subject when the DLBCL is classified as ABC or non-GCB.

Also provided are one or more computer-readable storage media storing computer-executable instructions for causing the computing system when programmed thereby to perform the DLBCL classifying methods provided herein. Also provided are computing systems adapted to perform the DLBCL classifying methods provided herein.

Kits useful with the disclosed DLBCL classifying methods are provided. In some examples, such kits have a container that includes at least two different NPPFs and corresponding CFSs, wherein the at least two different NPPFs are specific for two or more of (such as all of) CD47, CD86, IL16, NF2, PIM1, PTPRC, REL, STAT3, or TNFRSF8, or specific for two or more of (such as all of) CD47, CD86, ENTPD1, FOXP1, FUT8, IL16, ITPKB, LRMP, MME, NF2, PIM1, PTPRC, REL, STAT3, TNFRSF8, and TYMS. In some examples, such kits have a container that includes at least two different NPPs, wherein the at least two different NPPs are specific for two or more of (such as all of) CD47, CD86, IL16, NF2, PIM1, PTPRC, REL, STAT3, or TNFRSF8, or specific for two or more of (such as all of) CD47, CD86, ENTPD1, FOXP1, FUT8, IL16, ITPKB, LRMP, MME, NF2, PIM1, PTPRC, REL, STAT3, TNFRSF8, and TYMS. The kits can further include one or more of: a container comprising beads that can specifically bind to amplicons of the at least two different NPPFs; a container comprising a nuclease specific for single-stranded nucleic acids; a container comprising lysis buffer; a container comprising a buffer that can neutralize the nuclease, such as a buffer than can increase the pH above 6; a container comprising wash buffer; a container comprising regents for PCR; a container comprising ethanol; a container comprising denaturation oil; a container comprising a ligation buffer (e.g., one that includes ligase); and a container comprising proteinase K. In some examples, the kit also includes primers specific for a portion of the NPP or NPPF, such as one that can add an experiment tag, and/or sequencing adapter at the 3'- or 5'-end or at both ends of the NPP or NPPF or CSF. In some examples, the kit also includes a computing system that implements a classifier for subtypes of DLBCL, such as software or computer readable medium that receives expression values for two or more DLBCL signature genes, scores the multiple values against corresponding thresholds for each gene, and classifies a sample in a framework that indicates the subtype of DLBCL of the sample.

FIG. 1 shows a generalized method or technique (100) for classifying DLBCL samples. At least some of the acts of the method (100) can be performed by a computing system, such as a special-purpose diagnostic tool, desktop computer, laptop computer, tablet or slate computer, smartphone, or other mobile computing device. Such a computing system can include a reader that receives values that quantify gene expression levels of DLBCL signature genes for a sample (e.g., a network connection, interface to a storage device, user interface for directly receiving user input, or other interface that receives values that quantify gene expression levels), a classifier that scores the gene expression values against thresholds for classification and, based at least in part on results of the scoring, classifies the sample), a data store (e.g., storage that is removable or non-removable, and includes magnetic disks, magnetic tapes or cassettes, CD-ROMs, DVDs, or any other medium which can be used to store information (such as measured gene expression levels of DLBCL signature genes, software for running the classifier, cut-off values) in a non-transitory way and which can be accessed within the computing system), and an output module (e.g., audio output device, display, touchscreen, printer, CD-writer, or another device that provides output from the computing system, such as a determination as to whether the tested sample is ABC, GCB, or unclassified). The architecture can also include a training module that computes thresholds or cut-offs stored in the data store. The classifier can include a data-processor (e.g., to multiply each gene expression value to a particular weight value and provide the weighted values to a score totaller), a score totaller (to sum the calculated weighted values and provide those to the probability module), and a probability module (e.g., to determine the probability of a particular classification using the sum weighted values, and to provide the probability or DLBCL subtype to an output module). For example, the probability module can compare the calculated probability value(s) against corresponding thresholds for ABC, GCB, and unclassified. The classifier gets the probability thresholds/cut off values from the data store, which stores the thresholds for the DLBCL classifier. As a result of the classification, the classifier can provide a summary classification such as non-GCB (e.g., ABC), GCB or unclassified.

Returning to FIG. 1, to start, the system receives (110) (e.g., from a reader or sequencer, and thus may be received from a stored state) multiple values (e.g., relative light units or counts of a detected target or relative or proportional reads) that quantify gene expression levels (e.g., protein and/or mRNA) of multiple DLBCL signature genes, respectively, for a sample. In some examples, gene expression values of two or more of: CD47, CD86, IL16, NF2, PIM1, PTPRC, REL, STAT3, TNFRSF8, and TYMS, such as two or more of CD47, CD86, ENTPD1, FOXP1, FUT8, IL16, ITPKB, LRMP, MME, NF2, PIM1, PTPRC, REL, STAT3, TNFRSF8, and TYMS, are received. The values of gene expression levels for the DLBCL signature genes can be measured for the test sample using any of the approaches described herein or as known to those of ordinary skill in the art. In some examples, the raw data optionally may be "conditioned," for example, a background value may be subtracted from the data and/or the data may be logarithmically transformed (for example, $\log_2$ transformed). The system can optionally normalize the multiple values before scoring using any of the approaches described herein, so long as classification uses the same approach (or similar approach) to normalization as was used during training to determine the thresholds.

For each gene, its expression value is weighted (120), for example by multiplying by a weight value, which reflects the contribution of that gene's expression to the classification of a sample as ABC, GBC or unclassified. Thus, for example, if the weighting of all classifier genes was 1.0 each such genes would have equal weight in the classifier output. Exemplary weight values and their corresponding gene are provided in Table 5. The system sums the weighted gene expression values (130). That is, the weighted value for each gene analyzed is summed, resulting in a weighted sum. The weighted sum is then used (e.g., in a statistical model) to obtain a probability score (140), for example using Equation 1 in Example 1. A computing system that implements the classifier can be used to perform one or more of these tasks.

The probability score is compared against corresponding thresholds for the predicted probability (150) that a sample will be classified as ABC or GBC or neither (i.e., unclassified). The thresholds and rules used for scoring depend on implementation. Example thresholds are described herein, and example scoring rules are described below. Alternatively, the system uses other thresholds and/or other scoring rules. In one example, the cut-offs are 0.43 for the lower point, and 0.57 for the upper point.

Based at least in part on results of the scoring, the system classifies (160) the sample. The rules used for classification depend on implementation. Example classification rules are described below. Alternatively, the system uses other classification rules. In one example, the system classifies a sample as ABC if the predicted probability is <0.43, the system classifies a sample as GCB if the predicted probability is >0.57, and the system classifies a sample as unclassified if the predicted probability is within, and includes, 0.43-0.57.

I. Preparing to Obtain Gene Expression Data

Gene expression is the process by which information encoded in the genome (gene) is transformed (e.g., via transcription and translation processes) into corresponding gene products (e.g., RNA and protein), which function interrelatedly to give rise to a set of characteristics (aka, phenotype). For purposes of this disclosure, gene expression may be measured by any technique known now or in the future. Commonly, gene expression is measured by detecting the products of the genes (e.g., RNA and/or protein) expressed in samples collected from subjects of interest (such as one with DLBCL). Thus, the expression of two or more target genes, such as two or more DLBCL signature genes or markers, can be measured. In one example, gene expression is measured by detecting (e.g., by sequencing) one or more probes that specifically bind to a target mRNA, and determining the number (relative or absolute) number of probes that bound to the mRNA target. Thus, the number of probes detected serves as a measure of gene expression. Examples of DLBCL marker(s) include two or more of: CD47, CD86, IL16, NF2, PIM1, PTPRC, REL, STAT3, TNFRSF8, and TYMS, such as two or more of (such as all of) CD47, CD86, ENTPD1, FOXP1, FUT8, IL16, ITPKB, LRMP, MME, NF2, PIM1, PTPRC, REL, STAT3, TNFRSF8, and TYMS. Other specific examples of DLBCL marker(s) include two or more of (such as 2, 3, 4, 5, 6, 7, 8, 9, or 10 of): CD47, ENTPD1, FOXP1, FUT8, IL16, NF2, PIM1, STAT3, TNFRSF8, and TYMS (which are associated with ABC classification), or two or more of (such as 2, 3, 4, 5, or 6 of) CD86, ITPKB, LRMP, MME, PTPRC, and REL (which are associated with GCB classification). Subjects that can be analyzed with the disclosed methods include human and non-human mammals (e.g., veterinary subjects such as cats, dogs, and mice). In one example, a subject is known or suspected of having a tumor, such as a lymphoma, such as DLBCL.

A. Subjects and Samples

Appropriate samples for use in the methods disclosed herein include any biological sample from the subject that contains cells (e.g., B cells) from the tumor (e.g., a tumor in the lymph nodes, spleen, liver, bone marrow, brain and/or spinal cord) for which information about gene or protein expression (such as those in Table 1) is desired. Samples include those obtained from a subject, such as clinical samples obtained from a subject (including samples from a healthy or apparently healthy human subject or a human patient affected by a condition or disease to be diagnosed or investigated, such as DLBCL, more particularly, ABC or GCB). In one example, the subject is known or suspected to have DLBCL. Exemplary samples may be obtained from normal cells or tissues (e.g., as a control sample), and/or from tumor cells or tissues. In particular examples, a biological sample includes a tumor sample, such as a sample containing lymphoma cells. In one example, a sample includes RNA, such as mRNA. In some embodiments, a sample is from a subject that was previously diagnosed as DLBCL by histology or a clinical method (e.g., IHC or in situ hybridization (ISH)) other than described herein.

The samples of use to determine expression of two or more genes of the disclosed DLBCL signature include any biological specimen that includes nucleic acid (such as genomic DNA, cDNA, viral DNA or RNA, rRNA, tRNA, mRNA, miRNA, oligonucleotides, nucleic acid fragments, modified nucleic acids, synthetic nucleic acids, or the like) or proteins. In some examples, a subject having a lymphoma, such as non-Hodgkin lymphoma (e.g., DLBCL) is selected, for example, to determine a diagnosis or prognosis for the subject or for selection of one or more therapies.

Exemplary samples include, without limitation, cells, cell lysates, blood smears, cytocentrifuge preparations, cytology smears, bodily fluids (e.g., blood, serum, saliva, sputum, urine, etc.), tissue biopsies (e.g., tumor biopsies), lymph node tissue or biopsies, liquid biopsies, fine-needle aspirates, surgical specimens, bone marrow, amniocentesis samples, autopsy material, and/or tissue sections (e.g., cryostat tissue sections and/or paraffin-embedded tissue sections). It will appreciated that any method of obtaining a sample (such as tissue) from a subject can be utilized, and that the selection of the method used will depend upon various factors such as the type of tissue, age of the subject, or procedures available to the practitioner. Standard techniques for acquisition of described samples are available. See, for example Tubbs and Stoler, Cell and Tissue Based Molecular Pathology, Philadelphia: Churchill Livingstone (2009). For example, a sample from a tumor that contains cellular material can be obtained by surgical excision of all or part of the tumor, by collecting a fine needle aspirate from the tumor, as well as other methods known in the art.

The disclosed methods are sensitive and specific and allow detection of target nucleic acid molecules in a sample containing even a limited number of cells. Samples that include small numbers of cells, such as less than 250,000 cells (for example less than 100,000, less than 50,000, less than 10,000, less than 1,000, less than 500, less than 200, less than 100 cells, or less than 10 cells, include but are not limited to, FFPE samples, fine needle aspirates (such as those from lymph or spleen), punch biopsies, needle biopsies, small populations of (e.g., FACS) sorted cells, small numbers of laser captured or macrodissected cells, exosomes and other subcellular particles, or body fluids (such as spinal fluid). For example, a target RNA can be detected in as few as 1000 cells (such as a sample including 1000 or more cells, such as 1000, 2000, 3000, 4000, 5000, 6000, 7000, 8000, 9000, 10,000, 15,000, 20,000, 50,000, or more cells). In some examples, expression of a target RNA can be detected in about 1000 to 100,000 cells, for example about 1000 to 50,000, 1000 to 15,000, 1000 to 10,000, 1000 to 5000, 3000 to 50,000, 6000 to 30,000, or 10,000 to 50,000 cells). In some examples, expression of a target RNA can be detected in about 100 to 250,000 cells, for example about 100 to 100,000, 100 to 50,000, 100 to 10,000, 100 to 5000, 100 to 500, 100 to 200, or 100 to 150 cells. In other examples, expression of a target RNA can be detected in about 1 to 1000 cells (such as about 1 to 500 cells, about 1 to 250 cells, about 1 to 100 cells, about 1 to 50 cells, about 1 to 25 cells, or about 1 cell).

In particular examples, samples are used directly (e.g., fresh or frozen) or can be preserved prior to use, for example, by fixation (e.g., formalin fixation (such as, neutral buffered formalin, zinc formalin and acid formalin), ethanol fixation) and/or by embedding in a solid medium. Embedding media, typically, are inert, able to repel moisture and able to penetrate tissue (e.g., wax, paraffin, celloidin, OCT™ compound, agar, plastics, and acrylics). Some useful samples are formalin-fixed, paraffin-embedded (FFPE) tissue samples. In specific examples, a tissue sample to be analyzed is fixed or, more particularly, fixed and wax- (paraffin-) embedded. The term deparaffinization or dewaxing is refers to the partial or complete removal of any type of embedding medium from a biological sample (for example prior to analysis using the disclosed methods). For example, paraffin-embedded tissue sections can be dewaxed by passage through organic solvents, such as toluene, xylene, limonene, or other suitable solvents. In other examples, paraffin-embedded tissue sections are utilized directly (e.g., without a dewaxing step).

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

A commonly used fixative in preparing tissue or cell samples is formaldehyde, generally in the form of a formalin solution (4% formaldehyde in a buffer solution, referred to as 10% buffered formalin). In one example, the fixative is 10% neutral buffered formalin.

Some samples, including fixed (e.g., FFPE) tissues or cells, may be prepared by suspending the sample in a suitable solution (e.g., as described in Examples that follow) without any purification and/or reverse transcription of mRNA present in such sample. All or part (e.g., a pre-measured area or volume) of a sample affixed to a solid surface (e.g., a microscope slide) may be scraped directly into a suitable solution with gentle mixing (e.g., using a pipettor) to disperse and/or break up large pieces of the sample and create a suspension comprising cellular materials that largely remain suspended at least for a period during which the suspension is contacted with suitable reagents. In some embodiments, mRNA in the sample may (but need not) be partially degraded or it is of little concern if some incomplete degradation of mRNA in the sample has occurred.

In some embodiments, a sample is a lysate of cells and/or tissue obtained from a tumor or tissue. Cell lysate contains many of the proteins and nucleic acids contained in a cell, and include for example, the biomarkers shown in Table 1. Methods for obtaining or preparing a cell lysate are well known in the art and can be found for example in Ausubel et al. (In Current Protocols in Molecular Biology, John Wiley & Sons, New York, 1998). In some examples, cells in the sample are lysed or permeabilized in an aqueous solution (for example using a lysis buffer). The aqueous solution or lysis buffer may include detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 8% to 60% formamide (v/v) about 0.01% to 0.5% SDS, and about 0.5-6×SSC (for example, about 3×SSC). The buffer may optionally include tRNA at about 0.001 to about 2.0 mg/ml or a ribonuclease; DNAase; proteinase K; enzymes (e.g. collagenase or lipase) that degrade protein, matrix, carbohydrate, lipids, or one species of oligonucleotides, or combinations thereof. The lysis buffer may also include a pH indicator, such as Phenol Red. Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 50° C. to about 95° C. or about 65° C. to about 100° C.) to lyse or permeabilize the cell. In some examples, lysis is performed at about 50° C., 65° C., or 95° C., for example if the nucleic acid to be detected is RNA. In other examples, lysis is performed at about 105° C., for example if the nucleic acid to be detected is DNA. In some examples, lysis conditions can be such that genomic DNA is not accessible to the probes whereas RNA (for example, mRNA). In some examples, the crude cell lysis is used directly without further purification.

In some examples, a tissue or cell sample is applied to a substrate and analyzed to determine presence of one or more target nucleic acids. A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

A target (such as RNA) can be isolated or extracted from the sample, thereby purifying it away from other non-target biological components in a sample. However, such as step is optional. Purification refers to separating the target from one or more extraneous components also found in a sample. For example, prior to PCR-based detection of mRNA with paired target-specific primers, total or soluble mRNA (including the target mRNA) often is separated from cell proteins and other nucleic acids in the sample. Components that are isolated, extracted or purified from a mixed specimen or sample typically are enriched by at least 50%, at least 60%, at least 75%, at least 90%, or at least 98% or even at least 99% compared to the unpurified or non-extracted sample.

In some examples, nucleic acid molecules in the sample are amplified, for example using PCR (e.g., real time RT-PCR), prior to their analysis. In one example, a quantitative PCR method is used.

B. Control Samples

Control samples can be used in parallel with disclosed methods, and can include any suitable control sample against which to compare expression of a biomarker shown in Table 1. In some embodiments, the control sample is non-tumor tissue, such as a plurality of non-tumor tissue samples. In one example, non-tumor tissue is tissue known to be benign, such as histologically normal lymphoid tissue. In some examples, non-tumor tissue includes a lymphoid or bone marrow sample that appears normal; that is, it has the absence of cellular dysplasia or other known disease (e.g., lymphoma, such as DLBCL) indicators. In some examples, the non-tumor tissue is obtained from the same subject, such as non-tumor tissue that is adjacent or even distant from a lymphoid malignancy (such as DLBCL). In other examples, the non-tumor tissue is obtained from a healthy control subject or several healthy control subjects. For example, non-tumor tissue can be obtained from a plurality of healthy control subjects (e.g., those not having any cancers, including lymphoma cancer (e.g., DLBCL), such as samples containing normal cells or tissues (for example from the lymph nodes, spleen, liver, bone marrow, brain and/or spinal cord) from a plurality of such subjects. In some embodiments, one or more (e.g., a plurality of) control samples are used to obtain a reference (e.g., normal control) value or ranges of values for expression levels of the biomarkers shown in Table 1. In some embodiments, a reference value obtained from control samples may be a population central tendency (such as a mean, median or average), or reference range of values such as ±0.5, 1.0, 1.5 or 2.0 standard deviation(s) around a population central tendency.

C. Sample Analytical Options

Some method embodiments use fixed samples (e.g., FFPE tissue samples). Fixation techniques may vary from site-to-site, country-to-country, investigator-to-investigator, etc. (Dissecting the Molecular Anatomy of Tissue, ed. by Emmert-Buck, Gillespie and Chuaqui, New York: Springer-Verlag, 244 pages (2010)) and may affect the integrity of and/or accessibility to the gene product(s) to be detected. In some such methods (e.g., involving PCR), RNA recovery (e.g., using reversible cross linking agents, ethanol-based fixatives and/or RNA extraction or purification (in whole or in part)) may be advantageous; while, in other representative methods (e.g., involving qNPA or qNPS) RNA recovery is optional or RNA recovery expressly is not needed. Similarly, tissue conditioning can be used to recover protein gene products from fixed tissue and, thereby, aid in the detection of such protein products.

The percentage of tumor (e.g., DLBCL) in biological samples may vary; thus, in some disclosed embodiments, at least 5%, at least 10%, at least 25%, at least 50%, at least 75%, at least 80% or at least 90% of the sample area (or sample volume) or total cells in the sample are tumor (e.g., DLBCL). In other examples, samples may be enriched for tumor cells, e.g., by macrodissecting areas or cells from a sample that are or appear to be predominantly tumor (e.g., DLBCL). Optionally, a pathologist or other appropriately trained professional may review the sample (e.g., H&E-stained tissue section) to determine if sufficient tumor is present in the sample for testing and/or mark the area (e.g., most dense tumor area) to be macrodissected. In specific examples, macrodissection of tumor (e.g., DLBCL) avoids as much as possible necrotic and/or hemorrhagic areas. Samples useful in some disclosed methods will have less than 25%, 15%, 10%, 5%, 2%, or 1% necrosis by sample volume or area or total cells.

Sample load may influence the amount and/or concentration of gene product (e.g., the biomarkers in Table 1) available for detection. In particular embodiments, at least 1 ng, 10 ng, 100 ng, 1 ug, 10 ug, 100 ug, 500 ug, 1 mg total RNA, at least 1 ng, 10 ng, 100 ng, 1 ug, 10 ug, 100 ug, 500 ug, 1 mg total DNA, or at least 0.01 ng, 0.1 ng, 1 ng, 10 ng, 100 ng, 1 ug, 10 ug, 100 ug, 500 ug, or 1 mg total protein is isolated from and/or present in a sample (such as a sample lysate). Some embodiments use tissue samples (e.g., FFPE lymph nodes, spleen, liver, bone marrow, brain and/or spinal cord tissues) that are at least 3, 5, 8, or 10 μm (e.g., about 3 to about 10 μm) thick and/or at least 0.15, 0.2, 0.5, 1, 1.5, 2, 5 or 10 cm$^2$ in area. The concentration of sample suspended in buffer in some method embodiments is at least 0.006 cm$^2$/ul (e.g., 0.15 cm$^2$ FFPE tissue per 25 uL of buffer (e.g., lysis buffer)).

II. Genes and Gene Sets

Among the innovations disclosed herein are genes (also referred to as biomarkers) and sets of genes (also referred to as gene signatures) useful for distinguishing subtypes of DLBCL. In particular embodiments, genes and gene sets are disclosed for subtyping ABC and GCB DLBCL (see Table 1). The expression of such genes and sets of genes are useful in classifiers of DLBCL and algorithms, and/or to design analyte-specific reagents (e.g., nucleic acid probes or antibodies) for arrays or other disclosed compositions.

In some embodiments, determining the level of expression in a biological sample (such as a tumor biopsy) includes detecting two or more gene products (e.g., RNA or protein) shown in Table 1, for example by determining the relative or actual amounts of such nucleic acids (or proteins) in the sample, as described herein.

A. DLBCL Signature Genes

Exemplary DLBCL signature genes include those shown in Table 1. In some embodiments, the DLBCL gene signature includes two or more of: CD47, CD86, IL16, NF2, PIM1, PTPRC, REL, STAT3, TNFRSF8, and TYMS (such as at least 2, at least 3, at least 4, at least 5, at least 6, at least 7, at least 8, at least 9 or all 10 of these), such as two or more of CD47, CD86, ENTPD1, FOXP1, FUT8, IL16, ITPKB, LRMP, MME, NF2, PIM1, PTPRC, REL, STAT3, TNFRSF8, and TYMS (such as at least 2, at least 3, at least 4, at least 5, at least 6, at least 7, at least 8, at least 9, at least 10, at least 11, at least 12, at least 13, at least 14, at least 15, or all 16 of these).

TABLE 1

Exemplary DLBCL markers that allow for classification of GCB and non-GCB subtypes

| Gene | GenBank ® Accession Nos. |
| --- | --- |
| CD47 | NM_001777.3, NM_198793.2, LN680437.1 |
| CD86 | NM_175862.4, NG_029928.1, NM_176892.1, NM_001206924.1, NM_001206925.1 |
| ENTPD1 (CD39) | NM_001776.5; NM_001098175.1; NM_001164178.1; NM_001164179.1; NM_001164181.1; NM_001164182.1; NM_001164183.1 |
| FOXP1 | NM_001012505.1; NM_032682.5; NM_001244808.1; NM_001244812.1; NM_001244814.1; NM_001244815.1, NM_001244813.1; NM_001244810.1; NM_001244816.1 |
| FUT8 | NM_178155.2, NM_004480.4, NM_178156.2, NR_038167.1, NR_038170.1 |
| IL16 | NM_004513.5, NM_172217.3, NM_001172128.1, XM_011521520.1, XR_931805.1 |
| ITPKB | NM_022221.3; XM_005273120.1 |
| LRMP | NM_006152.3, NM_001204127.1, NM_001204126.1, XM_006719076.2, XM_011520668.1, XM_011520669.1 XM_005253374.2, XM_011520670.1 |
| MME (CD10) | NM_000902.3, NM_007287.2, NM_007288.2, BC143465.1, NM_007289.2 |
| NF2 | NM_000268.3, NM_016418.5, NM_181828.2, NM_181831.2 |
| PIM1 | NM_001243186.1, M24779.1, NM_002648.3 |
| PTPRC | NM_002838.4, NM_080921.3, NR_052021.1, NM_001267798.1 |
| REL | NM_002908.3, NM_001291746.1, DQ314888.1 |
| STAT3 | NM_139276.2, NM_003150.3, NM_213662.1, NG_007370.1 |
| TNFRSF8 | NM_001243.4, XM_011542442.1, XM_011542444.1, XM_011542443.1, AY498860.1 |
| TYMS | NM_001071.2; NG_028255.1 |

Cluster of differentiation 47 (CD47) (e.g., OMIM 601028), also known as integrin associated protein, is a transmembrane protein that partners with membrane integrins and also binds the ligands thrombospondin-1 and signal-regulatory protein alpha. Transcript variants (e.g., alternatively spliced transcripts) have been identified for this gene. Nucleic acid and protein sequences for CD47 are publicly available. For example, GenBank® Accession Nos. NM_001777.3, NM_198793.2, and LN680437.1 disclose exemplary human CD47 nucleic acid sequences, and GenBank® Accession Nos. NP_001768.1, NP_942088.1, and CEJ95640.1 disclose exemplary human CD47 protein sequences. One skilled in the art will appreciate that variants of such CD47 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any CD47 GenBank® Accession No. provided herein.

Cluster of differentiation 86 (CD86) (e.g., OMIM 601020), also known as B7-2, is expressed on antigen-presenting cells and provides costimulatory signals for T cell activation and survival. Transcript variants (e.g., alternatively spliced transcripts) have been identified for this gene. Nucleic acid and protein sequences for CD86 are publicly available. For example, GenBank® Accession Nos. NM_175862.4, NG_029928.1, NM_176892.1, NM_001206924.1, and NM_001206925.1 disclose exemplary human CD86 nucleic acid sequences, and GenBank® Accession Nos. NP_787058.4, NP_008820.3, NP_795711.1, NP_001193853.1, and NP_001193854.1 disclose exemplary human CD86 protein sequences. One skilled in the art will appreciate that variants of such CD86 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any CD86 GenBank® Accession No. provided herein.

Ectonucleoside triphosphate diphosphohydrolase 1 (ENTPD1) (e.g., OMIM 601752), also known as CD39, ATPDase, and NTPDase-1, is an enzyme (EC 3.6.1.5) that hydrolyzed ATP and ADP to AMP, initiating generation of adenosine. ENTPD1 is widely expressed, including in blood vessels and cells of the immune system. Transcript variants (e.g., alternatively spliced transcripts) have been identified for this gene. Nucleic acid and protein sequences for ENTPD1 are publicly available. For example, GenBank® Accession Nos. NM_001776.5; NM_001098175.1; NM_001164178.1; NM_001164179.1; NM_001164181.1; and NM_001164182.1; NM_001164183.1 disclose exemplary human ENTPD1 nucleic acid sequences, and GenBank® Accession Nos. AAH47664.1, NP_001091645.1, NP_001157650.1, NP_001157653.1, NP_001767.3, NP_001157651.1, NP_001157654.1, and NP_001157655.1 disclose exemplary human ENTPD1 protein sequences. One skilled in the art will appreciate that variants of such ENTPD1 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any ENTPD1 GenBank® Accession No. provided herein.

Forkhead box protein P1 (FOXP1) (e.g., OMIM 605515), is a transcription factor containing DNA-binding and protein-protein binding domains, which functions as a transcription repressor. FOXP1 regulates a variety of important aspects of development including tissue development of: the lungs, brain, thymus and heart. Transcript variants (e.g., alternatively spliced transcripts) have been identified for this gene. Nucleic acid and protein sequences for Foxp1 are publicly available. For example, GenBank® Accession Nos. NM_001012505.1; NM_032682.5; NM_001244808.1; NM_001244812.1; NM_001244814.1; NM_001244815.1, NM_001244813.1; NM_001244810.1 and NM_001244816.1 disclose exemplary human Foxp1 nucleic acid sequences, and GenBank® Accession Nos. AAG47632.1, NP_001231743.1; NP_001012523.1; NP_001231737.1, NP_001231739.1, NP_001231741.1, NP_001231742.1, and NP_001231744.1, disclose exemplary human Foxp1 protein sequences. One skilled in the art will appreciate that variants of such Foxp1 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any Foxp1 GenBank® Accession No. provided herein.

Fucosyltransferase 8 (alpha (1,6) fucosyltransferase) (FUT8) (e.g., OMIM 602589), also known as GDP-L-Fuc: N-acetyl-beta-D-glucosaminide alpha 1,6-fucosyltransferase; GDP-fucose-glycoprotein fucosyltransferase; abd alpha-(1,6)-fucosyltransferase, is an enzyme (EC 2.4.1.68) which catalyzes transfer of fucose from GDP-fucose to N-linked type complex glycopeptides. Transcript variants (e.g., alternatively spliced transcripts) and non-coding RNAs have been identified for this gene. Nucleic acid and protein sequences for FUT8 are publicly available. For example, GenBank® Accession Nos. NM_178155.2, NM_004480.4, NM_178156.2, NR_038167.1, and NR_038170.1 disclose exemplary human FUT8 nucleic acid sequences, and GenBank® Accession Nos. AAI42959.1, NP_835368.1, NP_004471.4, and NP_835369.1 disclose exemplary human FUT8 protein sequences. One skilled in the art will appreciate that variants of such FUT8 sequences can be used to classify a DLBCL, such as those whose expression is altered in DLBCL (for example in ABC and/or GCB) such as a sequence having at least 90%, at least 95%, at least 96%, at least 97%, at least 98% or at least 99% sequence identity to any FUT8 GenBank® Accession No. provided herein.

Interleukin 16 (IL16) (e.g., OMIM 603035) is a cytokine that functions as a chemoattractant for some immune cells expressing CD4. Transcript variants (e.g., alternatively spliced transcripts) have been identified for this gene. Nucleic acid and protein sequences for IL16 are publicly available. For example, GenBank® Accession Nos. NM_004513.5, NM_172217.3, NM_001172128.1, XM_011521520.1, and XR_931805.1 disclose exemplary human IL16 nucleic acid sequences, and GenBank® Accession Nos. AAI36661.1, AAD15990.1, NP_001165599.1, ACI00236.1, and XP_011519821.1 disclose exemplary human IL16 protein sequences. One skilled in the art will appreciate that variants of such IL16 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any IL16 GenBank® Accession No. provided herein.

Inositol 1,4,5-trisphosphate 3-kinase B (ITPKB) (e.g., OMIM 147522), also known as IP3 3-kinase B, IP3K B, and proliferation-inducing protein 37, phosphorylates inositol 1,4,5-triphosphosate to Ins(1,3,4,5)P4. Nucleic acid and protein sequences for ITPKB are publicly available. Transcript variants (e.g., alternatively spliced transcripts) have been identified for this gene. For example, GenBank® Accession No. NM_002221.3 and XM_005273120.1 disclose exemplary human ITPKB nucleic acid sequences, and GenBank® Accession Nos. NP_002212.3 and AAH15009.1 disclose exemplary human ITPKB protein sequences. One skilled in the art will appreciate that variants of such ITPKB sequences can be used to classify a DLBCL, such as those whose expression is altered in DLBCL (for example in ABC and/or GCB) such as a sequence having at least 90%, at least 95%, at least 96%, at least 97%, at least 98% or at least 99% sequence identity to any ITPKB GenBank® Accession No. provided herein.

Lymphoid-restricted membrane protein (LRMP) (e.g., OMIM 602003), also known as JAW1, is expressed in lymphoid cell lines and tissues. Transcript variants (e.g., alternatively spliced transcripts) have been identified for this gene. Nucleic acid and protein sequences for LRMP are publicly available. For example, GenBank® Accession Nos. NM_006152.3, NM_001204127.1, NM_001204126.1, XM_006719076.2, XM_011520668.1, XM_011520669.1 XM_005253374.2, and XM_011520670.1 disclose exemplary human LRMP nucleic acid sequences, and GenBank® Accession Nos. NP_006143.2, NP_001191056.1, XP_011518971.1, XP_011518972.1, Q12912.3, and NP_001191055.1 disclose exemplary human LRMP protein sequences. One skilled in the art will appreciate that variants of such LRMP sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any LRMP GenBank® Accession No. provided herein.

Membrane metallo-endopeptidase (MME) (e.g., OMIM 120520), also known as CD10, atriopeptidase, common acute lymphocytic leukemia antigen, enkephalinase, neprilysin, and neutral endopeptidase, is a neutral endopeptidase (EC 3.4.24.11) that cleaves peptides at the amino side of hydrophobic residues and inactivates several peptide hormones including glucagon, enkephalins, substance P, neurotensin, oxytocin, and bradykinin. Transcript variants (e.g., alternatively spliced transcripts) have been identified for this gene. Nucleic acid and protein sequences for MME are publicly available. For example, GenBank® Accession Nos. NM_000902.3, NM_007287.2, NM_007288.2, BC143465.1, and NM_007289.2 disclose exemplary human MME nucleic acid sequences, and GenBank® Accession Nos. AAI43466.1, AAI01659.1, NP_000893.2, NP_009218.2, NP_009219.2, and NP_009220.2 disclose exemplary human MME protein sequences. One skilled in the art will appreciate that variants of such MME sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any MME GenBank® Accession No. provided herein.

Neurofibromin 2 (NF2) (e.g., OMIM 607379), also known as merlin, is a cytoskeletal protein having tumor suppressor properties. Transcript variants (e.g., alternatively spliced transcripts) have been identified for this gene. Nucleic acid and protein sequences for NF2 are publicly available. For example, GenBank® Accession Nos. NM_000268.3, NM_016418.5, NM_181828.2, and NM_181831.2 disclose exemplary human NF2 nucleic acid sequences, and GenBank® Accession Nos. NP_000259.1, NP_057502.2, NP_861966.1, and NP_861969.1 disclose exemplary human NF2 protein sequences. One skilled in the art will appreciate that variants of such NF2 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any NF2 GenBank® Accession No. provided herein.

Proto-oncogene serine/threonine-protein kinase Pim-1 (PIM1) (e.g., OMIM 164960), is a proto-oncogene involved in cytokine signaling. Transcript variants (e.g., alternatively spliced transcripts) have been identified for this gene. Nucleic acid and protein sequences for PIM1 are publicly available. For example, GenBank® Accession Nos. NM_001243186.1, M24779.1, and NM_002648.3 disclose exemplary human PIM1 nucleic acid sequences, and GenBank® Accession Nos. NP_001230115.1, NP_002639.1, and AAH20224.1 disclose exemplary human PIM1 protein sequences. One skilled in the art will appreciate that variants of such PIM1 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any PIM1 GenBank® Accession No. provided herein.

Protein tyrosine phosphatase, receptor type, C (PTPRC) (e.g., OMIM 151460), also referred to as CD45, is an enzyme (EC 3.1.3.48) expressed in hematopoietic cells that regulates T- and B-cell antigen receptor signaling. Transcript variants (e.g., alternatively spliced transcripts) have been identified for this gene. This gene contains 34 exons and three exons of the primary transcripts are alternatively spliced to generate up to eight different mature mRNAs and after translation eight different protein products. These three exons generate the RA, RB and RC isoforms. Nucleic acid and protein sequences for PTPRC are publicly available. For example, GenBank® Accession Nos. NM_002838.4, NM_080921.3, NR_052021.1 and NM_001267798.1 disclose exemplary human PTPRC nucleic acid sequences, and GenBank® Accession Nos. NP_002829.3, NP_563578.2, P08575.2 and NP_001254727.1 disclose exemplary human PTPRC protein sequences. One skilled in the art will appreciate that variants of such PTPRC sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any PTPRC GenBank® Accession No. provided herein.

v-rel avian reticuloendotheliosis viral oncogene homolog (REL) (e.g., OMIM 164910), is a transcription factor containing a Rel homology domain, and plays a role in B-cell survival and proliferation. The REL gene is amplified or mutated in DLBCL. Transcript variants (e.g., alternatively spliced transcripts) have been identified for this gene. Nucleic acid and protein sequences for REL are publicly available. For example, GenBank® Accession Nos. NM_002908.3, NM_001291746.1, and DQ314888.1 disclose exemplary human REL nucleic acid sequences, and GenBank® Accession Nos. NP_002899.1, NP_001278675.1, and AAI43886.1 disclose exemplary human REL protein sequences. One skilled in the art will appreciate that variants of such REL sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any REL GenBank® Accession No. provided herein.

Signal transducer and activator of transcription (STAT3) (e.g., OMIM 102582), is a transcription activator, which can have an oncogenic or a tumor suppressor role depending upon the genetic background of the tumor. Transcript variants (e.g., alternatively spliced transcripts) have been identified for this gene. Nucleic acid and protein sequences for STAT3 are publicly available. For example, GenBank® Accession Nos. NM_139276.2, NM_003150.3, NM_213662.1, and NG_007370.1 disclose exemplary human STAT3 nucleic acid sequences, and GenBank® Accession Nos. NP_644805.1, NP_003141.2, and NP_998827.1 disclose exemplary human STAT3 protein sequences. One skilled in the art will appreciate that variants of such STAT3 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any STAT3 GenBank® Accession No. provided herein.

Tumor necrosis factor receptor superfamily, member 8 (TNFRSF8) (e.g., OMIM 153243), also known as CD30, is expressed by activated T and B cells. Transcript variants (e.g., alternatively spliced transcripts) have been identified for this gene. Nucleic acid and protein sequences for TNFRSF8 are publicly available. For example, GenBank® Accession Nos. NM_001243.4, XM_011542442.1, XM_011542444.1, XM_011542443.1, and AY498860.1 disclose exemplary human TNFRSF8 nucleic acid sequences, and GenBank® Accession Nos. NP_001234.3, XP_011540746.1, and NP_001268359.2 disclose exemplary human TNFRSF8 protein sequences. One skilled in the art will appreciate that variants of such TNFRSF8 sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any TNFRSF8 GenBank® Accession No. provided herein.

Thymidylate synthetase (TYMS) (e.g., OMIM 188350) is an enzyme (EC 2.1.1.45) that catalyzes the conversion of deoxyuridine monophosphate (dUMP) to deoxythymidine monophosphate (dTMP). Transcript variants (e.g., alternatively spliced transcripts) have been identified for this gene. Nucleic acid and protein sequences for TYMS are publicly available. For example, GenBank® Accession Nos. NM_001071.2 and NG_028255.1 disclose exemplary human TYMS nucleic acid sequences, and GenBank® Accession Nos. NP_001062.1, EAX01716.1, and EAX01717.1 disclose exemplary human TYMS protein sequences. One skilled in the art will appreciate that variants of such TYMS sequences can be used to classify a DLBCL, such as those whose expression is altered in DLBCL (for example in ABC and/or GCB), such as a sequence having at least 90%, at least 95%, at least 96%, at least 97%, at least 98% or at least 99% sequence identity to any TYMS GenBank® Accession No. provided herein.

Specific embodiments useful for subtyping DLBCL, include, without limitation, determining or measuring expression of:

a. one or more (e.g., at least or fixed at two, three, four, five, six, seven, eight, nine, or 10) of CD47, CD86, IL16, NF2, PIM1, PTPRC, REL, STAT3, TNFRSF8, and TYMS;

b. all of CD47, CD86, IL16, NF2, PIM1, PTPRC, REL, STAT3, TNFRSF8, and TYMS;

c. one or more (e.g., at least or fixed at two, three, four, five, six, seven, eight, nine, 10, 11, 12, 13, 14, 15, or 16) of CD47, CD86, ENTPD1, FOXP1, FUT8, IL16, ITPKB, LRMP, MME, NF2, PIM1, PTPRC, REL, STAT3, TNFRSF8, and TYMS;

d. one or more (e.g., at least or fixed at two, three, four, five, six, seven, eight, nine, or 10) of CD47, CD86, ENTPD1, FOXP1, FUT8, IL16, ITPKB, LRMP, MME, NF2, PIM1, PTPRC, REL, STAT3, TNFRSF8, and TYMS;

e. one or more (e.g., at least or fixed at two, three, four, five, or six) of CD86, ITPKB, LRMP, MME, PTPRC, and REL;

f. any gene set comprising or consisting of any one or any two (to the extent not duplicative) of the following two-gene combinations: {CD47,CD86} {CD47,IL16} {CD47,NF2} {CD47,PIM1} {CD47,PTPRC} {CD47, REL} {CD47,STAT3} {CD47,TNFRSF8} {CD47, TYMS} {CD86,IL16} {CD86,NF2} {CD86,PIM1} {CD86,PTPRC} {CD86,REL} {CD86,STAT3} {CD86,TNFRSF8} {CD86,TYMS} {IL16,NF2} {IL16,PIM1} {IL16,PTPRC} {IL16,REL} {IL16, STAT3} {IL16,TNFRSF8} {IL16,TYMS} {NF2, PIM1} {NF2,PTPRC} {NF2,REL} {NF2,STAT3} {NF2,TNFRSF8} {NF2,TYMS} {PIM1,PTPRC} {PIM1,REL} {PIM1,STAT3} {PIM1,TNFRSF8} {PIM1,TYMS} {PTPRC,REL} {PTPRC,STAT3} {PTPRC,TNFRSF8} {PTPRC,TYMS} {REL,STAT3} {REL,TNFRSF8} {REL,TYMS} {STAT3,TNFRSF8} {STAT3,TYMS} {TNFRSF8,TYMS};

g. any gene set comprising or consisting of any one or any two (to the extent not duplicative) of the following three-gene combinations: {CD47,CD86,IL16} {CD47, CD86,NF2} {CD47,CD86,PIM1} {CD47,CD86,PT-PRC} {CD47,CD86,REL} {CD47,CD86,STAT3} {CD47,CD86,TNFRSF8} {CD47,CD86,TYMS} {CD47,IL16,NF2} {CD47,IL16,PIM1} {CD47,IL16, PTPRC} {CD47,IL16,REL} {CD47,IL16,STAT3} {CD47,IL16,TNFRSF8} {CD47,IL16,TYMS} {CD47,NF2,PIM1} {CD47,NF2,PTPRC} {CD47,NF2,REL} {CD47,NF2,STAT3} {CD47,NF2,TNFRSF8} {CD47,NF2,TYMS} {CD47,PIM1,PTPRC} {CD47,PIM1,REL} {CD47,PIM1,STAT3} {CD47,PIM1,TNFRSF8} {CD47,PIM1,TYMS} {CD47,PTPRC,REL} {CD47,PTPRC,STAT3} {CD47,PTPRC,TNFRSF8} {CD47,PTPRC,TYMS} {CD47,REL,STAT3} {CD47,REL,TNFRSF8} {CD47,REL,TYMS} {CD47,STAT3,TNFRSF8} {CD47,STAT3,TYMS} {CD47,TNFRSF8,TYMS} {CD86,IL16,NF2} {CD86,IL16,PIM1} {CD86,IL16,PTPRC} {CD86,IL16,REL} {CD86,IL16,STAT3} {CD86,IL16,TNFRSF8} {CD86,IL16,TYMS} {CD86,NF2,PIM1} {CD86,NF2,PTPRC} {CD86,NF2,REL} {CD86,NF2,STAT3} {CD86,NF2,TNFRSF8} {CD86,NF2,TYMS} {CD86,PIM1,PTPRC} {CD86,PIM1,REL} {CD86,PIM1,STAT3} {CD86,PIM1,TNFRSF8} {CD86,PIM1,TYMS} {CD86,PTPRC,REL} {CD86,PTPRC,STAT3} {CD86,PTPRC,TNFRSF8} {CD86,PTPRC,TYMS} {CD86,REL,STAT3} {CD86,REL,TNFRSF8} {CD86,REL,TYMS} {CD86,STAT3,TNFRSF8} {CD86,STAT3,TYMS} {CD86,TNFRSF8,TYMS} {IL16,NF2,PIM1} {IL16,NF2,PTPRC} {IL16,NF2,REL} {IL16,NF2,STAT3} {IL16,NF2,TNFRSF8} {IL16,NF2,TYMS} {IL16,PIM1,PTPRC} {IL16,PIM1,REL} {IL16,PIM1,STAT3} {IL16,PIM1,TNFRSF8} {IL16,PIM1,TYMS} {IL16,PTPRC,REL} {IL16,PTPRC,STAT3} {IL16,PTPRC,TNFRSF8} {IL16,PTPRC,TYMS} {IL16,REL,STAT3} {IL16,REL,TNFRSF8} {IL16,REL,TYMS} {IL16,STAT3,TNFRSF8} {IL16,STAT3,TYMS} {IL16,TNFRSF8,TYMS} {NF2,PIM1,PTPRC NF2,PIM1,REL} {NF2,PIM1,STAT3} {NF2,PIM1,TNFRSF8} {NF2,PIM1,TYMS} {NF2,PTPRC,REL} {NF2,PTPRC,STAT3} {NF2,PTPRC,TNFRSF8} {NF2,PTPRC,TYMS} {NF2,REL,STAT3} {NF2,REL,TNFRSF8} {NF2,REL,TYMS} {NF2,STAT3,TNFRSF8} {NF2,STAT3,TYMS} {NF2,TNFRSF8,TYMS} {PIM1,PTPRC,REL} {PIM1,PTPRC,STAT3} {PIM1,PTPRC,TNFRSF8} {PIM1,PTPRC,TYMS} {PIM1,REL,STAT3} {PIM1,REL,TNFRSF8} {PIM1,REL,TYMS} {PIM1,STAT3,TNFRSF8} {PIM1,STAT3,TYMS} {PIM1,TNFRSF8,TYMS} {PTPRC,REL,STAT3} {PTPRC,REL,TNFRSF8} {PTPRC,REL,TYMS} {PTPRC,STAT3,TNFRSF8} {PTPRC,STAT3,TYMS} {PTPRC,TNFRSF8,TYMS} {REL,STAT3,TNFRSF8} {REL,STAT3,TYMS} {REL,TNFRSF8,TYMS} STAT3,TNFRSF8,TYMS;

h. any gene set comprising or consisting of any one or any two (to the extent not duplicative) of the following four-gene combinations: {CD47,CD86,IL16,NF2} {CD47,CD86,IL16,PIM1} {CD47,CD86,IL16,PTPRC} {CD47,CD86,IL16,REL} {CD47,CD86,IL16,STAT3} {CD47,CD86,IL16,TNFRSF8} {CD47,CD86,IL16,TYMS} {CD47,CD86,NF2,PIM1} {CD47,CD86,NF2,PTPRC} {CD47,CD86,NF2,REL} {CD47,CD86,NF2,STAT3} {CD47,CD86,NF2,TNFRSF8} {CD47,CD86,NF2,TYMS} {CD47,CD86,PIM1,PTPRC} {CD47,CD86,PIM1,REL} {CD47,CD86,PIM1,STAT3} {CD47,CD86,PIM1,TNFRSF8} {CD47,CD86,PIM1,TYMS} {CD47,CD86,PTPRC,REL} {CD47,CD86,PTPRC,STAT3} {CD47,CD86,PTPRC,TNFRSF8} {CD47,CD86,PTPRC,TYMS} {CD47,CD86,REL,STAT3} {CD47,CD86,REL,TNFRSF8} {CD47,CD86,REL,TYMS} {CD47,CD86,STAT3,TNFRSF8} {CD47,CD86,STAT3,TYMS} {CD47,CD86,TNFRSF8,TYMS} {CD47,IL16,NF2,PIM1} {CD47,IL16,NF2,PTPRC} {CD47,IL16,NF2,REL} {CD47,IL16,NF2,STAT3} {CD47,IL16,NF2,TNFRSF8} {CD47,IL16,NF2,TYMS} {CD47,IL16,PIM1,PTPRC} {CD47,IL16,PIM1,REL} {CD47,IL16,PIM1,STAT3} {CD47,IL16,PIM1,TNFRSF8} {CD47,IL16,PIM1,TYMS} {CD47,IL16,PTPRC,REL} {CD47,IL16,PTPRC,STAT3} {CD47,IL16,PTPRC,TNFRSF8} {CD47,IL16,PTPRC,TYMS} {CD47,IL16,REL,STAT3} {CD47,IL16,REL,TNFRSF8} {CD47,IL16,REL,TYMS} {CD47,IL16,STAT3,TNFRSF8} {CD47,IL16,STAT3,TYMS} {CD47,IL16,TNFRSF8,TYMS} {CD47,NF2,PIM1,PTPRC} {CD47,NF2,PIM1,REL} {CD47,NF2,PIM1,STAT3} {CD47,NF2,PIM1,TNFRSF8} {CD47,NF2,PIM1,TYMS} {CD47,NF2,PTPRC,REL} {CD47,NF2,PTPRC,STAT3} {CD47,NF2,PTPRC,TNFRSF8} {CD47,NF2,PTPRC,TYMS} {CD47,NF2,REL,STAT3} {CD47,NF2,REL,TNFRSF8} {CD47,NF2,REL,TYMS} {CD47,NF2,STAT3,TNFRSF8} {CD47,NF2,STAT3,TYMS} {CD47,NF2,TNFRSF8,TYMS} {CD47,PIM1,PTPRC,REL} {CD47,PIM1,PTPRC,STAT3} {CD47,PIM1,PTPRC,TNFRSF8} {CD47,PIM1,PTPRC,TYMS} {CD47,PIM1,REL, STAT3} {CD47,PIM1,REL,TNFRSF8} {CD47,PIM1,REL,TYMS} {CD47,PIM1,STAT3,TNFRSF8} {CD47,PIM1,STAT3,TYMS} {CD47,PIM1,TNFRSF8,TYMS} {CD47,PTPRC,REL,STAT3} {CD47,PTPRC,REL,TNFRSF8} {CD47,PTPRC,REL,TYMS} {CD47,PTPRC,STAT3,TNFRSF8} {CD47,PTPRC,STAT3,TYMS} {CD47,PTPRC,TNFRSF8,TYMS} {CD47,REL,STAT3,TNFRSF8} {CD47,REL,STAT3,TYMS} {CD47,REL,TNFRSF8,TYMS} {CD47,STAT3,TNFRSF8,TYMS} {CD86,IL16,NF2,PIM1} {CD86,IL16,NF2,PTPRC} {CD86,IL16,NF2,REL} {CD86,IL16,NF2,STAT3} {CD86,IL16,NF2,TNFRSF8} {CD86,IL16,NF2,TYMS} {CD86,IL16,PIM1,PTPRC} {CD86,IL16,PIM1,REL} {CD86,IL16,PIM1,STAT3} {CD86,IL16,PIM1,TNFRSF8} {CD86,IL16,PIM1,TYMS} {CD86,IL16,PTPRC,REL} {CD86,IL16,PTPRC,STAT3} {CD86,IL16,PTPRC,TNFRSF8} {CD86,IL16,PTPRC,TYMS} {CD86,IL16,REL,STAT3} {CD86,IL16,REL,TNFRSF8} {CD86,IL16,REL,TYMS} {CD86,IL16,STAT3,TNFRSF8} {CD86,IL16,STAT3,TYMS} {CD86,IL16,TNFRSF8,TYMS} {CD86,NF2,PIM1,PTPRC} {CD86,NF2,PIM1,REL} {CD86,NF2,PIM1,STAT3} {CD86,NF2,PIM1,TNFRSF8} {CD86,NF2,PIM1,TYMS} {CD86,NF2,PTPRC,REL} {CD86,NF2,PTPRC,STAT3} {CD86,NF2,PTPRC,TNFRSF8} {CD86,NF2,PTPRC,TYMS} {CD86,NF2,REL,STAT3} {CD86,NF2,REL,TNFRSF8} {CD86,NF2,REL,TYMS} {CD86,NF2,STAT3,TNFRSF8} {CD86,NF2,STAT3,TYMS} {CD86,NF2,TNFRSF8,TYMS} {CD86,PIM1,PTPRC,REL} {CD86,PIM1,PTPRC,STAT3} {CD86,PIM1,PTPRC,TNFRSF8} {CD86,PIM1,PTPRC,TYMS} {CD86,PIM1,REL,STAT3} {CD86,PIM1,REL,TNFRSF8} {CD86,PIM1,REL,TYMS} {CD86,PIM1,STAT3,TNFRSF8} {CD86,PIM1,STAT3,TYMS} {CD86,PIM1,TNFRSF8,TYMS} {CD86,PTPRC,REL,STAT3} {CD86,PTPRC,REL,TNFRSF8} {CD86,PTPRC,REL,TYMS} {CD86,PTPRC,STAT3,TNFRSF8} {CD86,PTPRC,STAT3,TYMS} {CD86,PTPRC,TNFRSF8,TYMS} {CD86,REL,STAT3,TNFRSF8} {CD86,REL,STAT3,TYMS} {CD86,REL,TNFRSF8,TYMS} {CD86, STAT3,TNFRSF8,TYMS} {IL16,NF2,PIM1,PTPRC} {IL16,NF2,PIM1,REL} {IL16,NF2,PIM1,STAT3} {IL16,NF2,PIM1,TNFRSF8} {IL16,NF2,PIM1,TYMS} {IL16,NF2,PTPRC,REL} {IL16,NF2,PTPRC,STAT3} {IL16,NF2,PTPRC,TNFRSF8} {IL16,NF2,PTPRC,TYMS} {IL16,NF2,REL,STAT3} {IL16,NF2,REL,TNFRSF8} {IL16,NF2,REL,TYMS} {IL16,NF2,STAT3,TNFRSF8} {IL16,NF2,STAT3,TYMS} {IL16,NF2,TNFRSF8,TYMS} {IL16,PIM1,PTPRC,REL} {IL16,PIM1,PTPRC,STAT3} {IL16,PIM1,PTPRC,TNFRSF8} {IL16,PIM1,PTPRC,TYMS} {IL16,PIM1,REL,STAT3} {IL16,PIM1,REL,TNFRSF8} {IL16,PIM1,REL,TYMS} {IL16,PIM1,STAT3,TNFRSF8} {IL16,PIM1,STAT3,TYMS} {IL16,PIM1,TNFRSF8,TYMS} {IL16,PTPRC,REL,STAT3} {IL16,PTPRC,REL,TNFRSF8} {IL16,PTPRC,REL,TYMS} {IL16,PTPRC,STAT3,TNFRSF8} {IL16,PTPRC,STAT3,TYMS} {IL16,PTPRC,TNFRSF8,TYMS} {IL16,REL,STAT3,TNFRSF8} {IL16,REL,STAT3,TYMS} {IL16,REL,TNFRSF8,TYMS} {IL16,STAT3,TNFRSF8,TYMS} {NF2,PIM1,PTPRC,REL} {NF2,PIM1,PTPRC,STAT3} {NF2,PIM1,PTPRC,TNFRSF8} {NF2,PIM1,PTPRC,TYMS} {NF2,PIM1,REL,STAT3} {NF2,PIM1,REL,TNFRSF8} {NF2,PIM1,REL,TYMS} {NF2,PIM1,STAT3,TNFRSF8} {NF2,PIM1,STAT3,TYMS} {NF2,PIM1,TNFRSF8,TYMS} {NF2,PTPRC,REL,STAT3} {NF2,PTPRC,REL,TNFRSF8} {NF2,PTPRC,REL,TYMS} {NF2,PTPRC,STAT3,TNFRSF8} {NF2,PTPRC,STAT3,TYMS} {NF2,PTPRC,TNFRSF8,TYMS} {NF2,REL,STAT3,TNFRSF8} {NF2,REL,STAT3,TYMS} {NF2,REL,TNFRSF8,TYMS} {NF2,STAT3,TNFRSF8,TYMS} {PIM1,PTPRC,REL,STAT3} {PIM1,PTPRC,REL,TNFRSF8} {PIM1,PTPRC,REL,TYMS} {PIM1,PTPRC,STAT3,TNFRSF8} {PIM1,PTPRC,STAT3,TYMS} {PIM1,PTPRC,TNFRSF8,TYMS} {PIM1,REL,STAT3,TNFRSF8} {PIM1,REL,STAT3,TYMS} {PIM1,REL,TNFRSF8,TYMS} {PIM1,STAT3,TNFRSF8,TYMS} {PTPRC,REL,STAT3,TNFRSF8} {PTPRC,REL,STAT3,TYMS} {PTPRC,REL,TNFRSF8,TYMS} {PTPRC,STAT3,TNFRSF8,TYMS} {REL,STAT3,TNFRSF8,TYMS};

i. any gene set comprising or consisting of any one or any two (to the extent not duplicative) of the following two-gene combinations: {CD47,CD86} {CD47,ENTPD1} {CD47,FOXP1} {CD47,FUT8} {CD47,IL16} {CD47,ITPKB} {CD47,LRMP} {CD47,MME} {CD47,NF2} {CD47,PIM1} {CD47,PTPRC} {CD47,REL} {CD47,STAT3} {CD47,TNFRSF8} {CD47,TYMS} {CD86,ENTPD1} {CD86,FOXP1} {CD86,FUT8} {CD86,IL16} {CD86,ITPKB} {CD86,LRMP} {CD86,MME} {CD86,NF2} {CD86,PIM1} {CD86,PTPRC} {CD86,REL 1 CD86,STAT3} {CD86,TNFRSF8} {CD86,TYMS} {ENTPD1,FOXP1} {ENTPD1,FUT8} {ENTPD1,IL16} {ENTPD1,ITPKB} {ENTPD1,LRMP} {ENTPD1,MME} {ENTPD1,NF2} {ENTPD1,PIM1} {ENTPD1,PTPRC} {ENTPD1,REL} {ENTPD1,STAT3} {ENTPD1,TNFRSF8} {ENTPD1,TYMS} {FOXP1,FUT8} {FOXP1,IL16} {FOXP1,ITPKB} {FOXP1,LRMP} {FOXP1,MME} {FOXP1,NF2} {FOXP1,PIM1} {FOXP1,PTPRC} {FOXP1,REL} {FOXP1,STAT3} {FOXP1,TNFRSF8} {FOXP1,TYMS} {FUT8,IL16} {FUT8,ITPKB} {FUT8,LRMP} {FUT8,MME} {FUT8,NF2} {FUT8,PIM1} {FUT8,PTPRC} {FUT8,REL} {FUT8,STAT3} {FUT8,TNFRSF8} {FUT8,TYMS} {IL16,ITPKB} {IL16,LRMP} {IL16,MME} {IL16,NF2} {IL16,PIM1} {IL16,PTPRC} {IL16,REL} {IL16,STAT3} {IL16,TNFRSF8} {IL16,TYMS} {ITPKB,LRMP} {ITPKB,MME} {ITPKB,NF2} {ITPKB,PIM1} {ITPKB,PTPRC} {ITPKB,REL} {ITPKB,STAT3} {ITPKB,TNFRSF8} {ITPKB,TYMS} {LRMP,MME} {LRMP,NF2} {LRMP,PIM1} {LRMP,PTPRC} {LRMP,REL} {LRMP,STAT3} {LRMP,TNFRSF8} {LRMP,TYMS} {MME,NF2} {MME,PIM1} {MME,PTPRC} {MME,REL} {MME,STAT3} {MME,TNFRSF8} {MME,TYMS} {NF2,PIM1} {NF2,PTPRC NF2,REL} {NF2,STAT3} {NF2,TNFRSF8} {NF2,TYMS} {PIM1,PTPRC} {PIM1,REL} {PIM1,STAT3} {PIM1,TNFRSF8} {PIM1,TYMS} {PTPRC,REL} {PTPRC,STAT3} {PTPRC,TNFRSF8} {PTPRC,TYMS} {REL,STAT3} {REL,TNFRSF8} {REL,TYMS} {STAT3,TNFRSF8 STAT3,TYMS} {TNFRSF8,TYMS}; and j. any gene set comprising or consisting of any one or any two (to the extent not duplicative) of the following three-gene combinations: {CD47,CD86,ENTPD1} {CD47,CD86,FOXP1} {CD47,CD86,FUT8} {CD47,CD86,IL16} {CD47,CD86,ITPKB} {CD47,CD86,LRMP} {CD47,CD86,MME} {CD47,CD86,NF2} {CD47,CD86,PIM1} {CD47,CD86,PTPRC} {CD47,CD86,REL} {CD47,CD86,STAT3} {CD47,CD86,TNFRSF8} {CD47,CD86,TYMS} {CD47,ENTPD1,FOXP1} {CD47,ENTPD1,FUT8} {CD47,ENTPD1,IL16} {CD47,ENTPD1,ITPKB} {CD47,ENTPD1,LRMP} {CD47,ENTPD1,MME} {CD47,ENTPD1,NF2} {CD47,ENTPD1,PIM1} {CD47,ENTPD1,PTPRC} {CD47,ENTPD1,REL} {CD47,ENTPD1,STAT3} {CD47,ENTPD1,TNFRSF8} {CD47,ENTPD1,TYMS} {CD47,FOXP1,FUT8} {CD47,FOXP1,IL16} {CD47,FOXP1,ITPKB} {CD47,FOXP1,LRMP} {CD47,FOXP1,MME} {CD47,FOXP1,NF2} {CD47,FOXP1,PIM1} {CD47,FOXP1,PTPRC} {CD47,FOXP1,REL} {CD47,FOXP1,STAT3} {CD47,FOXP1,TNFRSF8} {CD47,FOXP1,TYMS} {CD47,FUT8,IL16} {CD47,FUT8,ITPKB} {CD47,FUT8,LRMP} {CD47,FUT8,MME} {CD47,FUT8,NF2} {CD47,FUT8,PIM1} {CD47,FUT8,PTPRC} {CD47,FUT8,REL} {CD47,FUT8,STAT3} {CD47,FUT8,TNFRSF8} {CD47,FUT8,TYMS CD47,IL16,ITPKB} {CD47,IL16,LRMP} {CD47,IL16,MME} {CD47,IL16,NF2} {CD47,IL16,PIM1} {CD47,IL16,PTPRC} {CD47,IL16,REL} {CD47,IL16,STAT3} {CD47,IL16,TNFRSF8} {CD47,IL16,TYMS} {CD47,ITPKB,LRMP} {CD47,ITPKB,MME} {CD47,ITPKB,NF2} {CD47,ITPKB,PIM1} {CD47,ITPKB,PTPRC} {CD47,ITPKB,REL} {CD47,ITPKB,STAT3} {CD47,ITPKB,TNFRSF8} {CD47,ITPKB,TYMS} {CD47,LRMP,MME} {CD47,LRMP,NF2} {CD47,LRMP,PIM1} {CD47,LRMP,PTPRC} {CD47,LRMP,REL} {CD47,LRMP,STAT3} {CD47,LRMP,TNFRSF8} {CD47,LRMP,TYMS} {CD47,MME,NF2} {CD47,MME,PIM1} {CD47,MME,PTPRC} {CD47,MME,REL} {CD47,MME, STAT3} {CD47,MME,TNFRSF8} {CD47,MME,TYMS} {CD47,NF2,PIM1} {CD47,NF2,PTPRC} {CD47,NF2,REL} {CD47,NF2,STAT3} {CD47,NF2,TNFRSF8} {CD47,NF2,TYMS} {CD47,PIM1,PTPRC} {CD47,PIM1,REL} {CD47,PIM1,STAT3} {CD47,PIM1,TNFRSF8} {CD47,PIM1,TYMS} {CD47,PTPRC,REL} {CD47,PTPRC,STAT3} {CD47,PTPRC,TNFRSF8} {CD47,PTPRC,TYMS} {CD47,REL,STAT3} {CD47,REL,TNFRSF8} {CD47,REL,TYMS} {CD47,STAT3,TNFRSF8} {CD47,STAT3, TYMS} {CD47,TNFRSF8,TYMS} {CD86,ENTPD1, FOXP1} {CD86,ENTPD1,FUT8} {CD86,ENTPD1, IL16} {CD86,ENTPD1,ITPKB} {CD86,ENTPD1, LRMP} {CD86,ENTPD1,MME} {CD86,ENTPD1, NF2} {CD86,ENTPD1,PIM1} {CD86,ENTPD1, PTPRC} {CD86,ENTPD1,REL} {CD86,ENTPD1, STAT3} {CD86,ENTPD1,TNFRSF8} {CD86, ENTPD1,TYMS} {CD86,FOXP1,FUT8} {CD86, FOXP1,IL16} {CD86,FOXP1,ITPKB} {CD86, FOXP1,LRMP} {CD86,FOXP1,MME} {CD86, FOXP1,NF2} {CD86,FOXP1,PIM1} {CD86,FOXP1, PTPRC} {CD86,FOXP1,REL} {CD86,FOXP1, STAT3} {CD86,FOXP1,TNFRSF8} {CD86,FOXP1, TYMS} {CD86,FUT8,IL16} {CD86,FUT8,ITPKB} {CD86,FUT8,LRMP} {CD86,FUT8,MME} {CD86, FUT8,NF2} {CD86,FUT8,PIM1} {CD86,FUT8,PT-PRC} {CD86,FUT8,REL} {CD86,FUT8,STAT3} {CD86,FUT8,TNFRSF8} {CD86,FUT8,TYMS} {CD86,IL16,ITPKB} {CD86,IL16,LRMP} {CD86, IL16,MME} {CD86,IL16,NF2} {CD86,IL16,PIM1} {CD86,IL16,PTPRC} {CD86,IL16,REL} {CD86, IL16,STAT3} {CD86,IL16,TNFRSF8} {CD86,IL16, TYMS} {CD86,ITPKB,LRMP} {CD86,ITPKB, MME} {CD86,ITPKB,NF2} {CD86,ITPKB,PIM1} {CD86,ITPKB,PTPRC} {CD86,ITPKB,REL} {CD86, ITPKB,STAT3} {CD86,ITPKB,TNFRSF8} {CD86, ITPKB,TYMS} {CD86,LRMP,MME} {CD86,LRMP, NF2} {CD86,LRMP,PIM1} {CD86,LRMP,PTPRC} {CD86,LRMP,REL} {CD86,LRMP,STAT3} {CD86, LRMP,TNFRSF8} {CD86,LRMP,TYMS} {CD86, MME,NF2} {CD86,MME,PIM1} {CD86,MME,PT-PRC} {CD86,MME,REL} {CD86,MME, STAT3} {CD86,MME,TNFRSF8} {CD86,MME,TYMS} {CD86,NF2,PIM1} {CD86,NF2,PTPRC} {CD86, NF2,REL} {CD86,NF2,STAT3} {CD86,NF2,TN-FRSF8} {CD86,NF2,TYMS} {CD86,PIM1,PTPRC} {CD86,PIM1,REL} {CD86,PIM1,STAT3} {CD86, PIM1,TNFRSF8} {CD86,PIM1,TYMS} {CD86,PT-PRC,REL} {CD86,PTPRC,STAT3} {CD86,PTPRC, TNFRSF8} {CD86,PTPRC,TYMS} {CD86,REL, STAT3} {CD86,REL,TNFRSF8} {CD86,REL, TYMS} {CD86,STAT3,TNFRSF8} {CD86,STAT3, TYMS} {CD86,TNFRSF8,TYMS} {ENTPD1, FOXP1,FUT8} {ENTPD1,FOXP1,IL16} {ENTPD1, FOXP1,ITPKB} {ENTPD1,FOXP1,LRMP} {ENTPD1,FOXP1,MME} {ENTPD1,FOXP1,NF2} {ENTPD1,FOXP1,PIM1} {ENTPD1,FOXP1,PT-PRC} {ENTPD1,FOXP1,REL} {ENTPD1,FOXP1, STAT3} {ENTPD1,FOXP1, TNFRSF8} {ENTPD1, FOXP1,TYMS} {ENTPD1,FUT8,IL16} {ENTPD1, FUT8,ITPKB} {ENTPD1,FUT8,LRMP} {ENTPD1, FUT8,MME} {ENTPD1,FUT8,NF2} {ENTPD1, FUT8,PIM1} {ENTPD1,FUT8,PTPRC} {ENTPD1, FUT8,REL} {ENTPD1,FUT8,STAT3} {ENTPD1, FUT8,TNFRSF8} {ENTPD1,FUT8,TYMS} {ENTPD1,IL16,ITPKB} {ENTPD1,IL16,LRMP} {ENTPD1,IL16,MME} {ENTPD1,IL16,NF2} {ENTPD1,IL16,PIM1} {ENTPD1,IL16,PTPRC} {ENTPD1,IL16,REL} {ENTPD1,IL16,STAT3} {ENTPD1,IL16,TNFRSF8} {ENTPD1,IL16,TYMS} {ENTPD1,ITPKB,LRMP} {ENTPD1,ITPKB,MME} {ENTPD1,ITPKB,NF2} {ENTPD1,ITPKB,PIM1} {ENTPD1,ITPKB,PTPRC} {ENTPD1,ITPKB,REL} {ENTPD1,ITPKB,STAT3} {ENTPD1,ITPKB,TN-FRSF8} {ENTPD1,ITPKB,TYMS} {ENTPD1,LRMP, MME} {ENTPD1,LRMP,NF2} {ENTPD1,LRMP, PIM1} {ENTPD1,LRMP,PTPRC} {ENTPD1,LRMP, REL} {ENTPD1,LRMP,STAT3} {ENTPD1,LRMP, TNFRSF8} {ENTPD1,LRMP,TYMS} {ENTPD1, MME,NF2} {ENTPD1,MME,PIM1} {ENTPD1, MME,PTPRC} {ENTPD1,MME,REL} {ENTPD1, MME,STAT3} {ENTPD1,MME,TNFRSF8} {ENTPD1,MME,TYMS} {ENTPD1,NF2,PIM1} {ENTPD1,NF2,PTPRC} {ENTPD1,NF2,REL} {ENTPD1,NF2,STAT3} {ENTPD1,NF2,TNFRSF8} {ENTPD1,NF2,TYMS} {ENTPD1,PIM1,PTPRC} {ENTPD1,PIM1,REL} {ENTPD1,PIM1,STAT3} {ENTPD1,PIM1,TNFRSF8} {ENTPD1,PIM1, TYMS} {ENTPD1,PTPRC,REL} {ENTPD1,PTPRC, STAT3} {ENTPD1,PTPRC,TNFRSF8} {ENTPD1,PT-PRC,TYMS} {ENTPD1,REL,STAT3} {ENTPD1, REL,TNFRSF8} {ENTPD1,REL,TYMS} {ENTPD1, STAT3,TNFRSF8} {ENTPD1,STAT3,TYMS} {ENTPD1,TNFRSF8,TYMS} {FOXP1,FUT8,IL16} {FOXP1,FUT8,ITPKB} {FOXP1,FUT8,LRMP} {FOXP1,FUT8,MME} {FOXP1,FUT8,NF2} {FOXP1,FUT8,PIM1} {FOXP1,FUT8,PTPRC} {FOXP1,FUT8,REL} {FOXP1,FUT8,STAT3} {FOXP1,FUT8,TNFRSF8} {FOXP1,FUT8,TYMS} {FOXP1,IL16,ITPKB} {FOXP1,IL16,LRMP} {FOXP1,IL16,MME} {FOXP1,IL16,NF2} {FOXP1, IL16,PIM1} {FOXP1,IL16,PTPRC} {FOXP1,IL16, REL} {FOXP1,IL16,STAT3} {FOXP1,IL16,TN-FRSF8} {FOXP1,IL16,TYMS} {FOXP1,ITPKB, LRMP} {FOXP1,ITPKB,MME} {FOXP1,ITPKB, NF2} {FOXP1,ITPKB,PIM1} {FOXP1,ITPKB, PTPRC} {FOXP1,ITPKB,REL} {FOXP1,ITPKB, STAT3} {FOXP1,ITPKB,TNFRSF8} {FOXP1, ITPKB,TYMS} {FOXP1,LRMP,MME} {FOXP1, LRMP,NF2} {FOXP1,LRMP,PIM1} {FOXP1,LRMP, PTPRC} {FOXP1,LRMP,REL} {FOXP1,LRMP, STAT3} {FOXP1,LRMP,TNFRSF8} {FOXP1,LRMP, TYMS} {FOXP1,MME,NF2} {FOXP1,MME,PIM1} {FOXP1,MME,PTPRC} {FOXP1,MME,REL} {FOXP1,MME,STAT3} {FOXP1,MME,TNFRSF8} {FOXP1,MME,TYMS} {FOXP1,NF2,PIM1} {FOXP1,NF2,PTPRC} {FOXP1,NF2,REL} {FOXP1, NF2,STAT3} {FOXP1,NF2,TNFRSF8} {FOXP1,NF2, TYMS} {FOXP1,PIM1,PTPRC} {FOXP1,PIM1, REL} {FOXP1,PIM1,STAT3} {FOXP1,PIM1, TNFRSF8} {FOXP1,PIM1,TYMS} {FOXP1,PTPRC, REL} {FOXP1,PTPRC,STAT3} {FOXP1,PTPRC, TNFRSF8} {FOXP1,PTPRC,TYMS} {FOXP1,REL, STAT3} {FOXP1,REL,TNFRSF8} {FOXP1,REL, TYMS} {FOXP1,STAT3, TNFRSF8} {FOXP1, STAT3,TYMS} {FOXP1,TNFRSF8,TYMS} {FUT8, IL16,ITPKB} {FUT8,IL16,LRMP} {FUT8,IL16, MME} {FUT8,IL16,NF2} {FUT8,IL16,PIM1} {FUT8,IL16,PTPRC} {FUT8,IL16,REL} {FUT8, IL16,STAT3} {FUT8,IL16,TNFRSF8} {FUT8,IL16, TYMS} {FUT8,ITPKB,LRMP} {FUT8,ITPKB, MME} {FUT8,ITPKB,NF2} {FUT8,ITPKB,PIM1} {FUT8,ITPKB,PTPRC} {FUT8,ITPKB,REL} {FUT8, ITPKB,STAT3} {FUT8,ITPKB,TNFRSF8} {FUT8, ITPKB,TYMS} {FUT8,LRMP,MME} {FUT8,LRMP, NF2} {FUT8,LRMP,PIM1} {FUT8,LRMP,PTPRC} {FUT8,LRMP,REL} {FUT8,LRMP,STAT3} {FUT8, LRMP,TNFRSF8} {FUT8,LRMP,TYMS} {FUT8, MME,NF2} {FUT8,MME,PIM1} {FUT8,MME,PT-PRC} {FUT8,MME,REL} {FUT8,MME,STAT3} {FUT8,MME,TNFRSF8} {FUT8,MME,TYMS} {FUT8,NF2,PIM1} {FUT8,NF2,PTPRC} {FUT8, NF2,REL} {FUT8,NF2,STAT3} {FUT8,NF2,TN-FRSF8} {FUT8,NF2,TYMS} {FUT8,PIM1,PTPRC}

{FUT8,PIM1,REL} {FUT8,PIM1,STAT3} {FUT8, PIM1,TNFRSF8} {FUT8,PIM1,TYMS} {FUT8,PTPRC,REL} {FUT8,PTPRC,STAT3} {FUT8,PTPRC, TNFRSF8} {FUT8,PTPRC,TYMS} {FUT8,REL, STAT3} {FUT8,REL,TNFRSF8} {FUT8,REL, TYMS} {FUT8,STAT3,TNFRSF8} {FUT8,STAT3, TYMS} {FUT8,TNFRSF8,TYMS} {IL16,ITPKB, LRMP} {IL16,ITPKB,MME} {IL16,ITPKB,NF2} {IL16,ITPKB,PIM1} {IL16,ITPKB,PTPRC} {IL16, ITPKB,REL} {IL16,ITPKB,STAT3} {IL16,ITPKB, TNFRSF8} {IL16,ITPKB,TYMS} {IL16,LRMP, MME} {IL16,LRMP,NF2} {IL16,LRMP,PIM1} {IL16,LRMP,PTPRC} {IL16,LRMP,REL} {IL16, LRMP,STAT3} {IL16,LRMP,TNFRSF8} {IL16, LRMP,TYMS} {IL16,MME,NF2} {IL16,MME, PIM1} {IL16,MME,PTPRC} {IL16,MME,REL} {IL16,MME,STAT3} {IL16,MME,TNFRSF8} {IL16, MME,TYMS} {IL16,NF2,PIM1} {IL16,NF2,PTPRC} {IL16,NF2,REL} {IL16,NF2,STAT3} {IL16,NF2,TNFRSF8} {IL16,NF2,TYMS} {IL16,PIM1,PTPRC} {IL16,PIM1,REL} {IL16,PIM1,STAT3} {IL16,PIM1, TNFRSF8} {IL16,PIM1,TYMS} {IL16,PTPRC,REL} {IL16,PTPRC,STAT3} {IL16,PTPRC,TNFRSF8} {IL16,PTPRC,TYMS} {IL16,REL,STAT3} {IL16, REL,TNFRSF8} {IL16,REL,TYMS} {IL16,STAT3, TNPRSF8} {IL16,STAT3,TYMS} {IL16,TNFRSF8, TYMS} {ITPKB,LRMP,MME} {ITPKB,LRMP,NF2} {ITPKB,LRMP,PIM1} {ITPKB,LRMP,PTPRC} {ITPKB,LRMP,REL} {ITPKB,LRMP,STAT3} {ITPKB,LRMP,TNFRSF8} {ITPKB,LRMP,TYMS} {ITPKB,MME,NF2} {ITPKB,MME,PIM1} {ITPKB, MME,PTPRC} {ITPKB,MME,REL} {ITPKB,MME, STAT3} {ITPKB,MME,TNFRSF8} {ITPKB,MME,TYMS} {ITPKB,NF2,PIM1} {ITPKB,NF2,PTPRC} {ITPKB,NF2,REL} {ITPKB,NF2,STAT3} {ITPKB, NF2,TNFRSF8} {ITPKB,NF2,TYMS} {ITPKB, PIM1,PTPRC} {ITPKB,PIM1,REL} {ITPKB,PIM1, STAT3} {ITPKB,PIM1,TNFRSF8} {ITPKB,PIM1, TYMS} {ITPKB,PTPRC,REL} {ITPKB,PTPRC, STAT3} {ITPKB,PTPRC,TNFRSF8} {ITPKB, PTPRC,TYMS} {ITPKB,REL,STAT3} {ITPKB,REL, TNFRSF8} {ITPKB,REL,TYMS} {ITPKB, STAT3, TNFRSF8} {ITPKB,STAT3,TYMS} {ITPKB, TNFRSF8,TYMS} {LRMP,MME,NF2} {LRMP, MME,PIM1} {LRMP,MME,PTPRC} {LRMP,MME, REL} {LRMP,MME,STAT3} {LRMP,MME, TNFRSF8} {LRMP,MME,TYMS} {LRMP,NF2, PIM1} {LRMP,NF2,PTPRC} {LRMP,NF2,REL} {LRMP,NF2,STAT3} {LRMP,NF2,TNFRSF8} {LRMP,NF2,TYMS} {LRMP,PIM1,PTPRC} {LRMP, PIM1,REL} {LRMP,PIM1,STAT3} {LRMP,PIM1,TNFRSF8} {LRMP,PIM1,TYMS} {LRMP,PTPRC,REL} {LRMP,PTPRC,STAT3} {LRMP,PTPRC,TNFRSF8} {LRMP,PTPRC,TYMS} {LRMP,REL,STAT3} {LRMP,REL,TNFRSF8} {LRMP,REL,TYMS} {LRMP,STAT3,TNFRSF8} {LRMP,STAT3,TYMS} {LRMP,TNFRSF8,TYMS MME,NF2,PIM1} {MME, NF2,PTPRC} {MME,NF2,REL} {MME,NF2,STAT3} {MME,NF2,TNFRSF8} {MME,NF2,TYMS} {MME, PIM1,PTPRC} {MME,PIM1,REL} {MME,PIM1, STAT3} {MME,PIM1,TNFRSF8} {MME,PIM1, TYMS} {MME,PTPRC,REL} {MME,PTPRC, STAT3} {MME,PTPRC,TNFRSF8} {MME,PTPRC, TYMS} {MME,REL,STAT3} {MME,REL, TNFRSF8} {MME,REL,TYMS} {MME,STAT3, TNFRSF8} {MME,STAT3,TYMS} {MME, TNFRSF8,TYMS} {NF2,PIM1,PTPRC} {NF2,PIM1, REL} {NF2,PIM1,STAT3} {NF2,PIM1,TNFRSF8} {NF2,PIM1,TYMS} {NF2,PTPRC,REL} {NF2,PTPRC,STAT3} {NF2,PTPRC,TNFRSF8} {NF2,PTPRC,TYMS} {NF2,REL,STAT3} {NF2,REL,TNFRSF8} {NF2,REL,TYMS} {NF2,STAT3,TNFRSF8} {NF2,STAT3,TYMS} {NF2,TNFRSF8,TYMS} {PIM1,PTPRC,REL} {PIM1,PTPRC,STAT3} {PIM1, PTPRC,TNFRSF8} {PIM1,PTPRC,TYMS} {PIM1, REL,STAT3} {PIM1,REL,TNFRSF8} {PIM1,REL, TYMS} {PIM1,STAT3,TNFRSF8} {PIM1,STAT3, TYMS} {PIM1,TNFRSF8,TYMS} {PTPRC,REL, STAT3} {PTPRC,REL,TNFRSF8} {PTPRC,REL, TYMS} {PTPRC,STAT3,TNFRSF8} {PTPRC,STAT3, TYMS} {PTPRC,TNFRSF8,TYMS} {REL,STAT3, TNFRSF8} {REL,STAT3,TYMS} {REL,TNFRSF8, TYMS} {STAT3,TNFRSF8,TYMS}.

III. Obtaining Gene Expression Information

Gene expression is the process that converts the inherited information (e.g., genes; regions of DNA) in an organism's genome to specific functional products (sometimes called gene products). Gene products include RNA (ribonucleic acid) and protein. Gene expression in a particular biological sample can measured by detecting the expression of gene products, including RNA (such as mRNA, tRNA, rRNA and/or miRNA) or protein, in such sample. In some examples, gene expression is measured by sequencing one or more probes that bind to a target nucleic acid (e.g., mRNA).

A variety of techniques are (or may become) available for measuring gene expression in a sample of interest. However, the disclosure is not limited to particular methods of obtaining, measuring, or detecting gene expression. Many such techniques involve detecting the products of the genes (e.g., nucleic acids (such as RNA) and/or protein) expressed in such samples. It may also be (or become) possible to directly detect the activity of a gene or of chromosomal DNA (e.g., transcription rate) independent of measuring its resultant gene products and such techniques also are useful in methods disclosed herein.

Gene expression can be utilized in determining a DLBCL subtype. For example, gene expression of two or more genes (such as two or more DLBCL signature genes) is utilized in determining whether a DLBCL tumor is of the GCB or non-GCB (e.g. ABC) subtype, or is unclassified. In some embodiments, the DLBCL signature includes (1) two or more of: CD47, CD86, IL16, NF2, PIM1, PTPRC, REL, STAT3, TNFRSF8, and TYMS, or (2) two or more of (such as all of) CD47, CD86, ENTPD1, FOXP1, FUT8, IL16, ITPKB, LRMP, MME, NF2, PIM1, PTPRC, REL, STAT3, TNFRSF8, and TYMS. Other specific examples of DLBCL marker(s) include two or more of (such as 2, 3, 4, 5, 6, 7, 8, 9, or 10 of): CD47, ENTPD1, FOXP1, FUT8, IL16, NF2, PIM1, STAT3, TNFRSF8, and TYMS (which are associated with ABC classification), or two or more of (such as 2, 3, 4, 5, or 6 of) CD86, ITPKB, LRMP, MME, PTPRC, and REL (which are associated with GCB classification).

A. Detecting Nucleic-Acid Gene Products

Nucleic-acid gene products are, as the name suggests, products of gene expression that are nucleic acids. Exemplary nucleic acids include DNA or RNA, such as cDNA, protein-coding RNA (e.g., mRNA) or non-coding RNA (e.g., long, non-coding (lnc) RNA). Base pairing between complementary strands of RNA or DNA (i.e., nucleic acid hybridization) forms all or part of the basis for a large representative class of techniques for detecting nucleic-acid gene products. Other representative detection techniques involve nucleic acid sequencing, which may or may not involve hybridization steps and/or bioinformatics steps (e.g., to associate nucleic acid sequence information to its corresponding gene). These and other methods of detecting nucleic acids are known in the art and, while representative techniques are described herein, this disclosure is not limited to particular methods of nucleic acid detection.

1. Optional Nucleic Acid Isolation

In some examples, nucleic acids are isolated or extracted from the test sample prior to contacting such nucleic acids in the sample with a complementary nucleic acid probe or primer and/or otherwise detecting such nucleic acids in the sample. Nucleic acids (such as RNA (e.g., mRNA or lncRNA) or DNA) can be isolated from the sample according to any of a number of methods. Representative methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993). Representative methods for RNA (e.g., mRNA or lncRNA) extraction similarly are well known in the art and are disclosed in standard textbooks of molecular biology, including Ausubel et al., *Current Protocols of Molecular Biology*, John Wiley and Sons (1997).

After isolation or extraction of nucleic acids (e.g., RNA (such as mRNA or lncRNA) or DNA) from a sample, any of a number of optional other steps may be performed to prepare such nucleic acids for detection, including measuring the concentration of the isolated nucleic acid, repair (or recovery) of degraded or damaged RNA, RNA reverse transcription, and/or amplification of RNA or DNA.

In other examples, a sample (e.g., FFPE tissue sample) is suspended in a buffer (e.g., lysis buffer) and nucleic acids (such as RNA or DNA) present in the suspended sample are not isolated or extracted (e.g., purified in whole or in part) from such suspended sample and are contacted in such suspension with one or more complementary nucleic acid probe(s) (e.g., NPPs or NPPFs); thereby, eliminating a need for isolation or extraction of nucleic acids (e.g., RNA) from the sample. This embodiment is particularly advantageous where the nucleic acids (such as RNA or DNA) present in the suspended sample are crosslinked or fixed to cellular structures and are not readily isolatable or extractable. Relatively short (e.g., less than 100 base pairs, such as 75-25 base pairs or 50-25 base pairs) probes for detection are useful in some non-extraction method embodiments. Specific methods (e.g., qNPA and qNPS) for detecting nucleic acids (e.g., RNA) in a sample without prior extraction of such nucleic acids are described herein.

2. Nucleic Acid Hybridization

In some examples, determining the expression level of two or more disclosed DLBCL biomarkers (such as two or more of those in Table 1) in the methods provided herein can include contacting the sample with a plurality of nucleic acid probes (such as NPPs or NPPFs+CFS) or paired amplification primers, wherein each probe or paired primers in the plurality is/are specific and complementary to a biomarkers in Table 1, under conditions that permit the plurality of nucleic acid probes or paired primers to hybridize to its/their complementary biomarker in Table 1. In one example, the method can also include after contacting the sample with the plurality of nucleic acid probes (such as NPPs or NPPFs+ CFS), contacting the sample with a nuclease that digests single-stranded nucleic acid molecules. In other examples, each of the at least two biomarkers in Table 2, is contacted with "tiled probes" that consists of multiple (e.g., at least 2, at least 5, or at least 10 probes, such as 2, 3, 4, 5, 6, 7, 8, 9, or 10) probes (e.g., NPPs or NPPFs) specific for each such biomarker, which design can be useful, for example, to increase the signal obtained from such gene product or to detect multiple variants of the same gene product. For example, each probe in the tiled probe set may bind to a different region of a target nucleic acid molecule (or overlap slightly).

In some examples, nucleic acids are detected by nucleic acid hybridization. Nucleic acid hybridization involves providing a probe and target nucleic acid (e.g., at least two of those in Table 1) under conditions where the probe and its complementary target can form stable hybrid duplexes through complementary base pairing. In some examples, the nucleic acids that do not form hybrid duplexes are then removed (e.g., washed away, digested by nuclease or physically removed) leaving the hybridized nucleic acids to be detected, such as through detection of a (directly or indirectly) attached detectable label. In specific examples, nucleic acids that do not form hybrid duplexes, such as any excess probe that does not hybridize to its respective target, and the regions of the target sequence that are not complementary to the probes, can be digested away by addition of nuclease, leaving just the hybrid duplexes of target sequence of complementary probe.

It is generally recognized that nucleic acids are denatured by increasing the temperature and/or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency. The strength of hybridization can be increased without lowering the stringency of hybridization, and thus the specificity of hybridization can be maintained in a high stringency buffer, by including unnatural bases in the probes, such as by including locked nucleic acids or peptide nucleic acids.

Changes in expression of a nucleic and/or the presence of nucleic acid detected by these methods for instance can include increases or decreases in the level (amount) or functional activity of such nucleic acids, their expression or translation into protein, or in their localization or stability. An increase or a decrease, for example relative to a normalization biomarker, can be, for example, at least a 1-fold, at least a 2-fold, or at least a 5-fold, such as about a 1-fold, 2-fold, 3-fold, 4-fold, 5-fold, change (increase or decrease) in the expression of and/or the presence of a particular nucleic acid, such as a nucleic acid corresponding to the biomarker shown in Table 1.

In one example, gene expression is measured using a multiplexed methodology. In such methods, a plurality of measurements (e.g., gene expression measurements) can be made in a single sample. Various technologies have evolved that permit the monitoring of large numbers of genes in a single sample (e.g., traditional microarrays, multiplexed PCR, serial analysis of gene expression (SAGE; e.g., U.S. Pat. No. 5,866,330), multiplex ligation-dependent probe amplification (MLPA), high-throughput sequencing, labeled bead-based technology (e.g., U.S. Pat. Nos. 5,736,330 and 6,449,562), digital molecular barcoding technology (e.g., U.S. Pat. No. 7,473,767).

Arrays are one set of tools for multiplex detection of gene expression. An array is a systematic arrangement of elements (e.g., analyte capture reagents (such as, target-specific oligonucleotide probes, aptamers, or antibodies)) where a set of values (e.g., gene expression values) can be associated with an identification key. The arrayed elements may be systematically identified on a single surface (e.g., by spatial mapping or by differential tagging), using separately identifiable surfaces (e.g., flow channels or beads), or by a combination thereof.

Other useful embodiments involve high-throughput methodology, with which multiple samples may be queried at one time. High-throughput, multiplexed embodiments (contemporaneously measuring the expression of a plurality of genes in a plurality of samples) also are contemplated. Examples of methods and assay systems that can be used to detect the disclosed biomarkers are high throughput assay techniques disclosed in International Patent Publication Nos. WO 2003/002750 and WO 2008/121927, WO 1999/032663, WO 2000/079008, WO/2000/037684, and WO 2000/037683 and U.S. Pat. Nos. 6,232,066, 6,458,533, 6,238,869, and 7,659,063, which are incorporated by reference herein in so far as they describe high throughput assay techniques.

In some array embodiments, nucleic acid sequences of interest (such as oligonucleotides) that are designed to capture (directly or indirectly) two or more products of the genes shown in Table 1 are plated or arrayed on a microchip substrate. For example, the array can include oligonucleotides having sufficient complementary to at least two of the genes shown in Table 2 (such as at least 3, at least 4, at least 5, at least 6, at least 7, at least 8, at least 9, at least 10, or all 16 of the genes shown in Table 1). In other examples, the array can include oligonucleotides complementary to a portion of a nuclease protection probe (NPP) having a portion that is complementary to a product of at least two of CD47, CD86, IL16, NF2, PIM1, PTPRC, REL, STAT3, TNFRSF8, and TYMS, such as two or more of CD47, CD86, ENTPD1, FOXP1, FUT8, IL16, ITPKB, LRMP, MME, NF2, PIM1, PTPRC, REL, STAT3, TNFRSF8, such as at least 3, at least 4, at least 5, at least 6, at least 7, at least 8, at least 9, at least 10, or all 16 of the genes shown in Table 1.

The arrayed sequences are then hybridized with nucleic acids, such as cDNA or RNA (e.g., mRNA, miRNA and/or lncRNA), from the test sample (e.g., DLBCL sample obtained from a subject, whose characterization as ABC or GCB is desired). In one example, the nucleic acids from the test sample (which may be isolated) are labeled, such that their hybridization with the specific complementary oligonucleotide on the array can be determined. Alternatively, the test sample nucleic acids are not labeled, and hybridization between the oligonucleotides on the array and the target nucleic acid is detected using a sandwich assay, for example using additional oligonucleotides complementary to the target that are labeled.

In one embodiment, the hybridized nucleic acids are detected by detecting one or more labels attached to the sample nucleic acids or attached to a nucleic acid probe that hybridizes directly or indirectly to the target nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification using a labeled nucleotide (such as fluorescein-labeled UTP and/or CTP) incorporates a label into the transcribed nucleic acids.

Detectable labels suitable for use in any of the disclosed methods (e.g., for nucleic acid or protein detection or sequencing) include any compound or composition that is conjugated directly or indirectly to another molecule (such as a nucleic acid molecule or a nucleotide) to facilitate detection of that molecule, for example detectable by spectroscopic, photochemical, biochemical, immunochemical, electrical, optical or chemical means. Non-limiting examples of labels include fluorescent and fluorogenic moieties, chromogenic moieties, haptens, affinity tags, enzymes, and radioactive isotopes. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N.Y., 1993).

In situ hybridization (ISH), such as chromogenic in situ hybridization (CISH) and silver in situ hybridization (SISH), is an exemplary method for detecting and comparing expression of genes of interest (such as at least two of those in Table 1). ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of the biomarkers in Table 1. DNA ISH (such as CISH and SISH) can be used to detect nucleic acids at the genomic level.

Sample cells or tissues are treated to increase their permeability to allow a probe, such as a probe specific for a biomarker in Table 1, to enter the cells. The probe is added to the treated cells, allowed to hybridize at pertinent temperature, and excess probe is washed away. A complementary probe may be labeled with a detectable label, such as a radioactive, fluorescent or antigenic tag, so that the probe's location and quantity in the tissue can be determined, for example using autoradiography, fluorescence microscopy or immunoassay.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences. Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

3. Nucleic Acid Amplification

In some examples, target nucleic acid molecules (such as nucleic acid gene products (e.g., mRNA or lncRNA)) are amplified as a means to their detection (or as a step in their detection). In some examples, nucleic acid expression levels are determined during amplification, for example by using real time RT-PCR. Thus, one or more of the DLBCL biomarkers in Table 1 can be detected (for example quantitatively) in a sample using amplification methods and appropriate primers.

Examples of in vitro amplification methods that can be used include, but are not limited to, quantitative real-time PCR, real time quantitative RT-PCR, strand displacement amplification; transcription-free isothermal amplification; repair chain reaction amplification; ligase chain reaction amplification; gap filling ligase chain reaction amplification; coupled ligase detection and PCR and NASBA™ RNA transcription-free amplification. In one example, a ligation-based method of amplification is used.

4. RNA Sequencing

RNA sequencing can be used obtain multiplexed and, in some embodiments, high-throughput gene expression information, such as information regarding the expression of the markers in Table 1. Methods of RNA sequencing are known (e.g., see Chu and Corey, Nuc. Acid Therapeutics, 22:271 (2012)). Whole-transcriptome sequencing and targeted RNA sequencing techniques each are available and are useful in the disclosed methods. Representative methods for sequencing-based gene expression analysis include serial analysis of gene expression (SAGE), gene expression analysis by massively parallel signature sequencing (MPSS), whole transcriptome shotgun sequencing (aka, WTSS or RNA-Seq), or nuclease-protection sequencing (aka, qNPS or NPSeq; see PCT Pub. No. WO 2012/151111; discussed in more detail below).

5. Quantitative Nuclease Protection Assay (qNPA)

In some examples, the nucleic acid molecules in the sample whose expression is to be measured are detected in the sample utilizing a quantitative nuclease protection assay, for example as described in International Patent Publications WO 99/032663; WO 00/037683; WO 00/037684; WO 00/079008; WO 03/002750; WO 08/121927; and WO 2012/151111 and U.S. Pat. Nos. 6,238,869; 6,458,533; 7,659,063, and 8,741,564, all incorporated herein by reference in their entirety. See also, Martel et al., *Assay and Drug Development Technologies*. 2002, 1 (1-1):61-71; Martel et al., *Progress in Biomedical Optics and Imaging*, 2002, 3:35-43; Martel et al., *Gene Cloning and Expression Technologies*, Q. Lu and M. Weiner, Eds., Eaton Publishing, Natick (2002); Seligmann *PharmacoGenomics*, 2003, 3:36-43; Martel et al., "Array Formats" in "Microarray Technologies and Applications," U. R. Muller and D. Nicolau, Eds, Springer-Verlag, Heidelberg (2005); Sawada et al., *Toxicology in Vitro*, 20:1506-1513, 2006; Bakir, et al., *Bioorg. & Med. Chem Lett*, 17:3473-3479, 2007; Kris et al., *Plant Physiol*. 144:1256-1266, 2007; Roberts et al., *Laboratory Investigation*, 87:979-997, 2007; Rimsza et al., *Blood*, 2008 Oct. 15, 112 (8):3425-3433; Pechhold et al., *Nature Biotechnology*, 27:1038-1042, 2009. All of these are fully incorporated by reference herein.

Using qNPA methods, a nuclease protection probe (NPP) is allowed to hybridize to the target sequence (such as a sequence in Table 1), which is followed by incubation of the sample with a nuclease that digests single stranded nucleic acid molecules. Thus, if the NPP is detected, (e.g. it is not digested by the nuclease) then the target of the probe, for example a target nucleic acid shown in Table 1, is present in the sample, and this presence can be quantified. NPPs can be designed for individual targets and added to an assay as a cocktail for identification (e.g., on an array (referred to as qNPA) or by sequencing (referred to as qNPS)). Thus multiple genes targets can be measured within the same assay and/or array (e.g., by using multiple NPPs).

The NPP is a nucleic acid molecule (such as a DNA or RNA) having sufficient complementary to a target nucleic acid (e.g., an mRNA) that allows it to specifically hybridize to the target nucleic acid. The NPP protects the complementary target nucleic acid molecule from cleavage by a nuclease, such as a nuclease specific for single-stranded nucleic acids. In some examples, the NPP is at least 35 nucleotides (such as 40 to 80 or 50 to 150 nucleotides) and shares at least 90%, at least 95%, or 100% complementarity to the target nucleic acid molecule. The NPP can include unnatural bases. In some examples, the disclosed methods are used to detect (or sequence) several different target nucleic acid molecules in a sample (such as those listed in Table 1) using a plurality of NPPs (such as NPPFs, see below), wherein each NPP (or NPPF) specifically binds to a particular target nucleic acid molecule.

In a specific example, the NPP further includes one or more flanking sequences at the 5'-end and/or 3'-end, and is referred to as an NPPF (see U.S. Pat. No. 8,741,564). The NPPFs include a sequence that is complementary to all or a portion of the target nucleic acid molecule, thus permitting specific binding or hybridization between the target nucleic acid molecule and the NPPF. For example, the region of the NPPF that is complementary to a region of the target nucleic acid molecule binds to or hybridizes to that region of the target nucleic acid molecule with high specificity (and in some examples can also bind to a region of a bifunctional linker). The portion of the NPPF that is complementary to a region of the target nucleic acid molecule can be at least 6 nucleotides in length, such as at least 10, at least 25, or at least 60, such as 6 to 60 nucleotides in length. The NPPFs further include one or more flanking sequences at the 5'-end and/or 3'-end of the NPPF. Thus, the one or more flanking sequences are located 5', 3', or both, to the sequence complementary to the target nucleic acid molecule. If the NPPF includes a flanking sequence at both the 5'-end and 3'-end, in some examples the sequence of each NPPF is different and not complementary. The flanking sequence(s) includes several contiguous nucleotides having a sequence (such as a sequence of at least 6 nucleotides, at least 12 nucleotides, or at least 25 nucleotides, such as 12 to 50 nucleotides) not found in a nucleic acid molecule present in the sample, and provide a universal hybridization and/or amplification sequence. This universal hybridization and/or amplification sequence, when having a sequence complementary to at least a portion of an amplification primer, permits multiplexing, as the same amplification primers can be used to amplify NPPFs specific for different target nucleic acid molecules. It also provides a universal hybridization sequence for all NPPFs, which can be used to add a detectable label to the NPPF or to capture and concentrate NPPFs. For example, if the same flanking sequence is present on NPPFs specific for different target nucleic acid molecules, the same primer can be used to amplify any NPPF having the same flanking sequence, even if the NPPF targets a different nucleic acid molecule. For example, the flanking sequence can be used to capture NPPFs, such as onto a surface. The flanking sequence can contain a variable sequence, such as a sequence that is specific for each specific NPPF and can be used to either capture that NPPF on a surface or for other purposes, such as to identify the NPPF. In some examples the NPPF is at least 35 nucleotides, such as 40 to 80 or 50 to 150 nucleotides. In some examples, the NPPF includes two flanking sequences: one at the 5'-end and the other at the 3'-end. In some examples, the flanking sequence at the 5'-end differs from the flanking sequence at the 3'-end. In addition, if the NPPF includes two flanking sequences, ideally the two flanking sequences have a similar melting temperature (Tm), such as a Tm of +/−5° C.

In some embodiments the NPP or NPPF specifically hybridizes to and/or is complementary to all or part of the target sequence. Thus, the NPPs and NPPFs can include at least 10, at least 15, at least 20, at least 25, at least 30, at least 35, at least 40, at least 45, at least 50, at least 55, at least 60, at least 65, at least 70, at least 75, or more consecutive nucleotides complementary to a target nucleic acid molecule. In some examples the NPPs and NPPFs are not more than 500 nucleotides, such as no more than 400, no more than 300, no more than 250, no more than 200, no more than 100, no more than 50, or even no more than 25 consecutive nucleotides complementary to a target nucleic acid molecule (such as 10 to 500 nucleotides, 10 to 400 nucleotides, 10 to 250 nucleotides, 10 to 200 nucleotides, 10 to 100 nucleotides, 25 to 75 nucleotides, 10 to 60 nucleotides, 40 to 80 nucleotides, 100 to 200 nucleotides, or 10 to 50 consecutive nucleotides complementary to a target nucleic acid molecule. In particular examples, the NPPs and NPPFs is at least 10 nucleotides in length, such as at least 10 contiguous nucleotides complementary to a target nucleic acid sequence or portion thereof, such as target sequences disclosed herein (for example, those in Table 1). Particular lengths of NPPs and NPPFs that can be used to practice the methods of the present disclosure include probes having at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more contiguous nucleotides complementary to a target nucleic acid molecule or a portion thereof. In some examples, NPPs and NPPFs comprise (or NPPs consist of) a nucleic acid sequence with at least 95% sequence identity (such as at least 95%, 96%, 97%, 98%, 99%, or even 100% sequence identity) to the reverse complement of a target sequence. In some examples, the NPPs and NPPFs can include 1, 2, 3, or more mismatches as compared to the reverse complement of the target nucleic acid molecule.

In some examples, NPPs and NPPFs can include one or more (such as 1, 2, 3, or more) synthetic bases or alternative bases (such as inosine). In other examples, the NPPs can include one or more modified nucleotides or nucleic acid analogs, such as one or more locked nucleic acids (see, e.g., U.S. Pat. No. 6,794,499) or one or more peptide nucleic acids. Modified nucleotides, unnatural nucleotides, synthetic, or alternative nucleotides can be used in a NPP or NPPF at one or more positions (such as 1, 2, 3, 4, 5, or more positions). NPPs and NPPFs may also be degenerate at one or more positions (such as 1, 2, 3, 4, 5, or more positions), for example, an NPP or NPPF that includes a mixture of nucleotides (such as 2, 3, or 4 nucleotides) at a specified position in the NPP or NPPF.

In some embodiments, a sample from a subject (such as a sample including nucleic acids, such as RNAs) can be contacted with a plurality of NPPs or NPPFs, wherein at least some of the NPPs and NPPFs specifically bind to at least two different target nucleic acid molecules (e.g., those shown in Table 1). In some examples, the NPPs or NPPFs specifically bind to at least two of CD47, CD86, IL16, NF2, PIM1, PTPRC, REL, STAT3, TNFRSF8, and TYMS (such as 1, 2, 3, 4, 5, 6, 7, 8, 9, or all 10 of these), such as two or more of CD47, CD86, ENTPD1, FOXP1, FUT8, IL16, ITPKB, LRMP, MME, NF2, PIM1, PTPRC, REL, STAT3, TNFRSF8, and TYMS (such as 1, 2, 3, 4, 5, 6, 7, 8, 9, 10, 11, 12, 13, 14, 15, or all 16 of these). In some embodiments, a sample from a subject (such as a sample including nucleic acids, such as RNAs) is also contacted with one or more NPPs or NPPFs specific for one or more housekeeper/normalization genes (e.g., one or more NPPs or NPPFs specific for ANT).

In some examples, the plurality of NPPs or NPPFs includes more than one (such as 2, 3, 4, 5, 6, 7, 8, 9, 10, 11, 12, 13, 14, 15, or 16 or more) different NPPs or NPPFs, each specific for a single target mRNA or a unique region of a target mRNA (e.g., see the target-specific portion of the NPPF sequences in Table 2). The plurality of NPPs or NPPFs are incubated with the sample under conditions sufficient for the NPPs or NPPFs to specifically hybridize to their respective target mRNA. If NPPFs are used, the method includes contacting the sample with a nucleic acid molecule comprising a sequence complementary to the flanking sequence(s) (CFS) under conditions sufficient for the flanking sequence(s) of the NPPF to specifically bind to the CFS. The sample is contacted with a nuclease specific for single-stranded nucleic acids (for example, S1 nuclease), and the presence of the each NPP or NPPF is detected (or sequenced). In some examples, the NPPs or NPPFs are amplified prior to detection (or sequencing). The mRNA(s) are identified as present in the sample and/or are quantified when their respective NPP(s) or NPPF(s) are detected.

a. Treatment of Sample

In some examples, samples (e.g., cells or tissue) from the subject are first lysed or permeabilized in an aqueous solution (for example using a lysis buffer). Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 110° C.) to lyse or permeabilize the cell. In some examples, lysis is performed at about 95° C. In some examples, the lysis step includes incubating the sample at about 95° C. for about 5-15 minutes to denature RNA in the sample, but not genomic DNA. In other examples, the lysis step includes incubating the sample at about 105° C. for about 5-15 minutes to denature nucleic acids in the sample. In one example Proteinase K is included with the lysis buffer.

In some examples, one or more NPPs or NPPFs (such as those including or having a sequence shown in SEQ ID NOS: 1-16) complementary to the one or more targets can be added to a sample at a concentration ranging from about 10 pM to about 10 nM (such as about 30 pM to 5 nM, about 100 pM to about 1 nM), in a buffer such as one containing NaCl, KCl, $H_2PO_4$, EDTA, 0.05% Triton X-100, or combinations thereof (for example, 6×SSPE-T: 0.9 M NaCl, 60 mM $NaH_2PO_4$, 6 mM EDTA, and 0.05% Triton X-100) or lysis buffer. In one example, each NPP or NPPF is added to the sample at a final concentration of at least 10 pM, such as at least 20 pM, at least 30 pM, at least 50 pM, at least 100 pM, at least 150 pM, at least 200 pM, at least 500 pM, at least 1 nM, or at least 10 nM. In one example, each NPP or NPPF is added to the sample at a final concentration of about 30 pM. In another example, each NPP or NPPF is added to the sample at a final concentration of about 167 pM. In a further example, each NPP or NPPF is added to the sample at a final concentration of about 1 nM. In one example, if NPPFs are used, each CFS is added to the sample at a final concentration of about at least 6-times the amount of probe, such as at least 10-times or at least 20-times the amount of probe (such as 6 to 20 times the amount of probe). In one example, each CFS is added at least 1 nM, at least 5 nM, at least 10 nM, at least 50 nM, at least 100 nM, or at least 200 nm, such as 1 to 100, 5 to 100 or 5 to 50 nM. For example if there are six probes, each at 166 pM, each CFSs can be added at 5 to 50 nM. In such examples, NPPs or NPPF not digested by a nuclease, such as S1, if the NPP or NPPF is hybridized to (forms a duplex with) a complementary sequence, such as a target sequence.

b. Exemplary Hybridization Conditions

One of skill in the art can identify conditions sufficient for an NPP or NPPF (+CFS) to specifically hybridize to its target present in the test sample. For example, one of skill in the art can determine experimentally the features (such as length, base composition, and degree of complementarity) that will enable a nucleic acid (e.g., fusion probe) to hybridize to another nucleic acid (e.g., a target nucleic acid in any of Tables 2-8) under conditions of selected stringency, while minimizing non-specific hybridization to other substances or molecules. Typically, the nucleic acid sequence of an NPP will have sufficient complementarity to the corresponding target sequence to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide.

The nucleic acid molecules in the sample are denatured (for example at about 95° C. to about 105° C. for about 5-15 minutes) and hybridized to the plurality of NPPs or NPPF (+CFS) for between about 10 minutes and about 72 hours (for example between about 10 minutes and about 24 hours, such as at least about 1 hour to 20 hours, or about 6 hours to 16 hours) at a temperature ranging from about 4° C. to about 70° C. (for example, about 37° C. to about 65° C., about 42° C. to about 60° C., or about 50° C. to about 60° C.). In some examples, the plurality of NPPs or NPPFs (+CFSs) is incubated with the sample at a temperature of at least about 37° C., at least about 40° C., at least about 45° C., at least about 50° C., at least about 55° C., at least about 60° C., at least about 65° C., or at least about 70° C. In one example, the plurality of NPPs or NPPFs (+CFSs) is incubated with the sample at about 37° C. In another example, the plurality of NPPs or NPPFs (+CFSs) is incubated with the sample at about 42° C. In a further example, the plurality of NPPs or NPPFs (+CFSs) is incubated with the sample at about 50° C. These hybridization temperatures are exemplary, and one of skill in the art can select appropriate hybridization temperature depending on factors such as the length and nucleotide composition of the NPPs or NPPFs (+CFSs).

In some embodiments, the methods do not include nucleic acid purification (for example, nucleic acid purification is not performed prior to contacting the sample with the NPPs or NPPFs (+CFSs) and/or nucleic acid purification is not performed following contacting the sample with the NPPs or NPPFs (+CFSs)). In some examples, the methods do not include nucleic acid amplification (for example, nucleic acid amplification is not performed prior to contacting the sample with the NPPs or NPPFs (+CFSs) and/or nucleic acid amplification is not performed following contacting the sample with the NPPs or NPPFs (+CFSs)). In some examples, no pre-processing of the sample is required except for cell lysis. In some examples, cell lysis and contacting the sample with the plurality of NPPs or NPPFs (+CFSs) occur sequentially. In other examples, cell lysis and contacting the sample with the plurality of NPPs or NPPFs (+CFSs) occur concurrently, in some non-limiting examples without any intervening steps.

c. Treatment with Nuclease

Following hybridization of the one or more NPPs or NPPFs (+CFSs) and nucleic acids in the sample, the sample is subjected to a nuclease protection procedure. NPPs or NPPFs which have hybridized to a target nucleic acid are not hydrolyzed by the nuclease and can be subsequently detected.

Treatment with one or more nucleases will destroy all ss nucleic acid molecules (including RNA and DNA in the sample that is not hybridized to (thus not protected by) NPPs or NPPFs, NPP or NPPFs that are not hybridized to target nucleic acid, and (when used) CFSs not hybridized to an NPPF), but will not destroy ds nucleic acid molecules such as NPPFs which have hybridized to CFSs and a target nucleic acid molecule present in the sample and NPPs which have hybridized to a target nucleic acid molecule present in the sample. For example, if the sample includes a cellular extract or lysate, unwanted nucleic acids, such as non-target genomic DNA, tRNA, rRNA, mRNA, miRNA, and portions of the target nucleic acid molecule(s) that are not hybridized to complementary NPP or NPPF sequences (such as overhangs), which in the case of mRNA or DNA nucleic acid targets will constitute the majority of the nucleic target sequence, can be substantially destroyed in this step. This leaves behind a stoichiometric amount of target nucleic acid/NPP duplex or target nucleic acid/CFS/NPPF duplex. If the target molecule is cross-linked to tissue that occurs from fixation, the NPPs or NPPFs hybridize to the cross-linked target molecule without the need to reverse cross-linking, or otherwise release the target nucleic acid from the tissue to which it is cross-linked.

Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. In a particular example, the nuclease is specific for single-stranded nucleic acids, for example S1 nuclease. An advantage of using a nuclease specific for single-stranded nucleic acids in some method embodiments disclosed herein is to remove such single-stranded ("sticky") molecules from subsequent reaction steps where they may lead to undesirable background or cross-reactivity. S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in a buffer (such as one containing sodium acetate NaCl, KCl, $ZnSO_4$, KATHON, or combinations thereof) is added to the hybridized probe/sample mixture and incubated at about 37° C. to about 60° C. (such as about 50° C.) for 10-120 minutes (for example, 10-30 minutes, 30 to 60 minutes, 60-90 minutes, or 120 minutes) to digest non-hybridized nucleic acid from the sample and non-hybridized NPPs or NPPFs.

The samples can optionally be treated to otherwise remove non-hybridized material and/or to inactivate or remove residual enzymes (e.g., by heating, phenol extraction, precipitation, column filtration, addition of proteinase k, addition of a nuclease inhibitor, chelating divalent cations required by the nuclease for activity, or combinations thereof). In some examples, the samples are optionally treated to dissociate the target nucleic acid and the CFS(s) from its complementary NPPF or the target nucleic acid from its complementary NPP (e.g., using base hydrolysis and heat). In some examples, after hybridization and nuclease treatment, a target nucleic acid molecule hybridized to the NPP or NPPF can be degraded, e.g., by dissociating the duplex with NPP or NPPF in base and then destroying the nucleic acid by nucleases or by chemical/physical treatments, such as base hydrolysis at elevated temperature, leaving the NPP or NPPF in direct proportion to how much had been hybridized to target nucleic acid. Alternatively, the sample can be treated so as to leave the (single strand) hybridized portion of the target nucleic acid, or the duplex formed by the hybridized target nucleic acid and the probe, to be further analyzed.

In some examples following incubation with a nuclease, base (such as NaOH or KOH) is added to increase the pH to about 9 to 12 and the sample heated (for example to 95° C. for 10 minutes). This dissociates the dimers, leaving the NPP or NPPF in a single stranded state, and in the case of RNA, hydrolyzes the RNA target molecules. This step can also neutralize or deactivate the nuclease, such as by raising the pH above about 6.

In some examples the sample is treated to adjust the pH to about 7 to about 8, for example by addition of acid (such as HCl). In some examples the pH is raised to about 7 to about 8 in Tris buffer. Raising the pH can prevent the depurination of DNA and also prevents many ss-specific nucleases (e.g., S1) from functioning fully.

In some examples, the sample is purified or separated to remove undesired nucleic acid or other molecules, for example by gel purification or other separation method.

d. Optional Amplification

In some examples, the NPPs or NPPFs are amplified prior to their detection. For example, the resulting NPPs, NPPFs, or resulting target nucleic acid molecules that have been separated from the NPP or NPPF, can be amplified, for example using routine methods such as PCR or other forms of enzymatic amplification or ligation based methods of amplification. Examples of in vitro amplification methods that can be used include, but are not limited to, quantitative real-time PCR, strand displacement amplification; transcription-free isothermal amplification; repair chain reaction amplification; ligase chain reaction amplification; gap filling ligase chain reaction amplification; coupled ligase detection and PCR; and NASBA™ RNA transcription-free amplification. In one example, a ligation-based method of amplification is used, wherein the primers are NPPF specific and butt-up together so that they can be ligated together, melted off, and then fresh primers ligated together for a series of cycles. Ligation can be enzymatic or non-enzymatic. If the NPPF flanking sequences are used for hybridization of the primers, the amplification can be universal.

During amplification, an experiment tag, and/or sequencing adapter can be incorporated as, for instance, part of the primer and extension constructs, for example at the 3'- or 5'-end or at both ends of the NPP or NPPF. In some example, such tags or adapters or added prior to amplification. Amplification can also be used to introduce a detectable label into the generated NPP or NPPF amplicons (for example if the NPP or NPPF was originally unlabeled or if additional labeling is desired), or other molecule that permits detection or quenching. For example, the amplification primer can include a detectable label, haptan, or quencher which is incorporated into the NPP or NPPF during amplification. Such a label, haptan, or quencher can be introduced at either end of the NPP or NPPF amplicon (or both ends), or anywhere in between.

In some examples, the resulting NPP or NPPF amplicons are cleaned up before detection or sequencing. For example, the amplification reaction mixture can be cleaned up using methods well known in the art (e.g., gel purification, biotin/avidin capture and release, capillary electrophoresis). In one example, the NPP or NPPF amplicons are biotinylated (or include another haptan) and captured onto an avidin or anti-haptan coated bead or surface, washed, and then released for detection or sequencing. The amplified products can also be cleaned up after the last step of amplification, while still double stranded, by a method which uses a nuclease that hydrolyzes single stranded oligonucleotides (such as Exonuclease I), which nuclease can in turn be inactivated before continuing to the next step, such as hybridization to a surface.

e. Detection of NPPs or NPPFs using a Label

The presence of the NPPs or NPPFs (or the remaining target, target:NPP complex, or target:NPPF:CFS complex), the NPP amplicons, or NPPF amplicons, can be detected. Any suitable method can be used to detect the NPP or NPPF probes or amplicons (or the remaining target target:NPP complex, or target:NPPF:CFS complex). In some examples, the NPPs or NPPFs (or amplicons thereof) include a detectable label and detecting the presence of the NPPs or NPPFs (or amplicons thereof) includes detecting the detectable label. In some examples, the NPPs or NPPFs (or amplicons thereof) are labeled with the same detectable label. In other examples, the NPPs or NPPFs (or amplicons thereof) are labeled with different detectable labels (such as a different label for each target). In other examples, the NPPs or NPPFs (or amplicons thereof) are detected indirectly, for example by hybridization with a labeled nucleic acid.

In a specific, non-limiting example, the NPPs or NPPFs (or amplicons thereof) include a biotin label. In this example, the NPPs or NPPFs (or amplicons thereof) can be detected by incubating them (such as on a support, e.g., array or bead, containing the NPPs or NPPFs (or amplicons thereof)) with avidin-HRP or streptavidin-HRP, or a conjugate with another suitable enzyme such as alkaline phosphatase, and then contacting the support with chromogenic-, chemiluminescence-, or fluorescence-generating substrate. In one non-limiting example, the substrate is TMA-3 (Lumigen, Southfield, Mich.). Additional chemiluminescent substrates are commercially available, such as LumiGlo® (KPL, Gaithersburg, Md.), SuperSignal® (Pierce, Rockford, Ill.), and ECL™ (Amersham/GE Healthcare, Piscataway, N.J.). Signal produced by the substrate is detected, for example utilizing a microarray imager (such as an OMIX, OMIX HD, CAPELLA, or SUPERCAPELLA imager, HTG Molecular Diagnostics, Tucson, Ariz.) scanner, or visually such as in a lateral flow device. Europium-based luminescence can be used, as well as electroluminescence or light scatter, or electrical (e.g., conductivity or resistance).

In another example, the NPPs or NPPFs (or amplicons thereof) include a fluorescent label, such as Cy-3 or Cy-5. The NPPs or NPPFs (or amplicons thereof) can be detected utilizing a standard microarray imager (such as a Typhoon™ imager (GE Life Sciences, Piscataway, N.J.), a GenePix® microarray scanner (Molecular Devices, Sunnyvale, Calif.), GeneChip® scanner (Affymetrix, Santa Clara, Calif.), flow cytometry methods, or fluorescent microscopy methods. One of ordinary skill in the art can select suitable detection methods and reagents for these or other detectable labels.

f. Detection of NPPs or NPPFs using Capture Molecules

In some embodiments, following hybridization and nuclease treatment (and optional amplification), the sample is contacted with a surface that includes multiple spatially discrete regions, each including a capture molecule, or is contacted with a plurality of surfaces, each including a capture molecule. For example, the surface can be a population of beads, wherein subpopulations of the beads each include at least one capture molecule. For example a first subpopulation could include at least one capture molecule, while a second subpopulation could include at least one capture molecule having a different sequence than the first, and so on. In some examples, the capture molecule includes at least one anchor associated with a bifunctional linker (also referred to as a "programming linker"). Alternatively, the capture molecule includes a nucleic acid capture probe, having a sequence that is complementary to at least a portion of NPPs or NPPFs (or amplicons thereof), such as complementary to all or a portion of a flanking region of an NPPF or amplicon thereof.

In an example where the capture molecule includes at least one anchor associated with a bifunctional linker, the anchor and the bifunctional linker are associated by hybridization, annealing, covalent linkage, or other binding. The bifunctional linker includes a first portion which specifically binds to (for example, is complementary to) the anchor and a second portion which specifically binds to (for example, is complementary to) one of the plurality of NPPs or NPPFs (or amplicon thereof).

In some embodiments, the disclosed methods include an anchor on a surface (for example on an array), which is associated with a bifunctional linker which is utilized to capture the NPPs or NPPFs (or amplicons thereof) following the nuclease or amplification step. In some examples, an anchor is an oligonucleotide of about 8 to 150 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). In one non-limiting example, the anchor is about 25 nucleotides in length. In some examples, the anchor includes a first portion that specifically binds to the first portion of the bifunctional linker and a second portion that acts as a spacer between the surface and the first portion of the anchor. In some examples, the second portion of the anchor is about 6 to 60 carbon atoms or nucleotides in length (such as about 6, 12, 24, 30, 36, 42, 48, 54, or 60 carbon atoms or nucleotides). In other examples, the second portion of the anchor is about 5 to 100 carbon atoms or nucleotides in length (such as about 10 to 50, 15 to 40, 20 to 30, or about 25 carbon atoms or nucleotides).

The base composition for anchors for the disclosed methods is such that the thermodynamic stability of the anchor and bifunctional linker pairing is high. In some examples, the percentage base composition for the anchors is about 30-40% G, 30-40% C, 10-20% A, and 10-20% T. In some examples, nearest neighbor frequency in the anchors minimizes G-G or C-C nearest neighbors to reduce side reactions mediated via G-quartet formation. In other examples, unnatural bases, or peptide nucleic acids, can be incorporated in the anchor or the bifunctional linker to modify its properties.

Methods of designing and synthesizing anchors of use in the disclosed methods are described, e.g., in PCT Publication No. WO 98/24098, incorporated herein by reference. In some examples, a set of anchors which are substantially dissimilar from one other is desirable. An exemplary algorithm for obtaining a set of dissimilar anchors is as follows:

1) The set size is defined. In some embodiments, 16, 24, 36, 48, 49, 64, 81, 96, and 100 constitute useful sizes.

2) The overall sequence structure of the anchor set is defined. The length and base composition as described above are used to define such parameters. In general, the number of G bases and C bases are held equal as are the number of A bases and T bases. This equality optimizes the configurational diversity of the final sets. Thus, such sets will be described by the equation $G_n C_n A_m T_m$.

3) For a set structure defined by m and n, a random number generator is employed to produce a set of random sequence isomers.

4) One member of the random sequence set is selected to be used as element #1 of the set.

5) The maximum similarity allowable among set members is defined. Similarity is defined in terms of local pair-wise base comparison. For example, when two oligomer strands of identical length n are aligned such that 5' and 3' ends are in register, the lack of mismatches refers to the situation where at all positions 1-n, bases in the two strands are identical. Complete mismatching refers to the situation wherein at all positions 1-n, bases in the two strands are different. For example, a useful maximum similarity might be 10 or more mismatches within a set of 16, 16 mer capture probes.

6) A second member of the random sequence set is selected and its similarity to element #1 is determined. If element #2 possesses less than the maximum allowable similarity to element #1, it will be kept in the set. If element #2 possesses greater than the maximum allowable similarity, it is discarded and a new sequence is chosen for comparison. This process is repeated until a second element has been determined.

7) In a sequential manner, additional members of the random sequence set are chosen which satisfy the dissimilarity constraints with respect to all previously selected elements.

In other examples where the capture molecule includes at least one nucleic acid capture probe, having a sequence that is complementary to at least a portion of an NPP or NPPF (or amplicon thereof), such as complementary to all or a portion of a flanking region of an NPPF amplicon. For example, the nucleic acid capture probe can include a region that is complementary to the NPP or NPPF (or amplicon thereof), and may include a region that is not (such as a region that permits attachment of the probe to a surface). The nucleic acid capture probe can be directly attached to a surface. For example, the nucleic acid capture probe can include an amine for covalent attachment to a surface. In some examples, an nucleic acid capture probe is an oligonucleotide of at least 8 nucleotides in length, such as at least 10, at least 15, at least 20, at least 30, at least 50, or at least 100 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). One skilled in the art will appreciate that the region of the nucleic acid capture probe complementary to a region of the NPP or NPPF (or amplicon thereof) need not be 100% complementary, as long as hybridization can occur between the nucleic acid capture probe and appropriate NPP or NPPF (or amplicon thereof). In some examples, the region of the nucleic acid capture probe complementary to a region of the NPP or NPPF (or amplicon thereof) is at least 8 nucleotides in length, such as at least 8, at least 10, at least 15, at least 20, at least 30, at least 50, or at least 100 nucleotides in length (for example, about 8 to 100, 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides in length).

In some examples, the sample containing NPPs or NPPs (or amplicons thereof) is denatured prior to contacting with the surface of the array (for example by heating to 95° C. for 5 minutes and rapidly chilling the sample on ice). In some examples, the sample containing NPPs or NPPFs (or amplicons thereof) is adjusted prior to contacting with the surface (for example to adjust the concentration of salt or formamide). The sample containing NPPs or NPPFs (or amplicons thereof) is incubated with the surface (for example, an array or beads) for a sufficient period of time for the NPPs or NPPFs (or amplicons thereof) to specifically bind (for example, hybridize) to the capture molecule. In some examples, the incubation of the sample with the surface at about 37° C. to about 65° C. (for example, about 45° C. to about 60° C., or about 50° C. to about 60° C., such as 50° C.) for at least 1 hours (for example 1 to 8 hours, 1 to 36 hours, 12 to 24 hours, or 16 to 24 hours, or overnight) to allow the NPPs or NPPFs (or amplicons thereof) to hybridize to the capture molecule. The capture time can be shorted, for example if using microfluidic or macrofluidic devices, lateral flow devices, or by reducing diffusion and using active flow or mixing.

Some of the surfaces (or substrates) which can be used in the disclosed methods are readily available from commercial suppliers. In some embodiments, the surface is a 96-, 384-, or 1536-well microtiter plate, such as modified plates sold by Corning Costar. In other embodiments, a substrate includes one or more beads (such as a population of beads that can be differentiated by size or color, for example by flow cytometry). Alternatively, a surface comprising wells which, in turn, comprise indentations or "dimples" can be formed by micromachining a substance such as aluminum or steel to prepare a mold, then microinjecting plastic or a similar material into the mold to form a structure. Alternatively, a structure comprised of glass, plastic, ceramic, or the like, can be assembled. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. The divider on the surface separating different reactions can also be a coated surface to which solutions will not adhere, or a nanostructure, or simply be individual drops, or capillaries or microfluidic channels or locations. In some examples, the base is a flat piece of material (for example glass or plastic), in, for example, the shape of the lower portion of a typical microplate used for a biochemical assay. The top surface of the base can be flat, or can be formed with indentations that will align with the subdivider shape to provide full subdivisions, or wells, within each sample well. The three pieces can be joined by standard procedures, for example the procedures used in the assembly of silicon wafers.

A wide variety of array formats for arrangement of the anchors can be employed in accordance with the present disclosure. One suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate.

In one embodiment, preformed nucleic acid anchors (e.g., oligonucleotide anchors) or nucleic acid capture probes having a sequence complementary to at least a portion of an NPP or NPPF (or amplicon thereof), can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al. (1996). U.S. Pat. No. 5,545,531; Fodor et al. (1996). U.S. Pat. No. 5,510,270; Zanzucchi et al. (1997). U.S. Pat. No. 5,643,738; Brennan (1995). U.S. Pat. No. 5,474,796; PCT WO 92/10092; PCT WO 90/15070). Oligonucleotide anchors or probes can be placed on top of the surface of a test region or can be, for example in the case of a polyacrylamide gel pad, imbedded within the surface in such a manner that some of the anchor or probe protrudes from the gel structure into aqueous portions within the gel and gel surface and is available for interactions with a linker, NPP, NPPF (or amplicons thereof). This is true for permeable surfaces and partially permeable surfaces, such as a surface where the first portion, such as the area of the surface in contact with the solutions containing bifunctional linkers, NPPs, or NPPFs is permeable but a second portion, such as at some distance into the surface, is not permeable. In one embodiment, preformed oligonucleotide anchors or probes are derivatized at the 5' end with a free amino group; dissolved at a concentration routinely determined empirically (e.g., about 1 µM) in a buffer such as 50 mM phosphate buffer, pH 8.5 and 1 mM EDTA; and distributed with a Pixus nanojet dispenser (Cartesian Technologies) in droplets of about 10.4 nanoliters onto specific locations within a test well whose upper surface is that of a fresh, dry DNA Bind plate (Corning Costar). Depending on the relative rate of oligonucleotide attachment and evaporation, it may be required to control the humidity in the wells during preparation. In another embodiment, oligonucleotide anchors or probes can be synthesized directly on the surface of a test region, using conventional methods such as, for example, light-activated deprotection of growing oligonucleotide chains (for example, in conjunction with the use of a site directing "mask") or by patterned dispensing of nanoliter droplets of deactivating compound using a nanojet dispenser. Deprotection of all growing oligonucleotides that are to receive a single nucleotide can be done, for example, and the nucleotide then added across the surface. In another embodiment, oligonucleotide anchors or probes are attached to the surface via the 3' ends of the oligonucleotides, using conventional methodology.

g. Detection of NPPs or NPPFs Utilizing Alternative Methods

In some embodiments, following hybridization, nuclease treatment, and optional amplification, the NPPs or NPPFs (or amplicons thereof) are detected utilizing alternative methods, such as high-throughput platforms. In some examples, NPPs or NPPFs (or amplicons thereof) are detected utilizing gel electrophoresis, chromatography, mass spectrometry, sequencing, conventional microarray analysis, detected during amplification, or hybrid capture. In some embodiments, the NPPs or NPPFs (or amplicons thereof) do not include a detectable label and indirect detection methods are utilized. Such methods are known to one of skill in the art and include, but are not limited to, those described herein.

In one example, NPPs or NPPFs (or amplicons thereof) are detected utilizing a bead-based assay, such as a bead array. One example of a bead-based assay utilizes X-MAP® beads (Luminex, Austin, Tex.), such as a QBEAD assay. In some examples, the NPPs or NPPFs (or amplicons thereof) are captured on X-MAP® beads or other beads by hybridization to an oligonucleotide associated with the beads (for example about 1 hour at about 50° C.). The detectable label included in the NPPs or NPPFs (or amplicons thereof) can be detected, for example by flow cytometry (such as utilizing a Luminex 200, Flexmap 3D, or other suitable instrument).

In another example, NPPs or NPPFs (or amplicons thereof) are detected utilizing a standard microarray. One example of such an array is a Nimblegen microarray (Nimblegen, Madison, Wis.). In some examples, the NPPs or NPPFs (or amplicons thereof) are hybridized to an array including oligonucleotides that specifically bind to the NPPs or NPPFs (or amplicons thereof). The detectable label included in the NPPs or NPPFs (or amplicons thereof) can be detected.

In some examples, NPPs or NPPFs (or amplicons thereof) are detected with a "bar code" assay. One example of such as assay is nCounter® Analysis System (Nanostring Technologies, Seattle, Wash.). In some examples, the NPPs or NPPFs (or amplicons thereof) are hybridized to a probe including one or more color coded tags (a "bar-code"). Detection of the color coded tags provides identification of the NPPs or NPPFs (or amplicons thereof). See, e.g., WO 07/0761282; WO 07/076129; WO 07/139 h. Sequencing of Amplicons (qNPS)

In some examples, the resulting NPPs or NPPFs (or amplicons thereof) are sequenced, for example by sequencing the entire NPP or NPPF (or amplicons thereof), or a portion thereof (such as an amount sufficient to permit identification of the target nucleic acid molecule). The disclosure is not limited to a particular sequencing method. In some examples, multiple different NPPs or NPPFs (or amplicons thereof) are sequenced in a single reaction. In one example, an experiment tag of the NPPs or NPPFs (or amplicons thereof), which can be designed to correspond to a particular target sequence, can be sequenced. Thus, if the 3' end of the NPPF amplicon has a sequence at the terminal 2 to 25 nucleotides (such as the terminal 2 to 5 or 2 to 7, for example the terminal 2, 3, 4, 5, 6, 7, 8, 9, or 10 nucleotides) which represent a unique sequence for each target measured, then this is all of the NPPF amplicon that needs to be sequenced to identify the target, and by counting the number of such experiment tags sequenced, the amount of each target in the sample can be determined.

In one example, the resulting NPPs or NPPFs (or amplicons thereof), such as one composed of DNA, is sequenced using the chain termination method. The resulting fragments are size-separated, for example by electrophoresis in a slab polyacrylamide gel, or in a narrow glass tube (capillary) filled with a viscous polymer. An alternative method is dye terminator sequencing. In another example pyrosequencing is used, such as the methods commercialized by Biotage (for low throughput sequencing) and 454 Life Sciences (for high-throughput sequencing). In another example, the NPPs or NPPFs (or amplicons thereof) are sequenced using a bridge PCR (e.g., Illumina®) (e.g., HiSeq) or Ion Torrent®, 454®, Helicos®, PacBio®, Solid® (Applied Vioasystems) or any number of other commercial sequencing systems. Sequencing adapters (such as a poly-A or poly T tails present on the NPPs or NPPFs (or amplicons thereof), for example introduced using PCR) are used for capture.

6. Direct Quantitative Nuclease Protection Sequencing (qNPS)

Figure 9A:
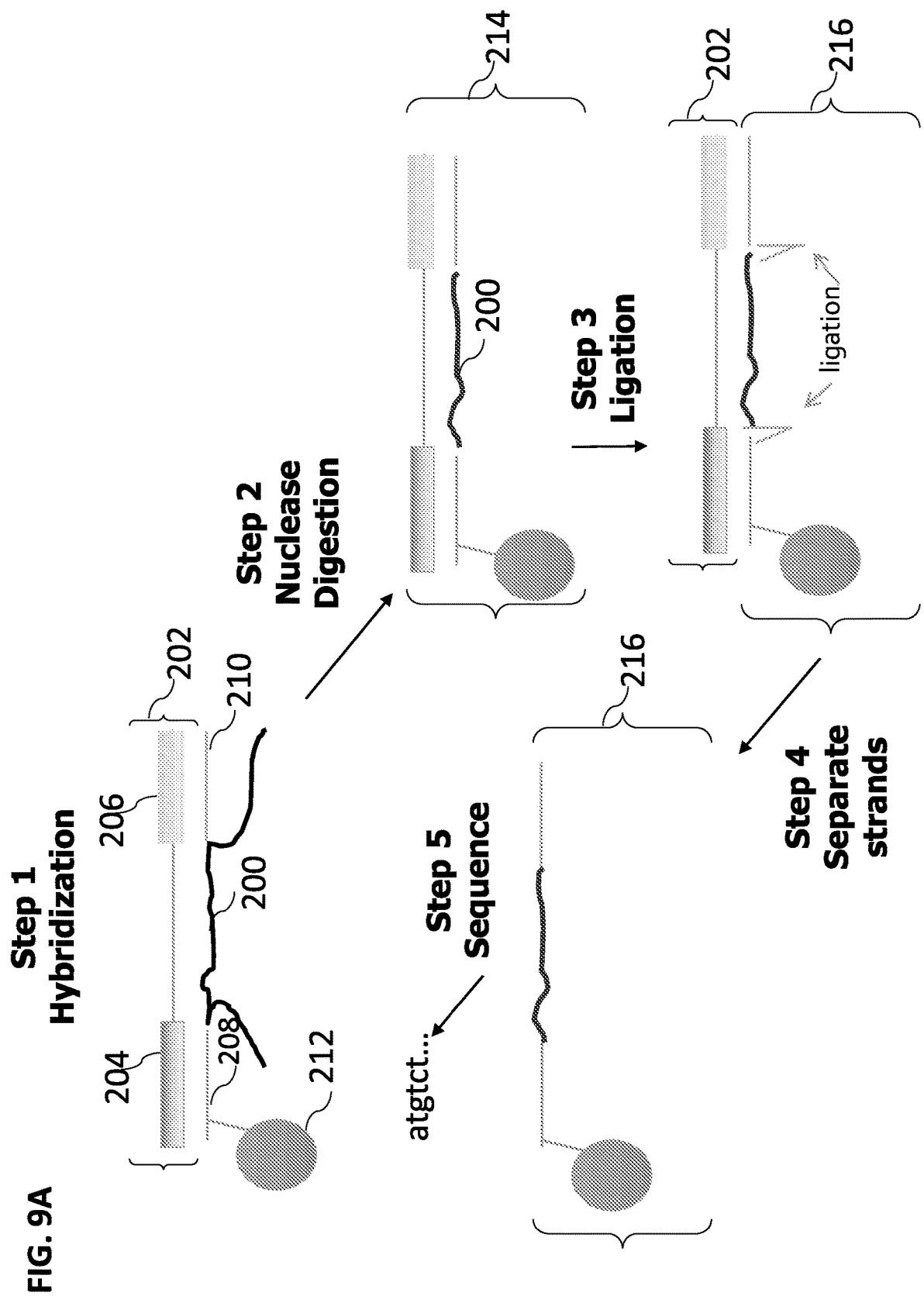

In some examples, the nucleic acid molecules in the sample whose expression is to be measured are detected in the sample utilizing an alternative of the quantitative nuclease protection assay described above, for example as described in U.S. Provisional Application No. 62/294,143 filed Feb. 11, 2016 (herein incorporated by reference) (FIG. 9A). This method also uses NPPFs and CFSs, but instead of detecting or sequencing the NPPF surrogate, this method allows for direct sequencing of a target nucleic acid molecule.

The methods include contacting the sample with at least one NPPF under conditions sufficient for the NPPF to specifically bind to or hybridize to the target nucleic acid molecule. If the NPPF includes a flanking sequence at both the 5'-end and 3'-end, in some examples the sequence of each NPPF is different and not complementary to each other. In one example, the NPPF (for example in one or both flanking sequences and/or the sequence of the region complementary to all or a portion of the target nucleic acid molecule) includes at least one dUTP, such as at least two, at least three, at least four, or at least five dUTPs. In one example, all of the "Ts" in an NPPF are replaced by "U". The presence of such bases allows the single stranded NPPF to be degraded or destroyed with uracil DNA deglycosylase (UDG) in later step (e.g., after denaturation of the NPPF from the ligated target, but before sequencing, for example before or during amplification of a ligated target).

The flanking sequence(s) are complementary to CFSs. In some examples, at least one flanking sequence includes at least one dUTP. In some examples, the NPPF includes two flanking sequences, each having at least one dUTP. In some examples, the NPPF includes two flanking sequences, but only one has at least one dUTP. In some examples, the NPPF includes a single flanking sequence having at least one dUTP. In some examples, the location of the dUTP is close to the sequence complementary to a region of the target nucleic acid molecule, such as 1, 2, 3, 4, 5, bases away from (e.g., within 1, 2, 3, 4, 5, bases of) the sequence complementary to a region of the target nucleic acid molecule. In some examples, the location of the dUTP is at least two bases (such at least 3, at least 4, or at least 5 bases) away from the sequence complementary to a region of the target nucleic acid molecule.

The methods further include contacting the sample with at least one nucleic acid molecule having complementarity to the flanking sequence (CFS) under conditions sufficient for the CFS to specifically bind or hybridize to the flanking sequence of the NPPF. For example, if the NPPF has a 5'-flanking sequence, the sample is contacted with a nucleic acid molecule having sequence complementarity to the 5'-flanking sequence (5CFS) and a 5'-end phosphate, under conditions sufficient for the 5'-flanking sequence to specifically bind to the 5CFS. Similarly, if the NPPF has a 3'-flanking sequence, the sample is contacted with a nucleic acid molecule having sequence complementarity to the 3'-flanking sequence (3CFS) under conditions sufficient for the 3'-flanking sequence to specifically bind to the 3CFS. In one example, at least one of the 3CFS and the 5CFS includes a capture moiety that permits capture, separation, retrieval, or isolation of a target sequence. One skilled in the art will appreciate that instead of using a single CFS to protect a flanking sequence, multiple CFSs can be used to protect a flanking sequence (e.g., multiple 5CFSs can be used to protect a 5'-flanking sequence). In some examples, the target nucleic acid molecule is DNA, and the 5CFS and the 3CFS are DNA, or the 5CFS is DNA and the 3CFS is RNA. In some examples, the target nucleic acid molecule is RNA, and the 5CFS is DNA and the 3CFS is RNA or the 5CFS is RNA and the 3CFS is RNA. In some examples, the target nucleic acid molecule is a RNA or DNA, and the 5CFS and/or the 3CFS is an RNA-DNA hybrid oligo, for example wherein the 5' base or bases of the 5CFS and/or the 3' base or bases of the 3CFS are RNA, and the remainder of the 5CFS and 3CFS are DNA.

This results in the generation of NPPF molecules that have bound thereto a target nucleic acid molecule (or portion thereof), as well as the CFS(s), thereby generating a double-stranded molecule that includes bases of the NPPF engaged in hybridization to a complementary base on the target and CFS. The CFS(s) hybridizes to and thus protects its corresponding flanking sequence from digestion with the nuclease in subsequent steps. In some examples, each CFS is the exact length of its corresponding flanking sequence. In some examples, the CFS is completely complementary to its corresponding flanking sequence. However, one skilled in the art will appreciate that the 3'-end of a 5CFS that protects a 5'-end flanking sequence or the 5'-end of a 3CFS that protects the 3'-end flanking sequence can have a difference, such as one nucleotide at each of these positions.

After allowing the target nucleic acid molecule and the CFS(s) to bind to the NPPFs, the method further includes contacting the sample with a nuclease specific for single-stranded (ss) nucleic acid molecules or ss regions of a nucleic acid molecule, such as S1 nuclease, under conditions sufficient to remove nucleic acid bases that are not hybridized to a complementary base. Thus for example, NPPFs that have not bound target nucleic acid molecule or CFSs, as well as unbound target nucleic acid molecules, other ss nucleic acid molecules in the sample, and unbound CFSs, are degraded. This generates a digested sample that includes intact NPPFs present as double stranded adducts hybridized to 5CFS, 3CFS, or both, and a portion of the target nucleic acid. In some examples, for example if the NPPF is composed of DNA, the nuclease can include an exonuclease, an endonuclease, or a combination thereof.

Subsequently, the CFS(s) can be ligated to the target nucleic acid, for example the 5'-phosphate of the 5CFS is ligated to the 3'-end of the target nucleic acid molecule, and the 3'-end of the 3CFS is ligated to the 5'-end of the target nucleic acid molecule, thereby generating a ligated target nucleic acid molecule (referred to herein as a ligated target).

The double-stranded NPPF:ligated target nucleic acid molecule is separated into ss nucleic acid molecules (for example by heating or increasing the pH of the sample), thereby generating a mixture of ss NPPFs and ss ligated target nucleic acid molecules. The ss ligated target nucleic acid molecules are optionally retrieved, for example by capturing it, for example by hybridization or use of a capture moiety (e.g., on the 5CFS or 3CFS). In some examples, the mixture of ss NPPFs and ss ligated target nucleic acid molecules are incubated with uracil DNA deglycosylase (UDG) under conditions sufficient for degrading or destroying the ss NPPFs having at least one dUTP.

The methods can include one or more steps that allow for capture or retrieval of the target to be sequenced, for example by use of the NPPF, 5CFS or 3CFS. For example, as shown in FIGS. 9B-9D, such capture can occur during hybridization, following nuclease digestion, or following hybridization, but prior to ligation. FIGS. 9A and 9C show an example where the capture is done after nuclease digestion. Furthermore, additional capture steps can be included, for example following ligation. In one example, the NPPF, 5CFS or 3CFS is attached to a solid substrate (such as a multi-well plate), allowing for molecules to be captured when they hybridize to the anchored NPPF, 5CFS or 3CFS. In another example, a capture moiety (such as a particle or label attached to the target, NPPF, 5CFS or 3CFS) can be used to allow for physical separation of molecules attached or hybridized to the molecule containing the capture moiety from the other components of the sample. Depending on the method of capture, such methods can include centrifugation to collect solid capture moieties, magnetic bead capture, binding or hybridization to a solid support, filtration, etc. In addition, such capture steps can include washing the captured nucleic acid molecules (thereby allowing uncaptured molecules, such as non-hybridized NPPFs and non-hybridized CFS, to be separated or removed). Such methods can include releasing the captured nucleic acid molecules from a solid support, such as a well of a multiwell plate or a single-reaction tube or vessel, or the captured nucleic acid molecules can remain affixed to or within the solid support. In some examples, this step includes centrifugation, for example to capture the target nucleic acid molecule to the bottom of a vessel or tube, and washing to allow removal of undesired or unneeded agents. In some examples, this step includes magnetic bead capture of the target nucleic acid molecule, and washing to allow removal of undesired or unneeded agents. In some examples, this step includes filtration to capture the target nucleic acid molecule, and washing to allow removal of undesired or unneeded agents. This step can include washing the target nucleic acid molecule, which in some examples removes agents no longer needed (e.g., the nuclease) and/or permits the target nucleic acid molecule to be suspended in another solution, which may facilitate one or more next steps in a particular method embodiment.

In some examples, multiple steps of the method (such as two, three, or four of the steps shown in FIG. 9A) are performed in the same vessel or container. For example, the disclosed methods allow the desired component(s) to remain in the same vessel for multiple steps, while undesired or unneeded components are removed (e.g., using repeated capture and washing steps). For example, the sample to be analyzed can be lysed in a vessel. Appropriate NPPFs and CFSs are added to that vessel, the nuclease added to that vessel, and the ds nucleic acid molecule captured in the vessel (e.g., with magnetic beads drawn to the bottom of the vessel). The captured ds nucleic acid molecule is washed to remove undesired agents, and desired buffers or reagents added to the vessel (e.g., a ligase buffer). The ss ligated target nucleic acid molecules can then be captured in the vessel, and washed.

The ligated target nucleic acid molecules are optionally amplified, for example using PCR amplification. Such methods can be used to add an experiment tag and/or sequence adaptor to the ligated target, and/or to increase the number of copies of the ligated target. At least a portion of the ss ligated target nucleic acid molecule (or amplicon thereof) is sequenced, thereby determining the sequence of the at least one target nucleic acid molecule in the sample. In some examples, the target nucleic acid molecules are RNA, and the method includes reverse transcribing them into DNA prior to sequencing.

Ligated targets can be amplified using one or more amplification primers, thereby generating ligated target amplicons. At least one amplification primer includes a region that is complementary to a CFS ligated to the target. In some examples, the target is ligated to a 5CFS at its 5'-end and to a 3CFS at its 3'-end, and two amplification primers are used, wherein one amplification primer has a region that is complementary to a region of the 5CFS and the other amplification primer has a region that is complementary to a region of the 3CFS. In some examples, the target is ligated to either a 5CFS or a 3CFS at its 5'-end and 3'-end, respectively, and one amplification primer is used (for example using rapid amplification or cDNA ends), wherein the amplification primer has a region that is complementary to a region of the 5CFS or 3CFS. One or both of the amplification primers can include a sequence that permits attachment of an experiment tag and/or sequencing adaptor to the ligated target amplicon during the amplification, and one or both primers can be labeled to permit labeling of the NPPF amplicon. In some examples, both an experiment tag and a sequencing adaptor are added, for example at opposite ends of the ligated target amplicon. For example, the use of such primers can generate an experiment tag and/or sequence adaptor extending from the 5'-end or 3'-end of the ligated target amplicon, or from both the 3'-end and 5'-end to increase the degree of multiplexing possible. The experiment tag can include a unique nucleic acid sequence that permits identification of a sample, subject, or target nucleic acid sequence. The sequencing adaptor can include a nucleic acid sequence that permits capture of the resulting ligated target amplicon onto a sequencing platform. In some examples, primers are removed from the mixture prior to sequencing.

The ligated target or ligated target amplicons (or portion thereof) is sequenced, for example using the methods described above. Any method can be used to sequence the ligated target or ligated target amplicons, and the disclosure is not limited to particular sequencing methods. In some examples, the sequencing method used is chain termination sequencing, dye termination sequencing, pyrosequencing, nanopore sequencing, or massively parallel sequencing (also called, next-generation sequencing (or NGS)), which is exemplified by ThermoFisher Ion Torrent™ Personal Genome Machine (PGM™), Illumina-branded NGS sequencers (e.g., MiSeq™, HiSeq™) (or as otherwise derived from Solexa™ sequencing), and 454 sequencing available from Roche Life Sciences. In some examples, single molecule sequencing is used. In some examples, the method also includes comparing the obtained target sequence to a sequence database, for example to determine if a target mutation is present or absent. In some examples, the method includes determining the number of (e.g., counting) each target sequence obtained.

FIG. 9A is a schematic diagram showing an overview of an embodiment for using NPPFs 202 to sequence a nucleic acid molecule for the disclosed methods. As shown in step 1, a sample (such as one known or suspected of containing a target nucleic acid, 200 that has been treated with a sample disruption or lysis buffer (e.g., lysed or otherwise treated to make nucleic acids accessible) is contacted or incubated with a plurality of nuclease protection probes having one or more flanking sequences (NPPFs) 202 (shown here with both a 5'- and a 3'-flanking sequence, 204 and 206, respectively), including at least one NPPF which specifically binds to a first target nucleic acid 200 (such as a target DNA or RNA). The reaction can also include other NPPFs which specifically bind to a second target nucleic acid, and so on. For example, the method can use one or more different NPPFs designed to be specific for each unique target nucleic acid molecule, such as NPPFs specific for each of CD47, CD86, ENTPD1, FOXP1, FUT8, IL16, ITPKB, LRMP, MME, NF2, PIM1, PTPRC, REL, STAT3, TNFRSF8, and TYMS. In some examples, the plurality of NPPFs can include more than one (such as 2, 3, 4, 5, 10, 20, 50 or more) NPPFs specific for a single target nucleic acid molecule (which is referred to as a tiled set of NPPFs). The reaction also includes nucleic acid molecules that are complementary to the flanking sequences (CFS) 208, 210. Thus, if the NPPF has a 5'-flanking sequence 204, the reaction will include a sequence complementary to the 5'-flanking sequence (5CFS) 208 and if the NPPF has a 3'-flanking sequence 206, the reaction will include a sequence complementary to the 3'-flanking sequence (3CFS) 210. In some examples, the 5CFS 208 has a 5'-end phosphate, which allows for ligation to the target 200 at a later step. In some examples, at least one of the CFSs includes a capture moiety 212, which permits retrieval of the target at the desired time. Although the capture moiety 212 is shown in the 5CFS 208, it will be appreciated that in embodiments where it is present, it can alternatively be on the 3CFS 210, the NPPF 202 or the target 200. One skilled in the art will appreciate that the sequence of the CFSs will vary depending on the flanking sequence present. In addition, more than one CFS can be used to ensure a flanking region is protected (e.g., at least two CFSs can use that bind to different regions of a single flanking sequence). The CFS can include natural or unnatural bases.

The capture moiety 212 in FIG. 2A is optional, or can be on the 3CFS 210 or target 200. The sample, NPPFs and CFSs are incubated under conditions sufficient for NPPFs to specifically bind to (e.g., hybridize to) their respective target nucleic acid molecule, and for CFSs to bind to (e.g., hybridize to) their complementary sequence on the NPPF flanking sequence. In some examples, the CFSs 208, 210 are added in excess of the NPPFs 202, for example at least 5-fold more CFSs than NPPFs (molar excess), such as at least 6-fold, at least 7-fold, at least 8-fold, at least 9-fold, at least 10-fold, at least 20-fold, at least 40-fold, at least 50-fold, or at least 100-fold more CFSs than the NPPFs. In some examples, the NPPFs 202 are added in excess of the total nucleic acid molecules in the sample, for example at least 50-fold more NPPF than total nucleic acid molecules in the sample (molar excess), such as at least 75-fold, at least 100-fold, at least 200-fold, at least 500-fold, or at least 1000-fold more NPPF than the total nucleic acid molecules in the sample. For experimental convenience a similar concentration of each NPPF can be included to make a cocktail, such that for the most abundant nucleic acid target measured there will be at least 50-fold more NPPF for that nucleic acid target, such as an at least 100-fold excess. The actual excess and total amount of all NPPFs used is limited only by the capacity of the nuclease (e.g., S1 nuclease) to destroy all NPPF's that are not hybridized to target nucleic acid targets. In some examples the reaction is heated, for example incubated for overnight (such as for 16 hours) at 50° C.

As shown in step 2 in FIG. 9A, after allowing the binding/hybridization reactions to occur, the sample is contacted with a reagent (such as, a nuclease) specific for single-stranded (ss) nucleic acid molecules under conditions sufficient to remove (or digest) ss nucleic acid molecules, such as unbound nucleic acid molecules (such as unbound NPPFs, unbound CFSs, and unbound target nucleic acid molecules, or portions of such molecules that remain single stranded, such as portions of a target nucleic acid molecule not bound to the NPPF). This results in the generation of a ds NPPF/target hybridized complex (or duplex) 214. As shown in FIG. 9A, incubation of the sample with a nuclease specific for ss nucleic acid molecules results in degradation of any ss nucleic acid molecules present, leaving intact double-stranded nucleic acid molecules, including NPPFs that have bound thereto and CFSs and target nucleic acid molecule. For example, the reaction can be incubated at 50° C. for 1.5 hours with S1 nuclease (though hydrolysis can occur at other temperatures and be carried out for other periods of time, and in part that the time and temperature required will be a function of the amount of nuclease, and on the amount of nucleic acid required to be hydrolyzed, as well as the $T_m$ of the double-stranded region being protected).

As shown in step 3 of FIG. 9A, the NPPF/target complex 214 (which is captured or retrieved at some time prior to the ligation, see FIGS. 9B-9D, and non-hybridized material removed), is exposed to ligation conditions, that allow the target sequence 200 (which can be DNA or RNA) to be ligated to the CFSs (e.g., to the 5CFS 208, 3CFS 210, or both), thereby generating a ligated target 216. Any ligase capable of covalently joining the target sequence and CFS(s) can be used, such as a DNA or RNA ligase, such as a T4 DNA ligase, T4 RNA ligase, or Taq ligase (thus, such ligases can be present in a kit provided herein, such as alone or in a ligation buffer). The ligase used may depend on the nucleotide (ribonucleotide or deoxyribonucleotide) present on the CFS that is closest to the target sequence. In some examples, a ligase is diluted in a buffer (such as one containing essential cofactors such as NAD+ or ATP, a buffering agent, and cations are added to the mixture containing NPPF/target duplexes and incubated at about 4° C.-60° C. (depending on the ligase) (such as at least 4° C., at least 20° C., at least 25° C., at least 30° C., at least 37° C., at least 50° C., or at least 60° C., such as 4 to 37° C., 4 to 25° C., or 20 to 25° C.) for at least 15 minutes, at least 30 minutes, at least 1 hour, at least 2 hours, at least 4 hours, at least 6 hours, at least 12 hours, or at least 16 hours, to ligate the CFSs to the target nucleic acid molecule (wherein the CFSs and target are already hybridized to an NPPF). In one example, a buffer for T4 DNA ligase includes 50 mM Tris-HCl, pH 7.5, 10 mM $MgCl_2$, 10 mM dithiothreitol, 1 mM ATP. The 5CFS 208 can include a 5'-end phosphate, which can be ligated to the 3'-end of the target 200. The 3CFS 210 can include a 3'-end (such as a 3'-terminal nucleotide), which can be ligated to the 5'-end phosphate of the target. If only one flanking sequence is present on the NPPF, only one CFS will have been bound in the NPPF/target complex, and the target will be ligated to only one CFS. The CFSs can be DNA or RNA (or a mixture of both nucleotide types). If the CFS or target is DNA, the 5'-end phosphate donor for ligation to DNA cannot be a ribonucleotide. In one example if the target is RNA, the 5CFS 208 is DNA or RNA and the 3CFS 210 is RNA. In one example if the target is DNA, the 5CFS 208 is DNA (or at least the 5'-end nucleotide of the 5CFS 208 is a dNTP that will ligate to the 3'-end of the target) or RNA and the 3CFS 210 is RNA.

As shown in step 4 of FIG. 9A, after ligating the CFS(s) to the target, the NPPF 202 is separated from the ligated target 216. That is, the NPPF/target complex 214 (e.g., double stranded nucleic acid molecule) is separated into two single stranded nucleic acid molecules, the NPPF 202 and the ligated target 216. This step can also remove unligated nucleic acid molecules (e.g., unligated CFS). For example, the reaction can be heated or the pH altered (e.g., to result in the reaction having a basic pH) under conditions that allow the NPPF 202 to dissociate from the ligated target 216, resulting in a mixed population of single stranded NPPFs 202 and single stranded ligated targets 216. In some examples, the ligated target 216 is separated from this mixture by using the capture moiety 212 on the CFS. Capture methods described herein can be used to capture the ligated target 216. For example if the capture moiety 212 is a bead, the ligated target 216 can be retrieved using centrifugation. If the capture moiety 212 is a metal bead, the ligated target 216 can be retrieved using a magnet. If the capture moiety 212 includes a carboxyl group, the ligated target 216 can be captured using an appropriately amine-labeled solid substrate. Following capture of the ligated target 216, the remainder of the reaction (e.g., the NPPF 202) can be removed (e.g., by washing). In some examples, the ligated target 216 is captured using filtration.

As shown in step 5 of FIG. 9A, the isolated ligated target 216 (or amplicons thereof) is then sequenced. In some examples, a plurality of ligated targets are sequenced in parallel, for example simultaneously or contemporaneously. This method can thus be used to sequence a plurality of ligated target sequences.

Optionally, the ligated targets 216 are amplified (e.g., using PCR), washed, or both, prior to the sequencing. In some examples, the NPPFs 202 are degraded with uracil DNA deglycosylase (UDG), for example if at least one flanking sequence, or the capture sequence, includes dUTP. Such degradation can occur before or during the amplification. In some examples, such as if the target is RNA, a reverse transcription step can be included as part of the amplification. Thus, the resulting ligated target amplicons 226 can then be sequenced. The PCR primers or probes can include one or more experiment tags 222, 224 and/or sequencing adaptors 218, 220 (e.g., that allow the ligated targets to be sequenced by a particular sequencing platform, and thus such adaptors are complementary to capture sequences on a sequencing chip). At least a portion of the PCR primers/probes are specific for the 5CFS 208 and/or 3CFS 210. In some examples, the concentration of the primers are in excess of the ligated target 216, for example in excess by at least 10,000-fold, at least 50,000-fold, at least 100,000-fold, at least 150,000-fold, at least 200,000-fold, at least 400,000-fold, at least 500,000-fold, at least 600,000-fold, at least 800,000-fold, or at least 1,000,000-fold. In some examples, the concentration of primers 208 in the reaction is at least 200 nM (such as at least 400 nM, at least 500 nM, at least 600 nM, at least 750 nM, or at least 1000 nM).

As shown in FIGS. 9B-9D, at a point(s) prior to ligation (e.g., step 3 of FIG. 9A), the target (200 of FIG. 9A) and other molecules attached/hybridized thereto, is retrieved or captured (step 320), thus allowing for removal of the remaining agents in the sample (e.g., non-hybridized material), and addition of new reagents. In addition, capture of the target allows for subsequent washing of nucleic acid molecules hybridized or otherwise attached to the target (e.g. to inactivate or remove residual enzymes).

In one example, the target is retrieved or captured at hybridization (FIG. 9B). As shown in FIG. 9B, following optional denaturation 300, the sample containing the target is incubated with the NPPF and CFS(s) under conditions that permit hybridization 310, thereby producing a hybridized complex. In such an example, the target, along with the NPPF to which it will hybridize, and the CFS(s) that can hybridize to the NPPF, are incubated in the presence of a solid support containing a material that allows capture of the resulting hybridized complex 320. For example, the capture moiety (e.g., 212 in FIG. 9A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support allows the hybridized complex to bind to the solid support (e.g., because the NPPF will hybridize to the CFS attached to the solid support, and the target and other CFS will hybridize to the NPPF). The method can include wash steps following the hybridization. One or more of the subsequent steps, such as the nuclease digestion 330, washes 340, ligation 350, UDG digestion 370 (optional, only if the NPPF includes dUTP), and/or the PCR amplification 380 can take place in the presence of the solid support, which allows reagents to be removed and added to the captured target.

In one example, the target is retrieved or captured following nuclease treatment (e.g., after step 2 in FIG. 9A), but before ligation (e.g., before step 3 in FIG. 9A) (FIG. 9C). As shown in FIG. 9C, following optional denaturation 400, hybridization 410, and nuclease digestion 430, which produces a NPPF/target complex (214 in FIG. 9A), the NPPF/target complex is retrieved from the sample mixture at step 420. In some examples, the NPPF/target complex is retrieved by using a capture moiety on the CFS, without separating the NPPF/target duplex into ss nucleic acid molecules. For example, the capture moiety (e.g., 212 in FIG. 9A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support is part of the NPPF/target complex, which allows for its capture or retrieval. The method can include wash steps 440 following the retrieval. One or more of the subsequent steps, such as the ligation 450, washing 460, UDG digestion 470 (optional, only if the NPPF includes dUTP), and/or the PCR amplification 480 can take place in the presence of the solid support, which allows reagents to be removed and added to the captured target.

In one example, the target is retrieved or captured following hybridization (e.g., after step 1 in FIG. 9A), but before nuclease digestion (e.g., before step 2 in FIG. 9A) (FIG. 9D). As shown in FIG. 9D, following optional denaturation 500 and hybridization 510, which produces a hybridized complex, the resulting hybridized complex is retrieved from the sample mixture at step 520. In some examples, the hybridized complex is retrieved by using a capture moiety on the CFS. For example, the capture moiety (e.g., 212 in FIG. 9A) present on the 3CSF, 5CSF, and/or NPPF can be utilized as the solid support. For example if the capture moiety is a bead or plate (e.g., attached to a CFS using a carboxy-amine linkage, such as an amino group on the CFS and a carboxy on the bead), the solid support is the bead or plate. In this case, the capture moiety/solid support is part of the hybridized complex, which allows for its capture or retrieval. The method can include wash steps following the retrieval. One or more of the subsequent steps, such as the nuclease digestion 530, ligation 550, washing 540, 560, UDG digestion 570 (optional, only if the NPPF includes dUTP), and/or the PCR amplification 580 can take place in the presence of the solid support, which allows reagents to be removed and added to the captured target.

B. Proteins for Detecting Gene Expression

In some embodiments of the disclosed methods, determining the level of gene expression in a sample includes detecting one or more proteins (for example by determining the relative or actual amounts of such proteins) in the sample. Routine methods of detecting proteins are known in the art, and the disclosure is not limited to particular methods of protein detection.

Protein gene products (e.g., those in Table 1) can be detected and the level of protein expression in the sample can be determined through novel epitopes recognized by protein-specific binding agents (such as antibodies or aptamers) specific for the target protein (such as those in Table 1) used in immunoassays, such as ELISA assays, immunoblot assays, flow cytometric assays, immunohistochemical assays, an enzyme immunoassay, radioimmuno assays, Western blot assays, immunofluorescent assays, chemiluminescent assays and other peptide detection strategies. Generally these methods utilize monoclonal or polyclonal antibodies.

Thus, in some embodiments, the level of target protein expression (such as those in Table 1) present in the biological sample and thus the amount of protein expressed is detected using a target protein specific binding agent, such as an antibody of fragment thereof, which can be detectably labeled. In some embodiments, the specific binding agent is an antibody, such as a polyclonal or monoclonal antibody, that specifically binds to the target protein (such as those in Table 1). Thus in certain embodiments, determining the level or amount of protein in a biological sample includes contacting a sample from the subject with a protein specific binding agent (such as an antibody that specifically binds a protein shown in Table 1), detecting whether the binding agent is bound by the sample, and thereby measuring the amount of protein present in the sample. In one embodiment, the specific binding agent is a monoclonal or polyclonal antibody that specifically binds to the target protein (such as those in Table 1). One skilled in the art will appreciate that there are commercial sources for antibodies to target proteins, such as those in Table 1.

The presence of a target protein (such as those in Table 1) can be detected with multiple specific binding agents, such as one, two, three, or more specific binding agents. Thus, the methods can utilize more than one antibody. In some embodiments, one of the antibodies is attached to a solid support, such as a multiwell plate (such as, a microtiter plate), bead, membrane or the like. In practice, microtiter plates may conveniently be utilized as the solid phase. However, antibody reactions also can be conducted in a liquid phase.

In some examples, the method can include contacting the sample with a second antibody that specifically binds to the first antibody that specifically binds to the target protein (such as those in Table 1). In some examples, the second antibody is detectably labeled, for example with a fluorophore (such as FITC, PE, a fluorescent protein, and the like), an enzyme (such as HRP), a radiolabel, or a nanoparticle (such as a gold particle or a semiconductor nanocrystal, such as a quantum dot (QDOT®)). In this method, an enzyme which is bound to the antibody will react with an appropriate substrate, such as a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme.

Detection can also be accomplished by visual comparison of the extent of enzymatic reaction of a substrate in comparison with similarly prepared standards. It is also possible to label the antibody with a fluorescent compound. Exemplary fluorescent labeling compounds include fluorescein isothiocyanate, rhodamine, phycoerythrin, phycocyanin, allophycocyanin, o-phthaldehyde, Cy3, Cy5, Cy7, tetramethylrhodamine isothiocyanate, phycoerythrin, allophycocyanins, Texas Red and fluorescamine. The antibody can also be detectably labeled using fluorescence emitting metals such as $^{152}$Eu, or others of the lanthanide series. Other metal compounds that can be conjugated to the antibodies include, but are not limited to, ferritin, colloidal gold, such as colloidal superparamagnetic beads. These metals can be attached to the antibody using such metal chelating groups as diethylenetriaminepentacetic acid (DTPA) or ethylenediaminetetraacetic acid (EDTA). The antibody also can be detectably labeled by coupling it to a chemiluminescent compound. Examples of chemiluminescent labeling compounds are luminol, isoluminol, theromatic acridinium ester, imidazole, acridinium salt and oxalate ester. Likewise, a bioluminescent compound can be used to label the antibody. In one example, the antibody is labeled with a bioluminescence compound, such as luciferin, luciferase or aequorin. Haptens that can be conjugated to the antibodies include, but are not limited to, biotin, digoxigenin, oxazalone, and nitrophenol. Radioactive compounds that can be conjugated or incorporated into the antibodies include but are not limited to technetium 99 m ($^{99}$Tc), $^{125}$I and amino acids including any radionucleotides, including but not limited to, $^{14}$C, $^{3}$H and $^{35}$S.

Generally, immunoassays for proteins (such as those in Table 1) typically include incubating a biological sample in the presence of antibody, and detecting the bound antibody by any of a number of techniques well known in the art. In one example, the biological sample (such as one containing melanocytes) can be brought in contact with, and immobilized onto, a solid phase support or carrier such as nitrocellulose or a multiwell plate, or other solid support which is capable of immobilizing cells, cell particles or soluble proteins. The support may then be washed with suitable buffers followed by treatment with the antibody that specifically binds to the target protein (such as those in Table 1). The solid phase support can then be washed with the buffer a second time to remove unbound antibody. If the antibody is directly labeled, the amount of bound label on solid support can then be detected by conventional means. If the antibody is unlabeled, a labeled second antibody, which detects that antibody that specifically binds to the target protein (such as those in Table 1) can be used.

Alternatively, antibodies are immobilized to a solid support, and then contacted with proteins isolated from a biological sample, such as a tissue biopsy, under conditions that allow the antibody and the protein to bind specifically to one another. The resulting antibody: protein complex can then be detected, for example by adding another antibody specific for the protein (thus forming an antibody:protein: antibody sandwich). If the second antibody added is labeled, the complex can be detected, or alternatively, a labeled secondary antigay can be used that is specific for the second antibody added.

A solid phase support or carrier includes materials capable of binding a sample, antigen or an antibody. Exemplary supports include glass, polystyrene, polypropylene, polyethylene, dextran, nylon, amylases, natural and modified celluloses, polyacrylamides, gabbros and magnetite. The nature of the carrier can be either soluble to some extent or insoluble. The support material may have virtually any possible structural configuration so long as the coupled molecule is capable of binding to its target (such as an antibody or protein). Thus, the support configuration may be spherical, as in a bead, or cylindrical, as in the inside surface of a test tube, or the external surface of a rod. Alternatively, the surface may be flat such as a sheet or test strip.

In one embodiment, an enzyme linked immunosorbent assay (ELISA) is utilized to detect the target protein(s). ELISA can be used to detect the presence of a protein in a sample, for example by use of an antibody that specifically binds to a target protein (such as those in Table 1). In some examples, the antibody can be linked to an enzyme, for example directly conjugated or through a secondary antibody, and a substance is added that the enzyme can convert to a detectable signal. Thus, in the case of fluorescence ELISA, when light of the appropriate wavelength is shone upon the sample, any antigen:antibody complexes will fluoresce so that the amount of antigen in the sample can be inferred through the magnitude of the fluorescence. The protein (such as proteins extracted or isolated from a melanocyte-containing sample) is usually immobilized on a solid support (for example polystyrene microtiter plate) either non-specifically (for example via adsorption to the surface) or specifically (for example via capture by another antibody specific to the same antigen, in a "sandwich" ELISA). Between each step the plate is typically washed with a mild detergent solution, such as phospho-buffered saline with or without NP40 or TWEEN to remove any proteins or antibodies that are not specifically bound. After the final wash step the plate is developed by adding an enzymatic substrate to produce a visible signal, which indicates the quantity of protein in the sample.

Detection can also be accomplished using any of a variety of other immunoassays. For example, by radioactively labeling the antibodies or antibody fragments, it is possible to detect fingerprint gene wild-type or mutant peptides through the use of a radioimmunoassay (RIA). In another example, a sensitive and specific tandem immunoradiometric assay may be used (see Shen and Tai, *J. Biol. Chem.*, 261:25, 11585-11591, 1986). The radioactive isotope can be detected by such means as the use of a gamma counter or a scintillation counter or by autoradiography.

In one example, a spectrometric method is utilized to detect or quantify an expression level of a target protein (such as those in Table 1). Exemplary spectrometric methods include mass spectrometry, nuclear magnetic resonance spectrometry, and combinations thereof. In one example, mass spectrometry is used to detect the presence of a target protein (such as those in Table 1) in a biological sample.

A target protein (such as those in Table 1) also can be detected by mass spectrometry assays coupled to immunaffinity assays, the use of matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS) sequence tag of proteins separated by two-dimensional polyacrylamide gel electrophoresis (2D-PAGE).

Quantitative mass spectroscopic methods, such as SELDI, can be used to analyze protein expression in a sample. In one example, surface-enhanced laser desorption-ionization time-of-flight (SELDI-TOF) mass spectrometry is used to detect protein expression, for example by using the ProteinChip (Ciphergen Biosystems, Palo Alto, Calif.). Such methods are well known in the art. SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as those in any of Tables 2-8. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as those in Table 1) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind a target protein (such as those in Table 1). In other examples, the chromatographic surface consists essentially of, or consists of, antibodies that specifically bind a target protein (such as those in Table 1). In some examples, the chromatographic surface includes antibodies that bind other molecules, such as normalization proteins (e.g., those in Table 1).

In another example, antibodies are immobilized onto the surface using a bacterial Fc binding support. The chromatographic surface is incubated with a sample, such as a sample of a nevus. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

Alternatively, the amount of target protein can be determined using fluorescent methods. For example, quantum dots (e.g., Qdots® label) are useful in a growing list of applications including immunohistochemistry, flow cytometry, and plate-based assays, and may therefore be used in conjunction with this disclosure. Quantum dot nanocrystals have unique optical properties including an extremely bright signal for sensitivity and quantitation; and high photostability for imaging and analysis. A single excitation source is needed, and a growing range of conjugates (e.g., antibody conjugates) makes them useful in a wide range of applications. The emission from quantum dots is narrow and symmetric, which means overlap with other colors is minimized, resulting in minimal bleed through into adjacent detection channels and attenuated crosstalk, in spite of the fact that many more colors can be used simultaneously. For example, IHC can be performed with quantum dot-conjugated secondary antibodies or streptavidin-conjugated quantum dots in combination with biotin-labeled primary or secondary antibodies.

C. Optional Assay Control Measures

Optionally, assays used to detect gene expression products (e.g., nucleic acids (such as mRNA, lncRNA) or protein) include positive and negative process control elements used to assess assay performance.

A positive control can be any known element, preferably of a similar nature to the target (e.g., RNA target, then RNA (or cDNA) positive control), that can be included in an assay (or sample) and detected in parallel with the target(s) and that does not interfere (e.g., crossreact) with such target(s) detection. In one example, the positive control is an in vitro transcript (IVT) that is run in parallel as a separate sample or is "spiked" into each sample at a known amount. IVT-specific binding agents (e.g., oligonucleotide probes, such as an NPP or NPPF)) and, if applicable, IVT-specific detection agents also are included in each assay to ensure a positive result for such in vitro transcript.

In some situations, anomalous signals may result from unexpected process-related issues that are not otherwise controlled, e.g., by analysis of normalizers; thus, in some embodiments, it is useful to include a sample-independent process control element(s) to indicate a successful or failed assay on any specimen, irrespective of the specimen stability, integrity, or input level. Method embodiments in which nucleic acid gene expression products are detected may include a known concentration of a RNA sample (e.g., in vitro transcript RNA or IVT) in every assay. Such a control element (e.g., IVT) can be measured in each assay and act as an assay process quality control.

Some disclosed method embodiments involving RNA gene expression products may, but need not, include a parallel-processed sample containing Universal Human Reference RNA. If such universal RNA sample includes all or some of the RNAs targeted for detection by the applicable assay, a positive signal can be expected for such included RNAs, which may serve as an (or another) assay process quality control.

Negative process control elements can include analyte-specific binding agents (e.g., oligonucleotides or antibodies) designed or selected to detect a gene product that is not expected to be expressed in the test sample. For example, an analyte-specific binding agent that does recognize any gene expression product in the human transcriptome or proteome may be included in a multiplexed assay (such as an oligonucleotide probe or antibody specific for a plant or insect or nematode RNA or protein, respectively, where human gene expression products are the desired targets). This negative control element should not generate signal in the applicable assay. Any above-background signal for such negative process control element is an indicator of assay failure. In one example, the negative control is ANT.

IV. Gene Expression Data

Gene expression data "contain the keys to address fundamental problems relating to the prevention and cure of diseases, biological evolution mechanisms and drug discovery" (Lu and Han, Information Systems, 28:243-268 (2003)). In some examples, distilling the information from such data is as simple as making a qualitative determination from the presence, absence or qualitative amount (e.g., high, medium, low) of one or more gene products detected. In other examples, raw gene expression data may be pre-processed (e.g., background subtracted, log transformed, and/or corrected), normalized, and/or applied in classification algorithms. However, such pre-processing of data is optional.

Many biological variables (e.g., gene expression data) do not meet the assumptions of parametric statistical tests, e.g., such variables are not normally distributed, the variances are not homogeneous, or both (Durbin et al., *Bioinformatics*, 18:S105 (2002). In some cases, transforming the data will make it fit the statistical assumptions better. In some method embodiments, useful data transformation can include (i) log transformation, which consists of taking the log of each observation, e.g., base-10 logs, base-2 logs, base-e logs (also known as natural logs); the log selection makes no difference because such logs differ by a constant factor; or variance-stabilizing transformation, e.g., as described by Durbin (supra). In specific examples, raw expression values for each biomarker detected in such method (e.g., at least two biomarkers in Table 1) are log (e.g., log 2 or log 10) transformed. When count/read expression is calculated, transformation can include total reads for each sample, this value is scaled to per million reads: gene-level reads are proportionally evaluated compared to total reads for a sample and $\log_2$ transformed resulting in log-base-2 counts per million (CPM), $$\log_2\left(\frac{r_{gi} + 0.5}{R_i + 1} \times 1{,}000{,}000\right),$$

where $r_{gi}$ is the number of sequence reads for each probe (g) and sample (i), (scaled to avoid zero counts), adjusted for the number of mapped reads (library count) for each sample ($R_i$, scaled by a constant 1 to ensure the proportional read to library size ratio is greater than zero).

V. Method Implementation

The methods, such as those involving classifiers, described herein can be implemented in numerous ways. Several representative non-limiting embodiments are described below. In some method embodiments, gene expression data is input (e.g., manually or automatically) into a computer or other device, machine or apparatus for application of the various algorithms described herein, which is particularly advantageous where a large number of gene expression data points are collected and processed. Thus, in some examples the gene expression data or probability value obtained using the disclosed methods is stored in computer memory. Other embodiments involve use of a communications infrastructure, for example the internet. Various forms of hardware, software, firmware, processors, or a combination thereof are useful to implement specific classifier and method embodiments. Software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment. The score can be a numerical score (representative of a numerical value) or a non-numerical score representative of a numerical value or range of numerical values (e.g., "A" representative of a 90-95% likelihood of an outcome).

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of a response gene, level of a reference gene product(s); normalized level of a response gene; and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, using devices such as fax back). Exemplary output receiving devices can include a display element, a printer, a facsimile device and the like. Electronic forms of transmission and/or display can include email, interactive television, and the like. In one embodiment, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility. In some examples, the method includes generating a report. In some examples the report includes an icon indicating the classification of a sample, such as "ABC" for ABC DLBCL or "GCB" for GCB DLBCL.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output). The computer processors can be processors that are typically found in personal desktop computers (e.g., IBM, Dell, Macintosh), portable computers, mainframes, minicomputers, tablets, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present disclosure.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

1. Computer-Readable Storage Media

The present disclosure also contemplates a computer-readable storage medium (e.g. CD-ROM, memory key, flash memory card, diskette, etc.) having stored thereon a program which, when executed in a computing environment, provides for implementation of algorithms to carry out all or a portion of the results of a response likelihood assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.), the program provides for transmission of data input by the user (e.g., via the internet, via an intranet, etc.) to a computing environment at a remote site. Processing or completion of processing of the data can be carried out at the remote site to generate a report. After review of the report, and completion of any needed manual intervention, to provide a complete report, the complete report can be then transmitted back to the user as an electronic document or printed document (e.g., fax or mailed paper report). The storage medium containing a program as described herein can be packaged with instructions (e.g., for program installation, use, etc.) recorded on a suitable substrate or a web address where such instructions may be obtained. The computer-readable storage medium can also be provided in combination with one or more reagents for carrying out response likelihood assessment (e.g., primers, probes, arrays, or other such kit components).

2. Output

In some embodiments, once a score for a particular sample (patient) is determined, an indication of that score can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, or other diagram), or an audible output. Thus, the output can include a report that is generated.

For example, the output can be textual (optionally, with a corresponding) score. For example, textual outputs may be "ABC" or the like, or "GCB" or the like, or "indeterminant" or the like. Such textual output can be used, for example, to provide a diagnosis of DLBCL subtype GCB or DLBCL subtype ABC, or can simply be used to assist a clinician in distinguishing subtypes ABC and GCB.

In other examples, the output is a numerical value (e.g., quantitative output), such as a predicted probability value. In additional examples, the output is a graphical representation, for example, a graph that indicates the predicted probability. In a particular example, the output (such as a graphical output) shows or provides a cut-off value or level that characterizes the sample tested as ABC or GCB. In other examples, the output is an icon, such as a "ABC" if the sample is classified as a ABC, "GCB" if the sample is classified as a GCB, or "U" or "?" if the sample is classified as unclassified (e.g., not consistent with either ABC or GCB). In some examples, the output is communicated to the user, for example by providing an output via physical, audible, or electronic means (for example by mail, telephone, facsimile transmission, email, or communication to an electronic medical record).

In some examples, the output is accompanied by guidelines for interpreting the data, for example, numerical or other limits that indicate that the DLBCL is ABC or GCB. The guidelines need not specify whether a DLBCL is ABC or GCB, although it may include such a diagnosis. The indicia in the output can, for example, include normal or abnormal ranges or a cutoff, which the recipient of the output may then use to interpret the results, for example, to arrive at a diagnosis or treatment plan. In other examples, the output can provide a recommended therapeutic regimen. In some examples, the test may include determination of other clinical information (such as determining the amount of one or more additional DLBCL biomarkers in the sample).

VI. Clinical Use of Gene Sets and Classifier Outputs

The disclosed gene sets or classifiers may result in a DLBCL sample being characterized (e.g., diagnosed) as a GCB subtype or a non-GCB subtype (such as ABC), or indeterminate. Each of these (and other possible) results is useful to the trained clinical professional. Some representative clinical uses are described in more detail below. A diagnosis or prognosis may be provided to a subject (e.g., patient or physician) by any suitable means, including, but not limited to via physical, audible, or electronic means (for example by mail, telephone, facsimile transmission, email, or communication to an electronic medical record).

A. Diagnosis Indications

A diagnosis informs a subject (e.g., patient) what disease or condition s/he has or may have. As more particularly described throughout this disclosure, any result of any disclosed method that classifies a DLBCL subtype can be provided, e.g., to a subject or health professional, as a diagnosis. Thus, a diagnosis includes determining whether a DLBCL is a GCB subtype or a non-GCB subtype (such as ABC), or indeterminant.

B. Prognostic Indications

Prognosis is the likely health outcome for a subject whose sample received a particular test result (e.g., GCB subtype or non-GCB subtype (such as ABC) of DLBCL). A poor prognosis means the long-term outlook for the subject is not good, e.g., the 1-, 2-, 3- or 5-year survival is 50% or less (e.g., 40%, 30%, 25%, 20%, 15%, 10%, 5%, 2% or 1% or less). On the other hand, a good prognosis means the long-term outlook for the subject is fair to good, e.g., the 1-, 2-, 3- or 5-year survival is greater than 30%, 40%, 50%, 60%, 70%, 75%, 80% or 90%.

Non-GCB subtype DLBCL, such as ABC subtype DLBCL, has been shown to have a poorer prognosis than GCB subtype DLBCL. Accordingly, a finding of Non-GCB subtype DLBCL, such as ABC subtype DLBCL by any of the disclosed methods can be used to predict a comparatively poor prognosis for a subject from whom the test sample is taken. Conversely, a finding of GCB subtype DLBCL by any of the disclosed methods can be used to predict a comparatively good prognosis for the corresponding subject.

C. Therapeutic (Predictive) Indications

The disclosed methods can further include selecting (or not selecting) subjects for treatment for GCB subtype DLBCL or non-GCB subtype DLBCL, such as ABC subtype DLBCL, if their corresponding sample is so subtyped. Exemplary treatment methods are provided in the section below. Thus, in one example, if the sample is determined to be GCB subtype DLBCL, the subject from whom the sample was obtained is treated with (1) a cyclophosphamide, doxorubicin, vincristine, and prednisone or prednisolone (CHOP) chemotherapy, (2) rituximab plus CHOP (R-CHOP) chemotherapy, or (3) etoposide plus R-CHOP (R-EPOCH). In another example, if the sample is determined to be ABC subtype DLBCL, the subject from whom the sample was obtained is less likely to respond to CHOP or R-CHOP therapy, and such a subject may be selected for treatment with one or more alternative therapies (such as those disclosed herein).

In some embodiments, disclosed methods also include one or more of the following depending on the patient's diagnosis: a) prescribing a treatment regimen for the subject if the subject's determined diagnosis is GCB subtype DLBCL (such as treatment with one or more chemotherapeutic agents or systemic therapy; such as CHOP, R-CHOP, or R-EPOCH); b) prescribing a treatment regimen for the subject if the subject's determined diagnosis is ABC subtype DLBCL; or c) not prescribing a treatment regimen (such as not prescribing CHOP, R-CHOP, or R-EPOCH) for the subject if the subject's determined diagnosis is ABC subtype DLBCL.

VII. Methods of Treating a Subject with DLBCL

In some embodiments, following the classification of a DLBCL subtype, a subject can be selected for treatment with one or more therapies, for example if the sample from the subject is scored as GCB DLBCL or non-GCB (e.g., ABC) DLBCL. Additionally, the one or more therapies can subsequently be administered to the selected subject.

In some examples, the subject is administered a cyclophosphamide, doxorubicin, vincristine, and prednisone or prednisolone (CHOP) chemotherapy or rituximab plus CHOP (R-CHOP) chemotherapy. In one example, the subject is also administered etoposide to R-CHOP, resulting in a drug combination called R-EPOCH.

In other examples, the subject is administered one or more monoclonal antibodies, such as anti-CD20 (for example, rituximab, ofatumumab, ocrelizumab, GA101, tositumomab, or ibritumomab tiuxetan), anti-CD22 (for example, epratuzumab), anti-CD19 (for example, SAR3419 or blinatumumab), anti-CD30 (for example brentuximab vedotin), anti-CD40 (for example, dacetuzumab or lucatumumab), or anti-CD70 (for example, SGN-75). In some examples, a monoclonal antibody is conjugated to a toxin, radiolabel, or drug. In additional examples, the subject is administered one or more Bcl-2 inhibitors (for example, ABT-737, obatoclax, or oblimersen sodium), mTOR inhibitors (for example, rapamycin, everolimus, temsirolimus, or deforolimus (ridaforolimus)), Syk inhibitors (for example, fostamatinib (tamatinib)), proteasome inhibitors (for example, bortezomib), protein kinase C inhibitors (for example, enzastaurin or sotrastaurin), immunomodulating agents (for example, lenalidomide and pomalidomide), aurora A kinase inhibitor (for example alisertib), or histone deacetylase inhibitors (for example, vorinostat, romidepsin, panobinostat, belinostat, mocetinostat, abexinostat, or entinostat).

In some examples, a subject is administered CHOP, R-CHOP, or R-EPOCH as a first line therapy, and additional therapies, such as those described above (and in some examples a stem cell transplant), are administered upon relapse or the DLBCL is refractory to CHOP, R-CHOP, or R-EPOCH treatment. In other examples, R-CHOP or R-EPOCH and one or more of the additional therapies listed above can be administered to a subject with DLBCL. Rituximab and one or more of the additional therapies listed above can also be administered to the subject.

Additional therapies that may be used to treat a subject with GCB or non-GCB DLBCL include radiation therapy and/or one or more chemotherapeutics. In some examples, chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

A subject may be treated with a combination of therapies, including one or more of those described above. In a specific example, a subject may be administered a protein kinase C inhibitor in combination with rituximab, gemcitabine, and oxaliplatin (R-GEMOX). In another specific example, a subject may be administered a proteasome inhibitor (such as bortezomib) in combination with R-CHOP or in combination with etoposide, vincristine, and doxorubicin plus cyclophosphamide and prednisone (EPOCH). In a specific example, a subject is administered R-ACVBP (rituximab plus doxorubicin, cyclophosphamide, vindesine, bleomycin, and prednisone).

One of ordinary skill in the art can select appropriate therapies, dosages, and dosing schedules for a subject. The dose required will vary from subject to subject depending on the species, age, weight and general condition of the subject, the particular therapeutic agent(s) being used, and the mode(s) of administration.

Arrays to Detect Expression

Disclosed herein are arrays that can be used to detect or measure gene expression (such as expression of two or more of the biomarkers in Table 1), for example for use in determining DLBCL subtype in a subject with DLBCL. In some embodiments, the disclosed arrays can also be used to detect expression of one or more control genes (e.g., normalization biomarkers). In particular examples, the array surface includes a plate, bead, or flow cell.

In some embodiments, an array can include a solid surface including specifically discrete regions or addressable locations, each region having at least one immobilized oligonucleotide capable of directly or indirectly hybridizing to a biomarker in Table 1 (thus the array can have a plurality of regions, each specific for a biomarker in Table 1 for example). For example, the array can include specifically discrete regions, each region having at least one or at least two immobilized capture probes capable of directly or indirectly specifically hybridizing with at least 2, at least 3, at least 5, at least 10, or all 16 biomarkers in Table 1 (such as capture probes capable of directly or indirectly specifically hybridizing with each of CD47, CD86, ENTPD1, FOXP1, FUT8, IL16, ITPKB, LRMP, MME, NF2, PIM1, PTPRC, REL, STAT3, TNFRSF8, and TYMS). In some examples, the oligonucleotides are identifiable by their position on the array. In other examples, the oligonucleotides are identifiable by a detectable label (either directly or indirectly associated with the oligonucleotide). In another example, an array can include specifically discrete regions, each region having at least one or at least two immobilized oligonucleotides.

In some examples, the array includes two or more capture probes capable of directly or indirectly specifically hybridizing with an NPP of a DLBCL signature gene or a control gene. For example, the array can include oligonucleotides that include or consist of oligonucleotides that are complementary to at least 1, at least 2, at least 3, at least 4, at least 5, at least 6, at least 7, at least 8, at least 9, at least 10, at least 11, at least 12, at least 13, at least 14, at least 15, or all 16 of the DLBCL signature genes in Table 1 (such as oligonucleotides that include or consist of oligonucleotides that are complementary to each of CD47, CD86, ENTPD1, FOXP1, FUT8, IL16, ITPKB, LRMP, MME, NF2, PIM1, PTPRC, REL, STAT3, TNFRSF8, and TYMS, for example those shown in SEQ ID NOS: 1-16). In some examples the array (such as one that includes capture probes capable of directly or indirectly specifically hybridizing with each of CD47, CD86, ENTPD1, FOXP1, FUT8, IL16, ITPKB, LRMP, MME, NF2, PIM1, PTPRC, REL, STAT3, TNFRSF8, and TYMS) further includes oligonucleotides that include or consist of oligonucleotides that are complementary to at least 1, at least 2, at least 3, at least 4, at least 5, at least 6, at least 7, at least 8, or at least 9 control genes.

In particular examples, the array includes oligonucleotides (e.g., programming linkers) that include target nucleic acid sequences, such as nucleic acids including all or a portion of the regions of target nucleic acids disclosed in Table 1 (or an oligonucleotide complementary to such sequences). In some examples, programming linkers are bifunctional oligonucleotides which include a portion which is complementary to an oligonucleotide (such as an anchor) associated with a substrate and a portion which is complementary to at least a portion of an NPP.

In some embodiments, the array can include a surface having spatially discrete regions (such as wells on a multi-well surface, beads, or channels in a flow cell), each region including an anchor stably (e.g., covalently) attached to the surface and an oligonucleotide (e.g., a programming linker), wherein the programming linker is a hetero-bifunctional linker which has a first portion complementary to the anchor and a second portion complementary to an NPP, wherein the NPP is complementary to a target nucleic acid (such as two or more of: CD47, CD86, IL16, NF2, PIM1, PTPRC, REL, STAT3, TNFRSF8, and TYMS, such as two or more of CD47, CD86, ENTPD1, FOXP1, FUT8, IL16, ITPKB, LRMP, MME, NF2, PIM1, PTPRC, REL, STAT3, TNFRSF8, and TYMS, such as all of CD47, CD86, ENTPD1, FOXP1, FUT8, IL16, ITPKB, LRMP, MME, NF2, PIM1, PTPRC, REL, STAT3, TNFRSF8, and TYMS). In some embodiments the array includes or consists essentially of bifunctional linkers, wherein the first portion is complementary to an anchor and the second portion is complementary to an NPP. In some examples, the array further includes bifunctional linkers, wherein the first portion is complementary to an anchor and the second portion is complementary to an NPP complementary to a control marker. In an additional example, the array also further includes bifunctional linkers, wherein the first portion is complementary to an anchor and the second portion is complementary to an NPP complementary to a negative control (such as ANT). Such arrays have attached thereto the anchor hybridized to at least a segment of the bifunctional linker that is not complementary to the NPP. Such arrays can further include (1) the anchor probe hybridized to the first portion of the programming linker, (2) NPPs hybridized to the second portion of the programming linker, (3) bifunctional detection linkers having a first portion hybridized to the NPPs and a second portion hybridized to a detection probe, (4) a detection probe; (5) a label (such as avidin HRP), or combinations thereof.

Kits

Also disclosed herein are kits that can be used to detect or measure the levels of DLBCL signature genes (such as expression of two or more of the biomarkers in Table 1), for example for use in characterizing a sample as ABC, GCB, or unclassified DLBCL as discussed herein. In some embodiments, the disclosed kits can also be used to detect expression of one or more control markers (e.g., ANT). In particular examples, the kit includes one or more of the arrays provided herein, such as an array that includes capture probes capable of directly or indirectly specifically hybridizing with each of CD47, CD86, ENTPD1, FOXP1, FUT8, IL16, ITPKB, LRMP, MME, NF2, PIM1, PTPRC, REL, STAT3, TNFRSF8, and TYMS.

In some examples the kits include probes (e.g., NPPs or NPPFs) and/or primers for the detection of nucleic acid expression, such as detection of two or more of CD47, CD86, IL16, NF2, PIM1, PTPRC, REL, STAT3, TNFRSF8, and TYMS, such as two or more of CD47, CD86, ENTPD1, FOXP1, FUT8, IL16, ITPKB, LRMP, MME, NF2, PIM1, PTPRC, REL, STAT3, TNFRSF8, and TYMS, or for example all of CD47, CD86, ENTPD1, FOXP1, FUT8, IL16, ITPKB, LRMP, MME, NF2, PIM1, PTPRC, REL, STAT3, TNFRSF8, and TYMS. For example, the kits can include at least two different NPPFs and corresponding CFSs, wherein the at least two different NPPFs are specific for two or more of (such as at least 3, at least 4, at least 5, at least 6, at least 7, at least 8, at least 9, or all 10 of) CD47, CD86, IL16, NF2, PIM1, PTPRC, REL, STAT3, or TNFRSF8, or specific for two or more of (such as at least 3, at least 4, at least 5, at least 6, at least 7, at least 8, at least 9, at least 10, at least 11, at least 12, at least 13, at least 14, at least 15 or all 16 of) CD47, CD86, ENTPD1, FOXP1, FUT8, IL16, ITPKB, LRMP, MME, NF2, PIM1, PTPRC, REL, STAT3, TNFRSF8, and TYMS. For example, the kits can include NPPs (or NPPFs) specific for each of CD47, CD86, ENTPD1, FOXP1, FUT8, IL16, ITPKB, LRMP, MME, NF2, PIM1, PTPRC, REL, STAT3, TNFRSF8, and TYMS, such as NPPs that comprise or consist of the sequences shown in SEQ ID NOS; 1-16.

In some examples, the kits further include one or more control biomarkers. In some examples, the kits further include probes and/or primers to detect one or more control biomarkers (e.g., ANT).

Probes included in the kit can include one or more NPPs or NPPFs that are complementary to or specifically hybridize to target sequences disclosed herein, such as probes that include a sequence shown in SEQ ID NOs: 1-16. In some examples, the kits can include one or more nucleic acid probes needed to construct an array for detecting the biomarkers disclosed herein.

In some examples, the kits include antibodies that specifically bind to one or more biomarkers listed in Table 1, and optionally antibodies that specifically bind to one or more control biomarkers. For example, the kits can include antibodies (e.g., monoclonal antibodies, polyclonal antibodies, and/or antibody fragments) for the detection of protein expression, such as detection of two or more of CD47, CD86, IL16, NF2, PIM1, PTPRC, REL, STAT3, TNFRSF8, and TYMS, such as two or more of CD47, CD86, ENTPD1, FOXP1, FUT8, IL16, ITPKB, LRMP, MME, NF2, PIM1, PTPRC, REL, STAT3, TNFRSF8, and TYMS (such as all of CD47, CD86, ENTPD1, FOXP1, FUT8, IL16, ITPKB, LRMP, MME, NF2, PIM1, PTPRC, REL, STAT3, TNFRSF8, and TYMS), and in some examples, one or more control biomarkers.

In some examples, the kit additionally includes one or more of: a container containing a buffer (such as a lysis buffer, a hybridization buffer, a wash buffer, and/or a sequencing buffer); a container containing a nuclease specific for single-stranded nucleic acids (such as an S1 nuclease); a container containing nucleic acid programming linkers; a container containing ethanol; a container containing denaturation oil; a container containing proteinase K; a container containing beads that can specifically bind to amplicons of the at least two different NPPFs; and container(s) containing reagents for PCR (such as PCR buffer, polymerase, dNTPs). In some examples, kits further include control samples, such as particular quantities of CD47, CD86, ENTPD1, FOXP1, FUT8, IL16, ITPKB, LRMP, MME, NF2, PIM1, PTPRC, REL, STAT3, TNFRSF8, and TYMS nucleic acids or proteins.

In one example, a kit includes NPPs or NPPFs that are complementary to or specifically hybridize to CD47, CD86, ENTPD1, FOXP1, FUT8, IL16, ITPKB, LRMP, MME, NF2, PIM1, PTPRC, REL, STAT3, TNFRSF8, and TYMS, such as NPPs that comprise or consist of the sequences shown in SEQ ID NOS: 1-16. If the kit includes NPPFs, the kit can further include corresponding CFSs. In some examples, such a kit further includes a lysis buffer, a nuclease solution (such as one that includes S1), a termination buffer (e.g., one that can neutralize or deactivate the nuclease, such as one that can increase the pH above 6, such as to about 9 to 12). In some examples, such a kit further includes proteinase K; denaturation oil; and optionally microarray plates and pipette tips. In some examples, such a kit further includes ligation buffer (e.g., one that includes ligase). In some examples, the kit also includes primers specific for a portion of the NPP or NPPF or CFS, such as a primer that can add an experiment tag, and/or sequencing adapter at the 3'- or 5'-end or at both ends of the NPP or NPPF.

In one example, the kit includes a computing system that implements a classifier for subtypes of DLBCL, such as software or computer readable medium described herein that receives multiple values that measure or detect mRNA expression of DLBCL signature genes (such as two or more of CD47, CD86, ENTPD1, FOXP1, FUT8, IL16, ITPKB, LRMP, MME, NF2, PIM1, PTPRC, REL, STAT3, TNFRSF8, and TYMS), processes the multiple values using Equation 1, calculates a predicted probability, and classifies a sample in a framework that indicates the subtype of DLBCL of the sample (e.g., ABC, GCB, or unclassified).

In one example, the kit includes a graph or table showing expected values or ranges of values (such as predictive probability values) expected in DLBCL ABC and/or GCB subtypes and optionally unclassified samples.

The kits may further include additional components such as instructional materials and additional reagents, for example detection reagents, such as an enzyme-based detection system (for example, detection reagents including horseradish peroxidase or alkaline phosphatase and appropriate substrate). The kits may also include additional components to facilitate the particular application for which the kit is designed (for example microtiter plates, pipette tips, and the like). The kits may also include secondary antibodies (for example antibodies that specifically bind the primary antibodies that specifically bind the proteins in Table 1, or antibodies that specifically bind the primary antibodies that specifically bind to a control protein), or a means for labeling antibodies. In one example, the kit of further includes control nucleic acids and/or control proteins. Such kits and appropriate contents are well known to those of ordinary skill in the art. The instructional materials may be written, in an electronic form (such as a computer diskette or compact disk) or may be visual (such as video files).

The disclosure is further illustrated by the following non-limiting Examples.

Example 1

Identification of DLBCL Signature Gene List

This example describes statistical methods used to build a classifier to subtype DLBCL into two classes, ABC and GCB. Additionally, a third subtype that includes a region of uncertainty, denoted as unclassified, was added to the classification. All data analyses were performed using the R programming language version 3.2.2 and the Bioconductor package version 3.1 (64-bit versions).

General statistical design procedures were developed using a similar strategy as outlined in Hastie, Tibshirani, and Freidman (The Elements of Statistical Learning: Data Mining, Inference and Prediction Springer Science and Business Media, Inc., 2009) when using a single set of data for both development and testing of the estimated performance Two general steps were used in developing the subtype classifier, model development and model assessment. Model development includes model/variable selection, parameter tuning, and an internal evaluation of testing of the final model that defines the subtypes. The assessment includes estimation of prediction error. Both of these steps were performed utilizing a prospectively obtained single site convenience sample of DLBCL FFPE curls with associated DLBCL status evaluated by an expert clinician.

Quality Control

Three quality control (QC) metrics were applied to each sample after the sequencing was completed. Failure modes were identified for each of the mutually exclusive QC metrics evaluated in sequential order. The first of the QC metrics is alignment rate (based on Bowtie) of mapped reads to the probe sequences. The expectation is overall alignment is ≥85%, a sample has a failure mode of QC1 if this is not met. The second QC metric applied to all cases meeting the QC1 quality metric, is that the sample has differential expression. Expression is established by evaluating expression differences between probes at the first quartile of expression (Q1) and the third quartile of expression (Q3); if the ratio between average expression is less than 2.0 (Q1/Q3<2.0) then the sample would fail the second QC metric (QC2) (referred to as S1 failure or a wall of numbers). The third QC metric (QC3) applied to samples/cases passing QC1 and QC2 involved the negative controls: ANT probes (ANT1, ANT2, ANTS). Statistical process control (SPC) metrics for negative controls were established in a baseline study that sequenced a 90-wells of a single technical replicate from SUDHL6 cell line lysate. The SPC characterization study established upper tolerance for negative controls, this tolerance was then applied to all new samples to demonstrate performance within an expected performance Expected performance was established by evaluating average ANT signal variability. The expectation is that average ANT compared to mean levels should not fluctuate more than a pre-determined cut-off. The cut-off was is 7.75 on the $\log_2$(CPM); any sample with sample average ANT greater than this value would fail the third QC metric (QC3). All samples with any of these failure modes could have compromised classifier calls.

Samples

Figure 2:
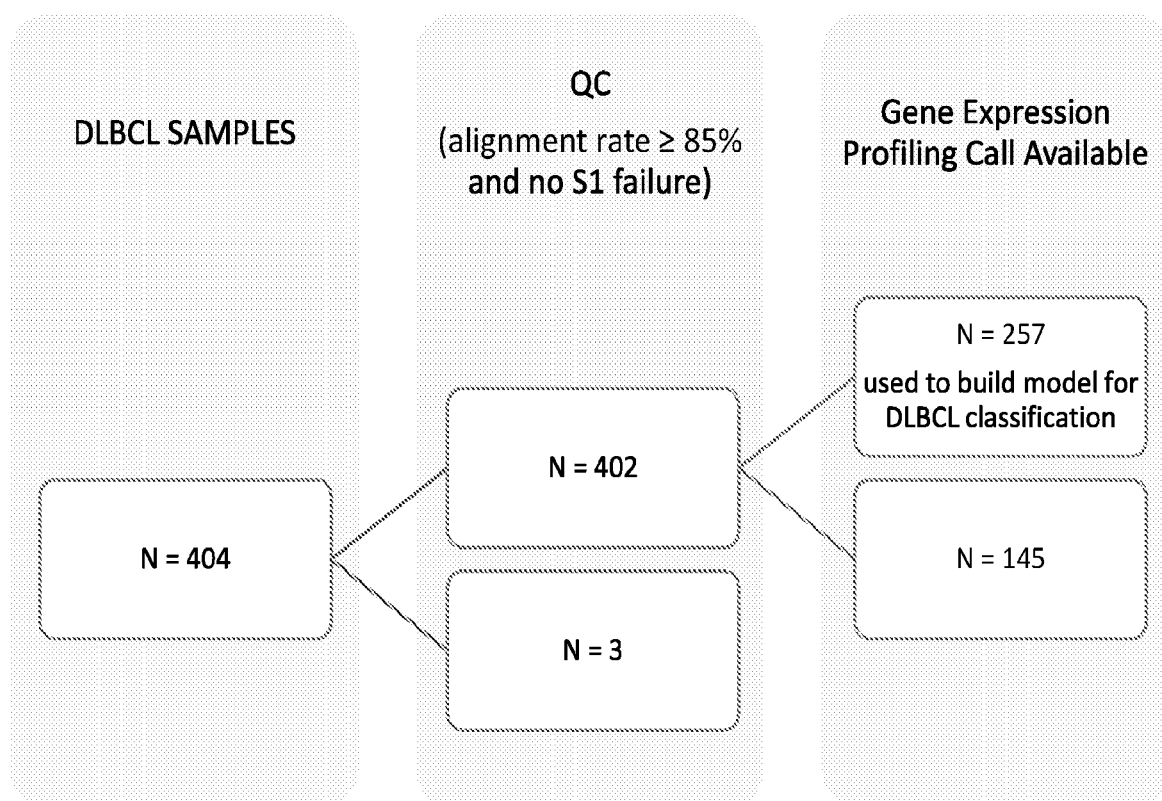
FIG. 2 is a flow diagram showing the cases used for the DLBCL classifier model training and validation.

A total 257 cases had enough representative tissue for sequencing, passed the sequencing quality control procedures described above, and had DLBCL status ascertained by gene expression profiling (GEP). Samples used in the analysis passed quality control metrics for average ANT values (negative control) and had probe to sequence alignments ≥85%. RNAseq is a methodology that counts the number of reads that are mapped to a specific sequence. Alignment rate is a way to quantitate how many of the base pairs are being correctly mapped to the RNA copies generated from the PCR it is expected that at least 85% of the available reads will be mapped within a sample. Less than this amount implies that there is unmapped product in the sample. FIG. 2 shows the data flow diagram for case selection from the total cases available.

DLBCL tissue lysates were prepared from FFPE tissue sections. The tissue section was measured and then scraped into a labeled eppendorf tube using a razor blade and avoiding any excess paraffin on the slide. The area of the sample was used to calculate the amount of lysis buffer added: total area (cm²)×/28 µl/0.25 cm² tissue or total area (cm²)×/25 µl/0.25 cm² tissue. The sample was suspended in the lysis buffer (pre-warmed (50° C.) SSC buffer including formamide and SDS). Five-hundred (500) µl of mineral oil containing a surfactant (e.g., Brij-97) ("Non-aqueous Layer") then was overlaid on the tissue suspension, and this lysis reaction was incubated at 95° C. for 10-20 minutes. After briefly cooling the reaction mixture, proteinase K was added to a ratio of ⅟₂₀$^{th}$ the volume of the lysis buffer and the incubation continued at 50 C for 60-120 minutes. The lysis reaction can be used immediately or frozen and stored at −70° C. to −80° C. Frozen lysis reactions were thawed at 50° C. for 10-15 minutes before a subsequent use. The sample input for was 0.02 cm²/28 µl for the samples with known sample input.

qNPS Assay

Twenty eight (28) µl of each lysed reaction mixture was placed in a well of a 96 well plate and overlaid with 70 µl Non aqueous Layer. To each well was added 5 µl of a mixture containing nuclease protection probe with a 5'- and a 3'-flanking sequence (NPPF) and appropriate complementary flanking sequences (CFSs) for each flanking sequence. The sequences of the NPPFs included a capture sequence that bound specifically to the target, as well as 3'- and 5'-flanking sequences. Table 2 shows the capture sequence portion of the NPPF for the 16 genes of the DLBCL classifier. Thus, the target sequence is the complement of the sequence shown. One (1) nM (an excess) of NPPF complementary to each of the plurality of mRNA targets to be detected was present in the mix. Each 96-well plate included 30 (each in triplicate) different DLBCL lysates and six control samples (two No Sample Control and 4 cell line lysates). DLBCL samples were randomized onto the plates in a blinded fashion (i.e., blinded sample annotation).

TABLE 2

| Capture portion of NPPF used to detect the target sequence | | |
|---|---|---|
| Target | NPPF Capture sequence | SEQ ID NO: |
| CD47 | AAACTGGTTACCTAGAGGCCAGAGGCCCTAGGACCTGAAAGGCATCATTC | 1 |
| CD86 | GTCTCCTCTTGGCATACGGAGCAGAGCTGGAGTTACAGGGAGGCTATTCC | 2 |
| ENTPD1 | CCATGAGGAAGACATAGGTGGAGTGGGAGAGAGGTGTGGACAATGGTTGC | 3 |
| FOXP1 | CTCTTCCCGTATTGCGCTGGCTAAGTTGCCCAGAGTGGGATTTCCCATGG | 4 |
| FUT8 | CAGTTTGGCTGAAATGGTTTGAACTGAGTTTGGTCGAACTGAGTTTGGTC | 5 |
| IL16 | GTCCATCAGGCAGTGCCTTGATGATGTTCCAGGCTTCAAACCGTGTGAGG | 6 |
| ITPKB | GCGCCTCAAACATGCCCACTTTCTGGTTCACCTGCACGTTCTGCAACTCG | 7 |
| LRMP | GCTATTTCTACAGCGGTTAAAGTCCTGATATGTCAAGTTGCCTCTTTCTG | 8 |
| MME | GGCCTTGCGGAAAGCATTTCTGGACTCCTTGTAGGTTCGGCTGAGGCTGC | 9 |
| NF2 | GAGAGAAATCTCTACAGGGTCGTAGTTCAAGGCAATTGCACATAAGAGGG | 10 |
| PIM1 | GCTCACCTTCTTCAGCAGGACCACTTCCATGGGCACTCGAGTGCCATTAG | 11 |
| PTPRC | GGAACAATTTCCTCCTCTGTTACCCTAAGAACAAACCACTTGCTAGCTGC | 12 |
| REL | CAGAGGTGCCATTGAGGCATGATGTGACAATCCACTTGAGATGGGCCCAG | 13 |
| STAT3 | CAGCTTCAGGATGCTCCTGGCTCTCTGGCCGACAATACTTTCCGAATGCC | 14 |
| TNFRSF8 | CTGGGACCAATGCTGTTCTCGGCAGTGCCCATCCTGCCATCTGTTTGCTG | 15 |

TABLE 2-continued

Capture portion of NPPF used to detect the target sequence

| Target | NPPF Capture sequence | SEQ ID NO: |
|---|---|---|
| TYMS | CTTCAGGCCCGTGATGTGCGCAATCATGTACGTGAGCAG GGCGTAGCTGG | 16 |

The 96-well test plate was heated at 85° C. for 10 minutes to denature nucleic acids and, then, allowed to incubate at 52° C. for 16 hours to permit hybridization of the NPPF to their respective mRNA targets, and to permit hybridization of the CFSs to their respective flanking sequence target.

Following the hybridization step, 20 µl of excess S1 nuclease (2.5 U/µl) in sodium acetate buffer was added to the aqueous phase of each well. The S1 reaction proceeded at 52° C. for 90 minutes to digest unbound mRNA and unbound NPPFs and unbound CFSs.

During the S1 digestion step, a 96-well "Stop" plate was prepared by adding 5 µl of solution containing 1M Tris-HCL (pH 9.0) to each well corresponding to the reactions in the 96-well test plate. 40 µl of each reaction in the 96-well test plate was transferred to a corresponding well in the second 96-well Stop plate and overlaid with 70 µl Non aqueous Layer. The Stop plate was incubated at 100° C. for 20 minutes and, then, cooled for 30 minutes at room temperature.

After completion of the capture reaction, the plate can be stored at −20° C. or used directly for PCR tagging. If the plates were stored frozen, they can be thawed at room temperature for 30-40 minutes with gentle shaking prior to using in the PCR.

PCR tagging was performed for sequencing library preparation as follows. PCR reagents, including 6 µl water, 15 µl of NEB OneTaq® HotStart X2 Master Mix GC buffer, 3 µl forward primer, 3 µl of reverse primer, and 3 µl sample were added to a clean tube. As a negative control, some samples simply received water. PCR was performed for 20 cycles To remove excess primers following PCR, 15 µl of each PCR sample (excluding the PCR negative controls) was pooled in a microfuge tube. 350 ul of the pooled PCR reactions was mixed with 135 µl 5M NaCl, 137 µl 40% PEG solution, and 35 ul AMPure beads. The tube was vortexed and incubated at 5 minutes at room temperature. The tube was placed on a magnet stand for 5 minutes to allow the beads to collect. The supernatant was discarded. To the beads, 30 µL of 10 mM Tris-HCl pH 8.0, and 75 µL AMPure XP were added. The tube was vortexed and incubated for 5 minutes at room temperature. The tube was place on a magnet stand for 5 minutes to allow the beads to collect. The supernatant was discarded. The beads were washed twice with 80% ethanol and the beads allowed to dry at 37° C. for 5 minutes. The beads were suspended in 40 10 mM Tris-HCl pH 8.0. 30 µl supernatant was added to a new tube, which contained the cleaned-up. The removal of primers was confirmed by running 10 µL of the library on 2% agarose gel.

The cleaned amplicons were diluted 1:10,000 using the KapaQuant kit (Kapa Biosystems, Catalog #10176100), following the manufacturers' directions.

The cleaned amplicons were sequenced using a MiSeq sequencer (Illumina). 30 pM of library was loaded onto a MiSeq 150 bp V3 kit, following the manufacturer's instructions for library denaturation and sequencer setup and loading.

Model Development

As a first step in building the classifier algorithm, 257 quality controlled DLBCL samples for which gene expression (GEP) calls were available were randomly subset into two non-overlapping data sets comprising of 172 random samples for classifier development; the remaining 86 were used as a validation set. The similarity of these two random samples was evaluated to ensure there was no bias introduced by the random selection. Table 3 describes the distribution of these two subsets by GEP calls.

Figure 3:
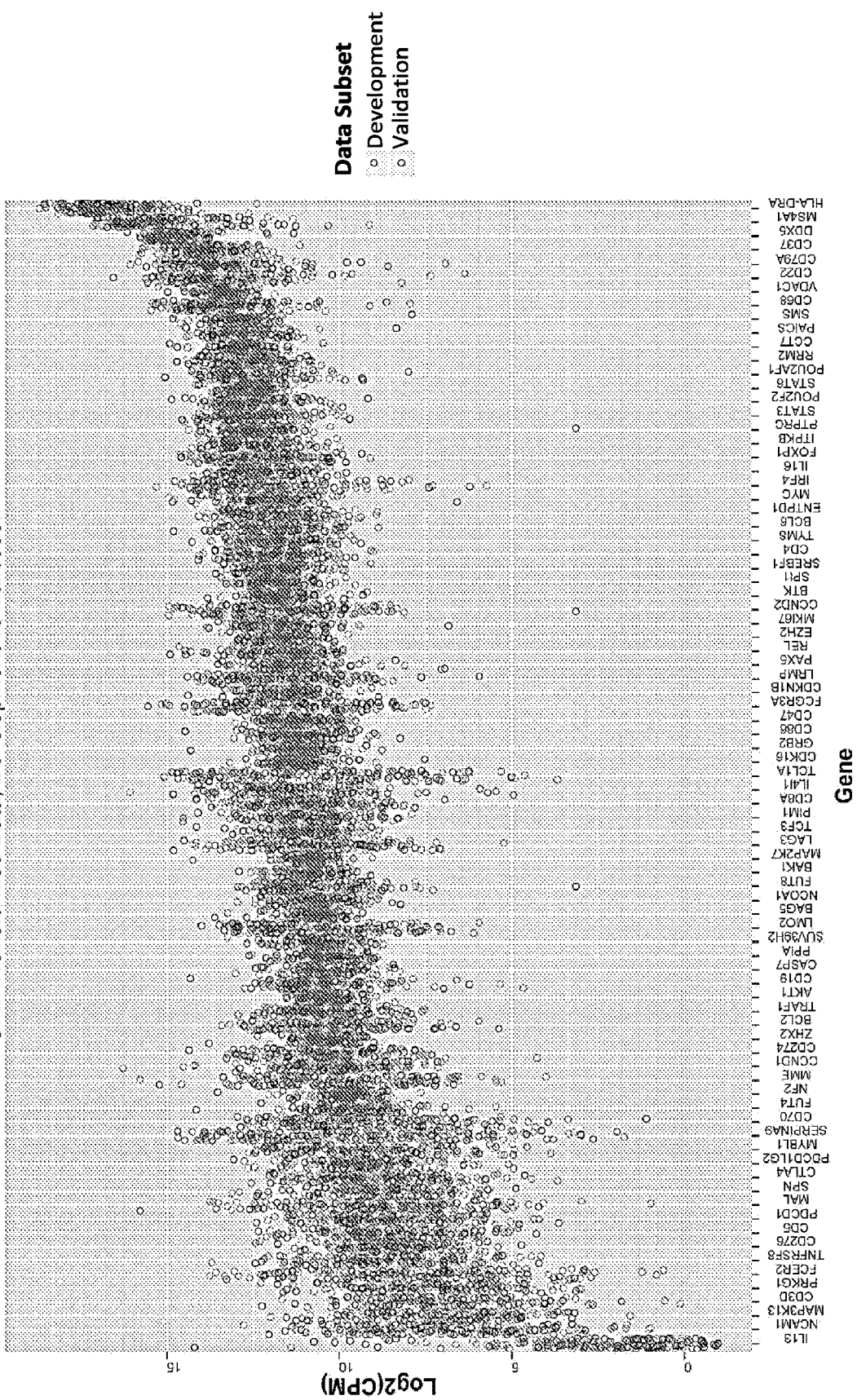
FIG. 3 is a graph showing the distribution of expression across samples for 96 genes included in the DLBCL assay used to train and validate a classifier embodiment.

Initially, expression of 96 genes was determined in all of the DLBCL samples using qNPS. FIG. 3 shows the random nature of the possible classifier genes, after removal of negative, positive, and housekeeping gene across the two sets; bias would show up in differences between $\log_2(CPM)$ counts instead of overlapping as they do in FIG. 3. Housekeeping and control probes (Table 4) were removed before statistical analyses were performed. Removal of these probes resulted in 83 genes considered for the classifier.

TABLE 3

Distribution of GEP calls between the development and validation sets.

|  | ABC | GCB |
|---|---|---|
| Development | 86 | 86 |
| Validation | 36 | 49 |

TABLE 4

Housekeeper and Control Probes by Parser Names

| Housekeeping Probes | Control Probes |
|---|---|
| ACTB | POS_CTRL_POS1 |
| EEF1G | NEG_CTRL_ANT1 |
| EIF4A1 | NEG_CTRL_ANT2 |
| GAPDH | NEG_CTRL_ANT3 |
| RPL19 |  |
| RPL4 |  |
| RPL6 |  |
| RPS29 |  |
| TBP |  |

Classifier development was performed using a generalized linear model with a log it link function, also known as logistic regression. Logistic regression is a model used when response (outcome) data have two categories, also called binary; in this case the two categories are the ABC and GCB classification/subtype. The statistical model that is used to estimate the probability of a given classification is written as:

$$Pr(Y = y | x) = \frac{e^{(\beta_0 + x^T \beta)}}{1 + e^{(\beta_0 + x^T \beta)}} \quad \text{(Equation 1)}$$

Where $\beta_0$ denotes an intercept and $\beta$ are the parameter estimates associated with the vector of probes, $x^T$. The development sample was used to fit a logistic model described at (1) to obtain parameter estimates, $\hat{\beta}_0$ and $\hat{\beta}$, these are called are called the "weights". These weights are used, in conjunction with the values of expression level counts for each gene, to determine a predicted probability, Pr(Y=y|x), of being classified as ABC or GCB in any new (independent from the development data set) set of data. The final model can have as many $\hat{\beta}$ values as probes used to calculate the probabilities. The estimated probabilities are bounded between 0 and 1, and an optimal cut-off for the probabilities is used to classify future patients.

The development portion of the model included two steps, the training and testing. The testing phase refers to the internal metrics that were used to identify the optimal probes/targets, and obtain parameters (weights) after target/probe selection and coefficient shrinkage/scaling. This is slightly different from some statistical literature (Tibshirani, J. Royal Statistical Society (Series B) 58:267-288, 2006) that suggests three random sets of data should be used: training, testing, validation. For purposes of this classifier, the training and testing was performed in the same development set. Determination of the optimal cut-offs in the probabilities for ABC, GCB and Unclassified patient classification was performed in the testing phase. All of these steps were performed using the development set of cases.

Selection of the 83 targets used for the probabilistic calculation, along with optimization of the weights, was performed using an algorithm called "the lasso". Statistically, these methods are group by the type of "penalty" that is applied as a part of the optimization, this penalty shrinks the weights to adjust for potential bias based on small sample sizes. Methods describing this approach have been published (e.g., see Tibshirani, J. Royal Statistical Society (Series B) 58:267-288, 2006). The lasso algorithm employed for development of this classifier is implemented in the "glmnet" package in R and described in Friedman et al. (J. Statistical Software, 33(1):1-22, 2010). The optimal variables were determined using ten-fold cross-validation as a resampling. This is a method where the initial development dataset is partitioned into equally sized sub-samples of size 10, and there were 100 such subsamples created. These subsamples were used to both find the model (e.g., the fitted regression parameters) that best classify into the two subtypes (i.e., ABC, GCB), as well as determining the values that will be used as weights (e.g., the coefficients after any scaling and shrinking that may occur).

Using this methods, the field of 83 targets was narrowed to the 16 targets in Table 5. Table 5 also lists the "weights" for the optimal set of coefficients ($\hat{\beta}$'s) (that is, for each target). Those targets having with weights less than 1 (i.e., negative) are associated with ABC classification, and those with weights greater than 1 are associated with GCB classification.

TABLE 5

| Coefficients for DLBCL Classifier | |
| --- | --- |
| Gene | Coefficients (weights) |
| CD47 | −0.16 |
| CD86 | 0.83 |
| ENTPD1 | −0.71 |
| FOXP1 | −0.56 |
| FUT8 | −0.30 |
| IL16 | −0.51 |

TABLE 5-continued

| Coefficients for DLBCL Classifier | |
| --- | --- |
| Gene | Coefficients (weights) |
| ITPKB | 1.16 |
| LRMP | 0.16 |
| MME | 0.59 |
| NF2 | −0.70 |
| PIM1 | −0.13 |
| PTPRC | 0.07 |
| REL | 0.20 |
| STAT3 | −0.17 |
| TNFRSF8 | −0.01 |
| TYMS | −0.25 |

Predicted Probability Cut-Offs

Figure 4:
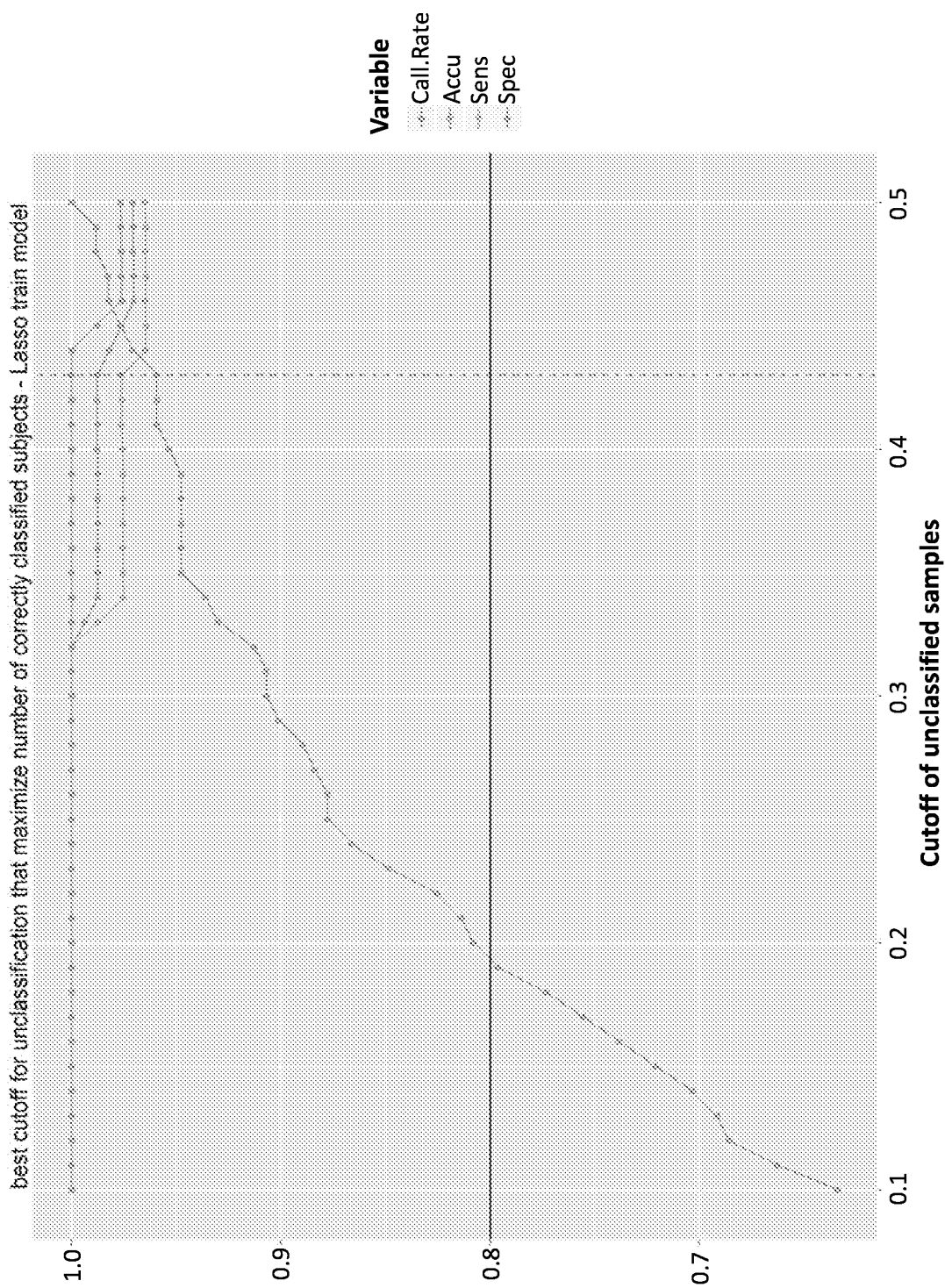
FIG. 4 is a graph showing a means for determining a lower bound for unclassified samples.

Once the optimal targets and weights were obtained, the cut-off for the predicted probability was obtained. When there are exactly two classifications, the probability that defines the classes is obtained by maximizing the sensitivity (probability of correctly specifying a sample as ABC) and specificity (probability of correctly specifying a sample as GCB) over the entire range of the predicted probabilities. The DLBCL classifier also included a subset of "unclassified" samples. These samples are identified as the set of samples that are possibly neither an ABC or GCB and thereby potentially fall under a separate subtype (e.g., for which the ABC or GCB call cannot be made). The point at which sensitivity+specificity (the combination of which is called accuracy) starts to fall from the maximal point at the same point that the misclassification rate increases was determined. This was called the lower bound; the upper bound is the symmetric high point associated with this value. FIG. 4 depicts this decision point graphically; numerically, the cut-offs are 0.43 for the lower point, and 0.57 for the upper point. The resulting ABC/GCB calls are those cases with estimated probability <0.43 are ABC, and those with estimated probability >0.57 are GCB, everything within and including 0.43-0.57 are UNCLASSIFIED.

Example 2

Application of DLBCL Classifier to Independent Samples

This Example demonstrates that the DLBCL classifier developed in Example 1 allows for identification of GCB and ABC subtypes of DLBCL in formalin-fixed, paraffin-embedded (FFPE) samples.

Final testing of the classifier showed low propensity of "over-fitting" (e.g., over-optimism) and the resulting weights were applied to the validation set to demonstrate performance Thus, the development of the classifier was completed on this set of data.

The remaining 86 DLBCL samples not used to develop the classifier were used as a validation set. qNPS analysis of the 16 genes in Table 5 was performed as described above. The resulting data was subjected to the classifier (e.g., the value for each gene obtained using qNPS was analyzed with Equation 1, and the predicted probability determined). As mentioned elsewhere herein, CD86, ITPKAB, LRMP, MME, PTPRC and REL are genes that tend to be associated with the GCB subtype of DLBCL, and CD47, ENTPD1, FOXP1, FUT8, IL16, NF2, PIM1, STAT3, TNFRSF8 and TYMS are genes that tend to be associated with the ABC subtype of DLBCL. The output value for each of the 16 genes obtained from qNPS was multiplied by the weight value shown in Table 5, the aggregate sum of these 16 genes was determined, and the predicted probability determined, wherein the resulting predicted probability value determines if the sample is ABC, GCB, or unclassified.

Figure 5:
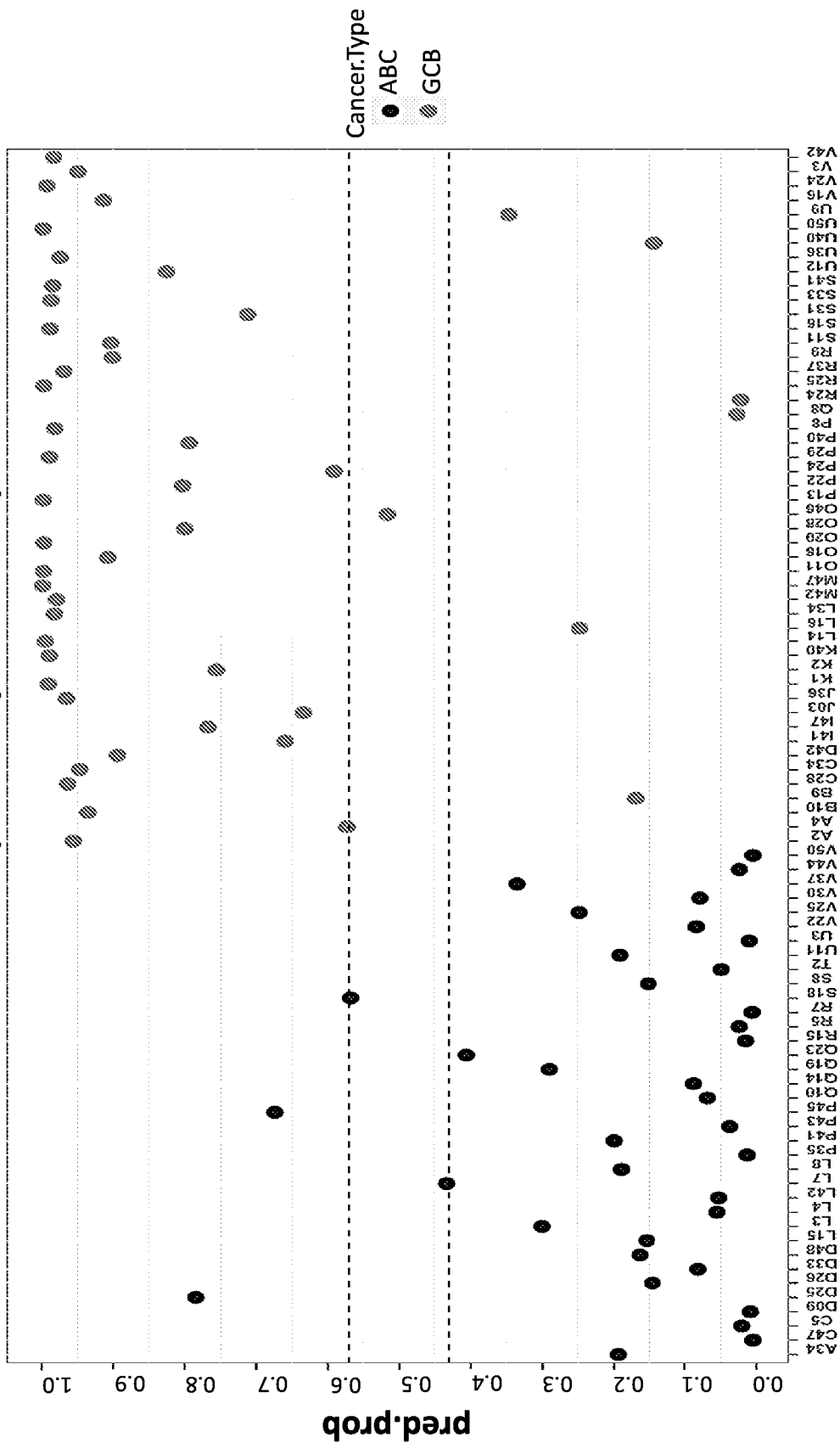
FIG. 5 is a graph showing the classification (i.e., ABC, GBC, or unclassified) of a validation set of DLBCL samples, which had previously been characterized by clinically accepted methods as ABC (black dots) or GBC (red dots). Samples are identified along the x-axis. The y-axis shows the predicted probability for each case based on gene expression profiling. In this embodiment, the cutoff for the estimated probability for a GCB sample was 0.57 (predicted probability >0.57 are GCB), the cutoff for ABC classification was below 0.43 (predicted probability <0.43) and unclassified samples fell between, and includes, the ABC and GCB cutoffs (0.43≤predicted probability ≥0.57).

Metrics for classifier performance include misclassification rate, defined as the proportion of cases for which the classifier was able to obtain an ABC/GCB call that was the same as the GEP calls. Additional metrics included the predictive value positive and negative predictive value (PPV and NPV, respectively; i.e., cases that are correctly classified as either ABC or GCB). Note that unclassified samples are not included in the evaluation of these metrics. Table 6 shows a summary of the validation of the classifier applied to the validation set, and FIG. 5 depicts the classification for each sample.

TABLE 6

Performance Metrics for Classifier On Validation Set

|  | Proportion of Cases |
| --- | --- |
| Correctly Classified as GCB (PPV) | 0.95 (42/44) |
| Correctly Classified as ABC (NPV) | 0.84 (32/38) |
| Misclassified | 0.10 (8/82) |
| Overall Correct Calls | 0.96 (74/82) |

Example 3

In Vitro DLBCL Diagnostic Assay

This example describes methods that can be used to determine the cell of origin (COO) subtype of diffuse large B-cell lymphoma (DLBCL) tumors from FFPE tissue using the HTG EdgeSeq system with detection performed on an Illumina MiSeq next-generation sequencer. The profiled data are assessed by a classification algorithm and the tumor determined to be of the Activated B-cell like (ABC), Germinal B-cell like (GCB), or unclassified sub-type.

The HTG EdgeSeq system combines a quantitative nuclease protection assay (qNPA) chemistry with a Next Generation Sequencing (NGS) platform to enable the semi-quantitative analysis of 96 targeted genes in a single assay (FIG. 1). The qNPA chemistry does not require nucleic acid extraction from most sample, thereby significantly reducing sample input requirements. It also eliminates biases associated with nucleic acid extraction, size selection, cDNA synthesis, and adapter ligation. The automated procedure reduces operation errors, and thereby helps to ensure that sequencing libraries prepared from precious samples like FFPE tissue can be generated reproducibly. Use of the HTG EdgeSeq system, allows laboratorians to go from raw sample to sequencing-ready libraries in approximately 36 hours with less than three hours of hands-on time.

The qNPA technology (see for Example U.S. Pat. No. 8,741,564, herein incorporated by reference) enables mRNA quantitation in an extraction-free, no RNA amplification format. Two primary elements of HTG EdgeSeq chemistry process are DNA to RNA hybridization and S1 nuclease digestion. Functional DNA nuclease protection probes flanked by universal wing sequences are hybridized to target RNAs, which can be both soluble and cross-linked in the biological matrix. Universal DNA wingmen probes are hybridized to the wings to prevent S1 nuclease digestion. S1 nuclease is added to digest excess, non-hybridized DNA probes and non-hybridized RNA; the only remaining fully-intact, functional DNA protection probes are those hybridized to target RNA. This produces essentially a 1:1 ratio of DNA detection probes to the RNA initially targeted in the sample. Heat denaturation releases the protection probes from the DNA:RNA duplexes. The released DNA protection probes are ready for enumeration.

DNA protection probes are labeled with sequencing adaptors and tags in a thermocycler. The labeled DNA protection probes are concentrated, pooled, and ready for sequencing using standard NGS protocols on the Illumina MiSeq platform. Gene expression data from the NGS instrument are processed and reported, for example through the HTG EdgeSeq host system software.

Specially designed oligonucleotides (probes) that hybridize to complimentary sequences in the target mRNA are used as a means to measure the levels of mRNA. These oligonucleotides are designed to sequences that are checked to ensure the absence of potential secondary structure and are subjected to BLAST searches against other reported human sequences to ensure a lack of significant homology or complementarity with other genes in the assay. Each oligonucleotide is a 100-mer comprising a 25-mer "wing" at the 5' end, a 25-mer "wing" at the 3' end, and a 50-mer sequence in between that is complementary to the target mRNA.

The HTG EdgeSeq DLBCL Cell of Origin Assay includes four major steps. (1) Sample Preparation (Manual Step): HTG Lysis Buffer is added to lyse and/or permeabilize the FFPE tissue sample making the RNA available to subsequently bind to corresponding target-specific Nuclease Protection Probes (NPP). The lysed sample is transferred to a standard 96-well micro-titer plate, referred to as the Sample Plate. (2) Target capture through HTG EdgeSeq chemistry (Automated Step): Target capture is done by the HTG EdgeSeq chemistry. Briefly, the Nuclease Protection Probes (NPPs) are added to the lysed samples in the Sample Plate in excess amount and hybridized to the target mRNA. Then S1 nuclease is added to digest non-hybridized mRNA and excess NPPs, thus producing a stoichiometric amount of target-mRNA/NPP duplexes. After the S1 digestion is completed, the processed sample is transferred to a new 96-well micro-titer plate with a v-bottom, referred to as the Stop Plate, and S1 digestion is terminated by the addition of termination solution followed by heat denaturation of S1 enzyme. (3) PCR Amplification for the Addition of Adaptors and Barcodes (Manual Step): Each processed sample from the stop plate is used as template to set up PCR reactions with specially designed primers, referred to as tags. These tags share common sequences that are complementary to 5'-end and 3'-end "wing" sequences of the probes and common adaptors required for cluster generation on an Illumina MiSeq sequencing platform. In addition, each tag contains a unique barcode that is used for sample identification and multiplexing. 12 forward and 8 reverse primer tags can be used, and therefore up to 96 samples can be analyzed simultaneously on an Illumina sequencing platform. The HTG EdgeSeq DLBCL Cell of Origin Assay is configured to analyze either 8, 24, or 96 samples simultaneously on the Illumina MiSeq instrument. After the PCR amplification is finished, a clean-up procedure is performed to remove unincorporated tags from PCR products (referred to as a library). PCR cleanup is then performed with individual PCR reactions. (4) Quantitation of Libraries and Sequencing (Semi-Automated Step): The sequencing is performed on Illumina MiSeq platform using MiSeq v3 kit. The concentrations of the sample libraries will be balanced and adjusted to ensure appropriate cluster generation. The sequencing data on mRNA expression of target genes is imported into HTG EdgeSeq parser software, where the DLBCL COO sub-type can be reported in a tabular format to the laboratorian.

Sample Processing:

For FFPE samples, sections tested should be 4-6-micron thick and mounted on glass microscope slide. The area(s) in the section to be tested should be determined to be DLBCL. For each sample, one H&E stained slide or scanned image with the area of interest clearly marked is strongly suggested to guide macro-dissection of the area of interest from the slide. Typically, one unstained section is required. If the tumor portion contained in the section is extremely small, multiple sections may be scraped and combined in a single tube for testing.

When measuring the size of the tumor, exclude any normal, other non-tumor or necrotic tissue from the tissue section. In circumstances where exclusion is not practical, do not include non-tumor tissue in the size calculation. When the tissue section provides more surface area than the maximum recommended sample input, scrape the entire relevant tumor portion and dilute to the proper working concentration using Lysis buffer. If testing extremely small tissues, multiple sections may be combined into a single tube to achieve desired tissue input amount, and processed as a single sample. Denaturation oil may form a white precipitate when stored at room temperature. Warm the denaturation oil at 50° C. for 10 mins, and briefly mix the bottle to dissolve the precipitate. Lysed samples which will not be immediately used may be frozen at −80° C. for up to one (1) week in microfuge tubes. Samples should not be frozen in the 96-well sample plate.

FFPE tissue processing can be performed as follows. The proper area(s) to test are identified with H&E staining, IHC, or other appropriate means; mark this area on the back of the slide using an indelible marker. Measure and calculate the total surface area (in $mm^2$) encompassed by the marked area. Exclude tissue areas that are of low-cellularity, non-target tissue, necrotic, or that could otherwise compromise the test results. Acceptable input amounts for the HTG EdgeSeq DLBCL Cell of Origin Assay are 1.56-12.5 $mm^2$ of tissue per test. In the case of extremely small samples (e.g. needle core biopsies), multiple tissue sections may be combined in the same tube to achieve the required sample amount. Thaw the lysis buffer and the denaturation oil at 50° C. for 30 mins. The Proteinase K should be kept at −20° C. until ready for use. Starting with an unstained section, use the marked slide as a guide and scrape the appropriate area of tissue off the unstained slide with a razor blade. Place the tissue into an appropriately labeled RNAse-free microcentrifuge tube (a pipette may be used to assist removal from the razor blade and placement in the microfuge tube). Centrifuge briefly (for ~20 seconds) to pull FFPE tissue to the bottom of the tube. Add 35 µL of HTG lysis buffer to the tube per targeted area of tissue. For example:

TABLE 7

Exemplary amounts of tissue and lysis buffer

| Tissue amount | Lysis buffer volume (µl) |
|---|---|
| 1.56-12.5 $mm^2$ | 35 |
| 12.6-25 $mm^2$ | 70 |
| 25-50 $mm^2$ | 140 |
| 50-100 $mm^2$ | 280 |

Extremely large sections may be processed using multiples of lysis buffer volumes listed above. Add 500 µL of denaturation oil to each tube, and cap the tube. Do not vortex. Heat the samples to 95° C. for 15 minutes, and allow samples to cool for 10 minutes at room temperature. Add Proteinase K to the lower layer (red color) of each tube in a ratio of ½0th the volume of lysis buffer. For example:

TABLE 8

Exemplary amounts of lysis buffer and proteinase K

| Lysis Buffer volume (µl) | Proteinase K (µl) |
|---|---|
| 35 | 1.75 |
| 70 | 3.5 |
| 140 | 7 |
| 280 | 14 |

Mix the Proteinase K by pipetting the solution six times. Incubate the lysed samples at 50° C. for 3 hours with mixing on an orbital shaker or every 30 minutes pipette. Samples may be processed or stored frozen at −70 to −80° C. for up to 4 weeks.

Initiating a Run on the HTG EdgeSeq Processor:

Remove the HTG EdgeSeq Assay Reagent Pack from the packaging and thaw at room temperature for 80 minutes. Do not shake or invert the reagent tray, the reagents will be mixed on the instrument prior to use. Clean HTG EdgeSeq Assay Reagent Pack using 10% bleach followed by 70% isopropyl alcohol. If lysed samples are frozen, thaw at 50° C. for 45 minutes and pipette mix the aqueous phase of each sample prior to use. Briefly centrifuge the samples to return all liquid to the bottom on the tube. Pipette 35 µL of each sample into the appropriate well of the sample plate. Using the HTG EdgeSeq system barcode scanner, scan the sample plate from the HTG EdgeSeq Plate Pack. The HTG EdgeSeq processor is then started, and will run for approximately 20 hours. Following processing, remove Stop Plate and analyze.

Library Processing:

PCR master mixes can be prepared, for example using NEB OneTaq® HotStart 2× Master Mix GC buffer, molecular grade water, and sequencing tags. This mixture, along with a reverse primer, is added to a portion of the appropriate samples in the stop plate, and PCR performed as follows: 95° C. for 4 minutes, then 20 cycles of: 95° C. for 15 seconds, 56° C. for 45 seconds, and 68° C. for 45 seconds, then 68° C. for 10 minutes, and hold at 4° C. The resulting reaction can be immediately processed or stored at −20° C. The library can be pooled and cleaned up as follows. Transfer 15 µL of each PCR product to a new pre-labeled 96-well PCR plate. Add 37.5 µL of AMPure XP beads per well (pre-warmed to RT and mixed well by vortexing for 1 minute). Mix well and incubate at room temperature (RT) for 5 minutes. Place sample on magnet stand and allow 3 minutes for beads to collect. A visible pellet of beads should form. Remove the supernatant and do not disturb the bead pellet. To prevent contamination with beads, 5-10 µL of residual liquid may be left behind if bead pellet is loose. Add 200 µL freshly prepared 80% ethanol and let stand for 30 seconds to 1 minute. Remove the ethanol from each well. Repeat the ethanol wash for a total of two washes. Remove the plate from the magnet stand and allow to dry at RT for 5 mins. Add 40 µL of 10 mM Tris-HCl, pH 8.0 to each well and pipette mix to re-suspend the beads. Let stand 5 minutes at RT. Place plate on magnet stand for 2 minutes to collect the beads. Transfer 30 µL of each library supernatant into a fresh well.

The individual sample libraries created can be quantified and individual library concentration balanced prior to sequencing, for example using the KAPA Quantitation system as follows. Perform a 1:100 serial dilution (e.g., in triplicate). Add 297 µL 10 mM Tris/0.05% Tween to each well of the 1:100 dilution. Add 3 µL of cleaned up library to the corresponding wells in the deep well plate. Mix the samples. Perform a second 1:100 dilution to achieve a final dilution factor of 1:10,000. Add 297 µL 10 mM Tris/0.05% Tween to each well of the 1:10,000 dilution. Add 3 µL of the sample from the "1:100 Dilution" plate to the corresponding wells in the "1:10,000 Dilution" plate. Mix well. If 1:100,000 dilution is required, perform an additional 1:10 dilution. Thaw the KAPA library quantification kit at RT for 30 minutes. f first time use, add 1 mL of 10× Primer Premix to the bottle of 2×KAPA SYBR FAST qPCR Master Mix (5 ml) and mix. Calculate the volumes of 2× Mastermix, SOX ROX High Dye (if required), and Molecular biology grade $H_2O$ for the HTG EdgeSeq samples and standards per manufacturer instructions. Create the appropriate order entry and protocol for the qPCR system being utilized. Load the qPCR instrument and cycle the samples per manufacturer's instructions. After cycling is complete, export the results as a Microsoft Excel® file. Ensure QC metrics for the standard curve are compatible with manufacturer's specifications.

The pooled library can be created, for example using the HTG EdgeSeq IVD Library Calculator.

Sequencing on the Illumina MiSeq System:

Sequencing of the pooled library can be performed as follows, for example using the Illumina MiSeq Instrument according to the manufacturer's instructions. The optimal final pooled library concentration for each Illumina MiSeq instrument may vary. The resulting sequencing data can be analyzed.

The HTG EdgeSeq DLBCL Cell of Origin Assay classification system performs a data quality assessment prior to producing the sample classification. Samples that do not pass these requirements are reported as a "QC failure" with an attached number. If insufficient sequencing reads were obtained for classification, then ensure the sample was properly quantitated and sufficient library was added during the Library Pooling and Quantitation stage; re-run the sample from any remaining sample lysate, re-lyse the sample from a fresh section of FFPE tissue. Reassess the tissue to ensure the utilized area is tumor, or combinations thereof. If the profile of the data does not reflect expression typical patterns obtained from DLBCL, this indicates a potential sample preparation or processor issue. In this situation, re-run the sample from any remaining sample lysate, and/or re-lyse the sample from a fresh section of FFPE tissue and reassess the tissue to ensure the utilized area is tumor.

Performing the HTG EdgeSeq DLBCL Cell of Origin Assay:

Allow the frozen components provided with the HTG EdgeSeq DLBCL Cell of Origin Assay to thaw at room temperature for 80 mins without mixing or agitating the reagents. Thaw any frozen sample lysates by heating at 50° C. for 30 minutes prior to pipetting the samples into the Sample plate. The placement of consumables within the HTG EdgeSeq processor may vary with the number of samples to be processed.

Assay Results:

The assay report produces three potential results consistent with DLBCL cases of the (1) "ABC" or activated B-cell subtype, (2) "GCB" or germinal B-cell subtype, (3) "Unclassified" where the pattern of gene expression was not indicative of an ABC or GCB, or (4) "QC failure", which indicates the sample did not produce results that pass sample-level quality control metrics prior to classification, and the samples should be re-run.

Tumors displaying an ABC subtype generally have a poorer prognosis and response to standard-of-care DLBCL therapies than those of the GCB subtype. Subtyping of DLBCL tumors may direct the clinician towards alternate forms of therapy in relapsed patients. (Vose, *J Clin Oncol* 2011 29:4065-4066; Thieblemont et al., *J Clin Oncol* 2011 29:4079-87). Recent changes to the World Health Organization DLBCL classifications have been made to recognize these differences and to facilitate investigations into more effective treatments for the ABC subtype (Swerdlow et al., *Blood* 2016; 127:2375-90). Included in these options are investigational trials for numerous new therapeutics.

Performance Characteristics

Figure 6:
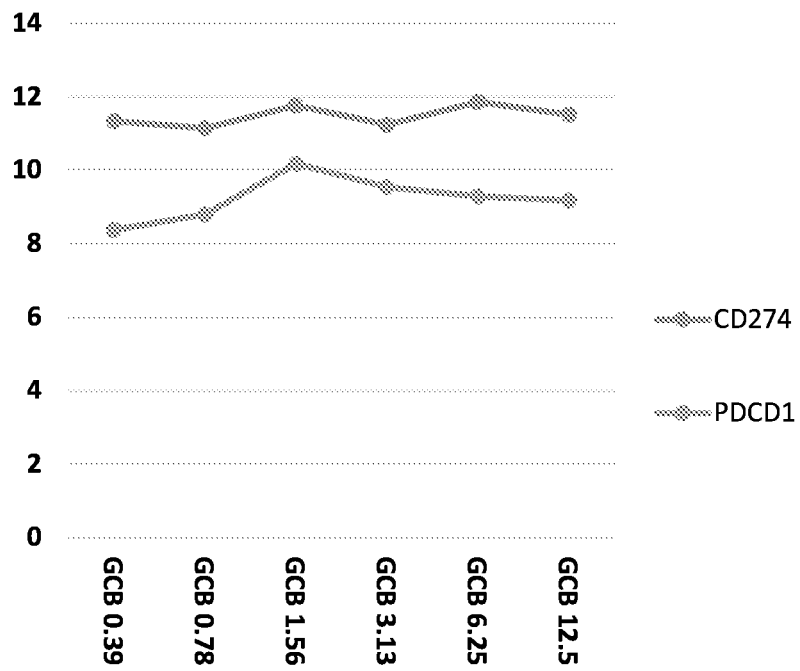
FIG. 6 is a graph showing the Log 2 CPM for CD274 (PDL-1) and PDCD1 (PD1) in lysate prepared from a GCB FFPE sample.
Figure 7:
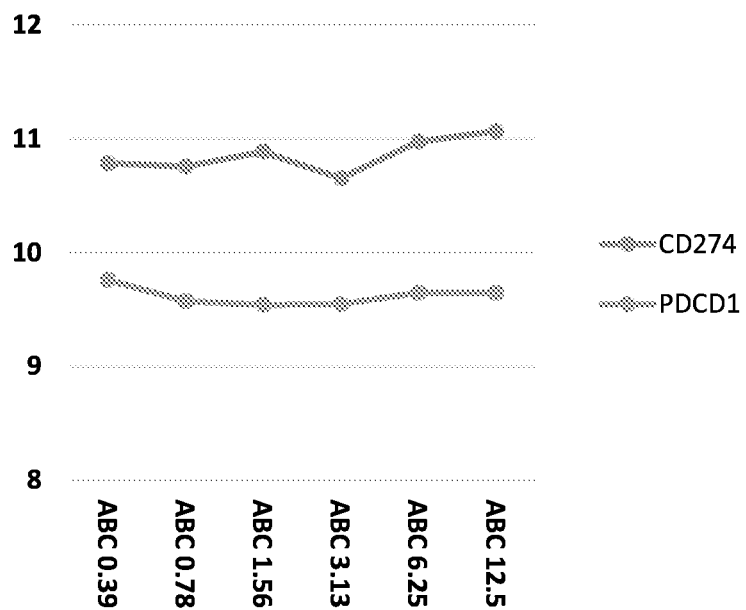
FIG. 7 is a graph showing Log 2 CPM for CD274 (PDL-1) and PDCD1 (PD1) in lysate prepared from an ABC FFPE sample.

Sample Input:

Replicate sample lysates from FFPE samples (one ABC and one GCB) were tested across two-fold dilutions between 12.5 and 0.39 $mm^2$ per well. Classification remained consistent in 100% of the 6 tested dilution points, even below the recommended 1.56 $mm^2$ of tissue. This consistency was also evaluated in two low expressing probes, CD274 (PD-L1) and PDCD1 (PD-1). FIGS. 6 and 7 depict sample expression in both ABC and GCB samples going from low to high sample input amounts.

Assay Repeatability:

Day to day repeatability was evaluated using 80 samples (40 ABC, 40 GCB) previously characterized by Affymetrix™ gene expression profiling (GEP). Samples previously characterized as "Unclassified" were purposely excluded. An equivalent of approximately 5 $mm^2$ of FFPE tissue was present in each sample well and sequenced on three separate days on a single HTG EdgeSeq processor and MiSeq Sequencer. Of the 240 total data sets produced, 236 (98.33%) passed pre-classification QC. One ABC and one GCB sample resulted in a QC failure on Day 1, two ABC samples on Day 2, and no samples on Day 3. Table 9 describes the final results of sample subtyping from the HTG EdgeSeq DLBCL Cell of Origin Assay compared with GEP, the overall agreement rate was 100% over all days.

TABLE 9

| HTG EdgeSeq DLBCL Cell of Origin Assay Classification to GEP | | | | | | |
|---|---|---|---|---|---|---|
| | Day 1 | | Day 2 | | Day 3 | |
| GEP | ABC | GCB | ABC | GCB | ABC | GCB |
| ABC | 39 | 0 | 38 | 0 | 40 | 0 |
| GCB | 0 | 39 | 0 | 40 | 0 | 40 |

Assay Concordance to IHC:

Agreement of the HTG EdgeSeq DLBCL Cell of Origin Assay compared to IHC methodologies was performed by way of a retrospective study using two independent cohorts. The first cohort consisted of 132 samples previously characterized as ABC or GCB via the Visco-Young method (Lenz et al., *N Engl J Med* 2008; 359(22):2313-23). A second cohort of 24 samples were characterized using the Choi method (Rosenwald et al., *N Engl J Med* 2002; 346(25):1937-47). Agreement rates, excluding unclassified samples, were calculated for each cohort. The HTG EdgeSeq DLBCL Cell of Origin Assay, as optimized to GEP, performed more consistently with the Choi IHC algorithm with a 91% overall agreement (Table 10). The overall agreement between the HTG EdgeSeq DLBCL Cell of Origin Assay and the Visco-Young IHC was 83% (Table 11). Neither of the overall agreement rates included the Unclassified samples as the IHC algorithms do not include this subtype classification category.

TABLE 10

HTG EdgeSeq DLBCL COO Assay Classification agreement with Choi IHC

| Choi | HTG EdgeSeq DLBCL COO | | |
|---|---|---|---|
| | ABC | GCB | UNC |
| ABC | 11 | 1 | 1 |
| GCB | 1 | 10 | 0 |
| Overall Agreement to Choi IHC | | 91% | |
| Unclassified rate | | 4% | |

TABLE 11

HTG EdgeSeq DLBCL Cell of Origin Assay Classification agreement with Visco-Young IHC

| Visco-Young IHC | HTGEdgeSeq DLBCL COO Assay | | |
|---|---|---|---|
| | ABC | GCB | UNC |
| ABC | 60 | 12 | 6 |
| GCB | 9 | 40 | 5 |
| Overall Agreement To Visco-Young IHC | | 83% | |
| Unclassified rate | | 6% | |

Diagnostic Reproducibility:

Fourteen previously characterized clinical samples were lysed at two sample input amounts. Three replicates for all samples were run across three HTG EdgeSeq processors, and sequenced on a single day. A total of 252 GCB/ABC classification calls were generated pooling across all conditions.

Figure 8:
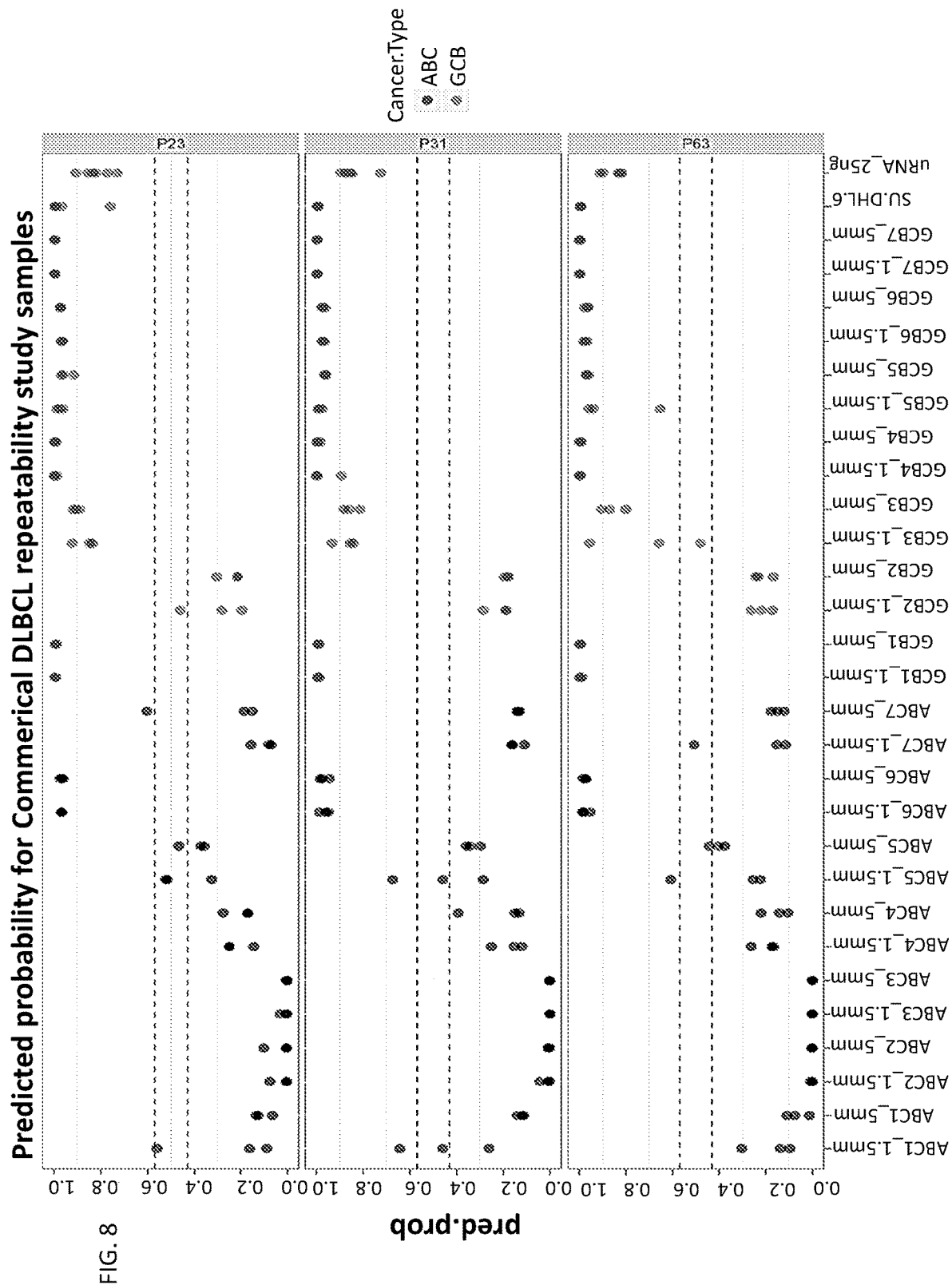
FIG. 8 is a graph showing a classification plot for each replicate and condition.

A total of 97% of samples (244/252) passed the QC metrics for subsequent classification. Ninety-nine percent (99%) agreement was obtained when unclassified samples were excluded (1 total misclassification); 97% agreement was obtained when unclassified results were included. There was a total of 8 unclassified results, 6 of these obtained from a single sample; these agreement rates are summarized in Table 12. Graphical representation of the classification for each replicate is shown in FIG. 8.

TABLE 12

Within Processor and Sample Input Agreement

| | | % Pass QC | % Agree |
|---|---|---|---|
| Processor | Instrument 1 (N = 83) | 98.8% | 94.0% |
| | Instrument 2 (N = 81) | 96.4% | 97.5% |
| | Instrument 3 (N = 80) | 95.2% | 97.5% |
| Sample Input | 1.5 mm (N = 118) | 93.7% | 94.9% |
| | 5 mm (N = 126) | 100.0% | 97.6% |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of treating a germinal center B-cell-like (GCB) diffuse large B-cell lymphoma (DLBCL), comprising:
measuring gene expression for each of CD47, CD86, ENTPD1, FOXP1, FUT8, IL16, ITPKB, LRMP, MME, NF2, PIM1, PTPRC, REL, STAT3, TNFRSF8, and TYMS, in a DLBCL sample obtained from a subject, to obtain a gene expression value for each of CD47, CD86, ENTPD1, FOXP1, FUT8, IL16, ITPKB, LRMP, MME, NF2, PIM1, PTPRC, REL, STAT3, TNFRSF8, and TYMS;
weighting each gene expression value, thereby generating weighted expression values;
summing the weighted expression values, thereby generating a summed weighted expression value;
calculating a probability score using the summed weighted expression value;
comparing the probability score to a predicted probability cut-off calculated from samples of known DLBCL status;
classifying the DLBCL sample as GCB; and
treating the subject with (1) cyclophosphamide, doxorubicin, vincristine, and prednisone or prednisolone (CHOP) chemotherapy; (2) rituximab plus CHOP (R-CHOP) chemotherapy; or (3) etoposide plus R-CHOP (R-EPOCH) chemotherapy.

2. The method of claim 1, wherein measuring gene expression comprises measuring mRNA, miRNA, or both.

3. The method of claim 1, wherein the DLBCL sample is a fixed sample.

4. The method of claim 1, wherein measuring gene expression comprises analyzing the DLBCL sample using a nuclease based assay.

5. The method of claim 1, wherein measuring gene expression comprises sequencing, and wherein the gene expression value is a count representing a number of molecules present in the DLBCL sample.

6. The method of claim 1, wherein measuring gene expression comprises quantification of expression.

7. The method of claim 1, wherein weighting each gene expression value comprises multiplying the gene expression value by the following coefficients:
−0.16 for CD47,
0.83 for CD86,
−0.71 for ENTPD1,
−0.56 for FOXP1,
−0.30 for FUT8,
−0.51 for IL16,
1.16 for ITPKB,
0.16 for LRMP,
0.59 for MME,
−0.70 for NF2,
−0.13 for PIM1,
0.07 for PTPRC,
0.20 for REL,
−0.17 for STAT3,
−0.01 for TNFRSF8, and
−0.25 for TYMS.

8. The method of claim 1, wherein calculating a probability score uses the formula:

$$Pr(Y = y \mid x) = \frac{e^{(\beta_0 + x^T \beta)}}{1 + e^{(\beta_0 + x^T \beta)}} \quad \text{(Equation 1)}$$

wherein β0 is a constant, β is a vector of weights for the classifier genes, and $x^T$ is a vector of measured values of the classifier genes for a given DLBCL sample.

9. The method of claim 1, wherein the predicted probability cut-off is a probability score t cut-off.

10. The method of claim 9, wherein the probability score t cut-off is >0.57 for GCB.

11. The method of claim 1 wherein the subject is known or suspected to have DLBCL.

12. The method of claim 1, wherein the gene expression value for each of CD47, CD86, ENTPD1, FOXP1, FUT8, IL16, ITPKB, LRMP, MME, NF2, PIM1, PTPRC, REL, STAT3, TNFRSF8, and TYMS is obtained by:
contacting the DLBCL sample with nuclease protection probes comprising a flanking sequence (NPPFs) specific for CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules under conditions sufficient for each NPPF to specifically bind to its target nucleic acid molecule;
contacting the DLBCL sample with a nucleic acid molecule comprising a sequence complementary to the flanking sequence (CFS) under conditions sufficient for the flanking sequence to specifically bind to the CFS;
contacting the DLBCL sample with a nuclease specific for single-stranded nucleic acid molecules under conditions sufficient to remove unbound nucleic acid molecules thereby generating a digested sample comprising NPPFs hybridized to the target nucleic acid molecules and to the CFS(s);
amplifying NPPFs in the digested sample with an amplification primer, thereby generating NPPF amplicons;
sequencing at least a portion of the NPPF amplicons; and
counting the number of NPPF amplicons; thereby determining the gene expression value for each of CD47, CD86, ENTPD1, FOXP1, FUT8, IL16, ITPKB, LRMP, MME, NF2, PIM1, PTPRC, REL, STAT3, TNFRSF8, and TYMS in the DLBCL sample.

13. The method of claim 1, wherein the gene expression value for each of CD47, CD86, ENTPD1, FOXP1, FUT8, IL16, ITPKB, LRMP, MME, NF2, PIM1, PTPRC, REL, STAT3, TNFRSF8, and TYMS is obtained by:
contacting the DLBCL sample with NPPFs specific for CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules,
wherein each NPPF comprises:
a 5'-end and a 3'-end,
a sequence complementary to a region of the CD47, CD86, ENTPD1, FOXP1, FUT8, IL16, ITPKB, LRMP, MME, NF2, PIM1, PTPRC, REL, STAT3, TNFRSF8, and TYMS target nucleic acid molecule, permitting specific binding between the NPPF and the target nucleic acid molecule,
wherein the flanking sequence is located 5', 3', or both, to the sequence complementary to the target nucleic acid molecule, wherein the 5'-flanking sequence is 5' of the sequence complementary to the target nucleic acid molecule, and the 3'-flanking sequence is 3' of the sequence complementary to the target nucleic acid molecule,
wherein the flanking sequence comprises at least 12 contiguous nucleotides not found in a nucleic acid molecule present in the DLBCL sample,
if the NPPF comprises a 5'-flanking sequence, contacting the DLBCL sample with a nucleic acid molecule comprising a sequence complementary to the 5'-flanking sequence (5CFS), a 5'-end phosphate, under conditions sufficient for the 5'-flanking sequence to specifically hybridize to the 5CFS;

if the NPPF comprises a 3'-flanking sequence, contacting the DLBCL sample with a nucleic acid molecule comprising a sequence complementary to the 3'-flanking sequence (3CFS) under conditions sufficient for the 3'-flanking sequence to specifically hybridize to the 3CFS;

wherein at least one of the 3CFS and the 5CFS comprises a capture moiety;

generating an NPPF hybridized to the target nucleic acid molecule, hybridized to the 3CFS, hybridized to the 5CFS, or hybridized to both the 3CFS and the 5CFS;

contacting the DLBCL sample with a nuclease specific for single-stranded nucleic acid molecules under conditions sufficient to remove unbound nucleic acid molecules, thereby generating a digested sample comprising NPPF hybridized to the target nucleic acid molecule, hybridized to the 3CFS, hybridized to the 5CFS, or hybridized to both the 3CFS and the 5CFS;

capturing the NPPF hybridized to the target nucleic acid molecule, hybridized to the 3CFS, hybridized to the 5CFS, or hybridized to both the 3CFS and the 5CFS;

ligating the 5'-phosphate of the 3CFS to a 3'-end of the target nucleic acid molecule, and ligating a 3'-end of the 5CFS to a 5'-end of the target nucleic acid molecule, thereby generating a ligated target nucleic acid molecule;

separating the NPPF from the ligated target nucleic acid molecule, thereby generating a mixture comprising single stranded NPPF and single stranded ligated target nucleic acid molecule; and sequencing at least a portion of the single stranded ligated target nucleic acid molecule, thereby determining the sequence of the CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules in the DLBCL sample.

14. The method of claim 13, wherein the NPPF comprises at least one dUTP, and the method further comprises contacting the mixture comprising single stranded NPPF and single stranded ligated target nucleic acid molecule with uracil DNA deglycosylase (UDG) under conditions sufficient for degrading the single stranded NPPF, after the denaturing and before the sequencing.

15. The method of claim 1, wherein a computing system is adapted to perform one or more steps of:

measuring gene expression for each of CD47, CD86, ENTPD1, FOXP1, FUT8, IL16, ITPKB, LRMP, MME, NF2, PIM1, PTPRC, REL, STAT3, TNFRSF8, and TYMS, in the DLBCL sample obtained from the subject, to obtain the gene expression value for each of CD47, CD86, ENTPD1, FOXP1, FUT8, IL16, ITPKB, LRMP, MME, NF2, PIM1, PTPRC, REL, STAT3, TNFRSF8, and TYMS;

weighting each expression value, thereby generating the weighted expression values;

summing the weighted expression values, thereby generating the summed weighted expression value;

calculating the probability score using the summed weighted expression value;

comparing the probability score to the predicted probability cut-off; and classifying the DLBCL sample as GCB.

16. The method of claim 1, wherein the subject is treated with CHOP chemotherapy.

17. The method of claim 1, wherein the subject is treated with R-CHOP chemotherapy.

18. The method of claim 1, wherein the subject is treated with R-EPOCH chemotherapy.

19. A method of treating an activated B-cell-like (ABC) diffuse large B-cell lymphoma (DLBCL), comprising:

measuring gene expression for each of CD47, CD86, ENTPD1, FOXP1, FUT8, IL16, ITPKB, LRMP, MME, NF2, PIM1, PTPRC, REL, STAT3, TNFRSF8, and TYMS, in a DLBCL sample obtained from a subject, to obtain a gene expression value for each of CD47, CD86, ENTPD1, FOXP1, FUT8, IL16, ITPKB, LRMP, MME, NF2, PIM1, PTPRC, REL, STAT3, TNFRSF8, and TYMS;

weighting each gene expression value, thereby generating weighted expression values;

summing the weighted expression values, thereby generating a summed weighted expression value;

calculating a probability score using the summed weighted expression value;

comparing the probability score to a predicted probability cut-off calculated from samples of known DLBCL status;

classifying the DLBCL sample as ABC; and treating the subject with a therapeutically effective amount of one or more of bendamustine, pixantrone, gemcitabine/oxaliplatin, liposomal vincristine, anti-CD20 mAb, anti-CD22 mAb, anti-CD74 mAb, anti-CD40 mAb, single-chain bispecific anti-CD19 and CD3 mAb construct, I-131 tositumomab, inotuzumab ozogamicin, 90Y-epratuzumab tetraxetan, thalidomide, lenalidomide, bortezomib, NPI-0052, everolimus, temsirolimus, vorinostat, oblimersen sodium, PF-3512676, 17-AAG, bevacizumab, aflibercept, CAL-101, valproic acid, dinaciclib, fostamatinib, dasatinib, enzastaurin, PCI-32765, SB1518, and sorafenib.

20. The method of claim 19, wherein measuring gene expression comprises measuring mRNA, miRNA, or both.

21. The method of claim 19, wherein the DLBCL sample is a fixed sample.

22. The method of claim 19, wherein measuring gene expression comprises analyzing the DLBCL sample using a nuclease based assay.

23. The method of claim 19, wherein measuring gene expression comprises sequencing, and wherein the gene expression value is a count representing a number of molecules present in the DLBCL sample.

24. The method of claim 19, wherein measuring gene expression comprises quantification of expression.

25. The method of claim 19, wherein weighting each gene expression value comprises multiplying the gene expression value by the following coefficients:

−0.16 for CD47,
0.83 for CD86,
−0.71 for ENTPD1,
−0.56 for FOXP1,
−0.30 for FUT8,
−0.51 for IL16,
1.16 for ITPKB,
0.16 for LRMP,
0.59 for MME,
−0.70 for NF2,
−0.13 for PIM1,
0.07 for PTPRC,
0.20 for REL,
−0.17 for STAT3,
−0.01 for TNFRSF8, and
−0.25 for TYMS.

26. The method of claim 19, wherein calculating a probability score uses the formula:

$$Pr(Y = y \mid x) = \frac{e^{(\beta_0 + x^T \beta)}}{1 + e^{(\beta_0 + x^T \beta)}} \quad \text{(Equation 1)}$$

wherein β0 is a constant, β is a vector of weights for the classifier genes, and $x^T$ is a vector of measured values of the classifier genes for a given DLBCL sample.

27. The method of claim 19, wherein the predicted probability cut-off is a probability score t cut-off.

28. The method of claim 27, wherein the probability score t cut-off is <0.43 for ABC.

29. The method of claim 19, wherein the gene expression value for each of CD47, CD86, ENTPD1, FOXP1, FUT8, IL16, ITPKB, LRMP, MME, NF2, PIM1, PTPRC, REL, STAT3, TNFRSF8, and TYMS is obtained by:
contacting the DLBCL sample with NPPFs specific for CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules, wherein each NPPF comprises:
a 5'-end and a 3'-end,
a sequence complementary to a region of the CD47, CD86, ENTPD1, FOXP1, FUT8, IL16, ITPKB, LRMP, MME, NF2, PIM1, PTPRC, REL, STAT3, TNFRSF8, and TYMS target nucleic acid molecule, permitting specific binding between the NPPF and the target nucleic acid molecule,
wherein the flanking sequence is located 5', 3', or both, to the sequence complementary to the target nucleic acid molecule, wherein the 5'-flanking sequence is 5' of the sequence complementary to the target nucleic acid molecule, and the 3'-flanking sequence is 3' of the sequence complementary to the target nucleic acid molecule,
wherein the flanking sequence comprises at least 12 contiguous nucleotides not found in a nucleic acid molecule present in the DLBCL sample,
if the NPPF comprises a 5'-flanking sequence, contacting the DLBCL sample with a nucleic acid molecule comprising a sequence complementary to the 5'-flanking sequence (5CFS), a 5'-end phosphate, under conditions sufficient for the 5'-flanking sequence to specifically hybridize to the 5CFS;
if the NPPF comprises a 3'-flanking sequence, contacting the DLBCL sample with a nucleic acid molecule comprising a sequence complementary to the 3'-flanking sequence (3CFS) under conditions sufficient for the 3'-flanking sequence to specifically hybridize to the 3CFS;
wherein at least one of the 3CFS and the 5CFS comprises a capture moiety;
generating an NPPF hybridized to the target nucleic acid molecule, hybridized to the 3CFS, hybridized to the 5CFS, or hybridized to both the 3CFS and the 5CFS;
contacting the DLBCL sample with a nuclease specific for single-stranded nucleic acid molecules under conditions sufficient to remove unbound nucleic acid molecules, thereby generating a digested sample comprising NPPF hybridized to the target nucleic acid molecule, hybridized to the 3CFS, hybridized to the 5CFS, or hybridized to both the 3CFS and the 5CFS;
capturing the NPPF hybridized to the target nucleic acid molecule, hybridized to the 3CFS, hybridized to the 5CFS, or hybridized to both the 3CFS and the 5CFS;
ligating the 5'-phosphate of the 3CFS to a 3'-end of the target nucleic acid molecule, and ligating a 3'-end of the 5CFS to a 5'-end of the target nucleic acid molecule, thereby generating a ligated target nucleic acid molecule;
separating the NPPF from the ligated target nucleic acid molecule, thereby generating a mixture comprising single stranded NPPF and single stranded ligated target nucleic acid molecule; and
sequencing at least a portion of the single stranded ligated target nucleic acid molecule, thereby determining the sequence of the CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules in the DLBCL sample.

30. The method of claim 29, wherein the NPPF comprises at least one dUTP, and the method further comprises contacting the mixture comprising single stranded NPPF and single stranded ligated target nucleic acid molecule with uracil DNA deglycosylase (UDG) under conditions sufficient for degrading the single stranded NPPF, after the denaturing and before the sequencing.

31. The method of claim 19, wherein the subject is known or suspected to have DLBCL.

32. The method of claim 19, wherein the gene expression value for each of CD47, CD86, ENTPD1, FOXP1, FUT8, IL16, ITPKB, LRMP, MME, NF2, PIM1, PTPRC, REL, STAT3, TNFRSF8, and TYMS is obtained by:
contacting the DLBCL sample with NPPFs specific for CD47, CD86, ENTPD1, FOXP1, FUT8, IL16, ITPKB, LRMP, MME, NF2, PIM1, PTPRC, REL, STAT3, TNFRSF8, and TYMS target nucleic acid molecules under conditions sufficient for each NPPF to specifically bind to its target nucleic acid molecule;
contacting the DLBCL sample with a nucleic acid molecule comprising a sequence complementary to the flanking sequence (CFS) under conditions sufficient for the flanking sequence to specifically bind to the CFS;
contacting the DLBCL sample with a nuclease specific for single-stranded nucleic acid molecules under conditions sufficient to remove unbound nucleic acid molecules thereby generating a digested sample comprising NPPFs hybridized to the target nucleic acid molecules and to the CFS(s);
amplifying NPPFs in the digested sample with an amplification primer, thereby generating NPPF amplicons;
sequencing at least a portion of the NPPF amplicons; and
counting the number of NPPF amplicons; thereby determining the gene expression value for each of CD47, CD86, ENTPD1, FOXP1, FUT8, IL16, ITPKB, LRMP, MME, NF2, PIM1, PTPRC, REL, STAT3, TNFRSF8, and TYMS in the DLBCL sample.

33. The method of claim 19, wherein a computing system is adapted to perform one or more steps of:
measuring gene expression for each of CD47, CD86, ENTPD1, FOXP1, FUT8, IL16, ITPKB, LRMP, MME, NF2, PIM1, PTPRC, REL, STAT3, TNFRSF8, and TYMS, in the DLBCL sample obtained from the subject, to obtain the gene expression value for each of CD47, CD86, ENTPD1, FOXP1, FUT8, IL16, ITPKB, LRMP, MME, NF2, PIM1, PTPRC, REL, STAT3, TNFRSF8, and TYMS;
weighting each expression value, thereby generating the weighted expression values;

summing the weighted expression values, thereby generating the summed weighted expression value;
calculating the probability score using the summed weighted expression value;
comparing the probability score to the predicted probability cut-off; and
classifying the DLBCL sample as ABC.

* * * * *